US012753228B2

(12) United States Patent
Morgenstern et al.

(10) Patent No.: US 12,753,228 B2
(45) Date of Patent: Oct. 6, 2026

(54) COMPOSITIONS AND METHODS FOR GENETICALLY-ENCODED HIGH VOLTAGE-ACTIVATED CALCIUM CHANNEL BLOCKERS USING ENGINEERED UBIQUITIN LIGASES

(71) Applicant: The Trustees of Columbia University in the City of New York, New York, NY (US)

(72) Inventors: Travis Morgenstern, New York, NY (US); Henry M. Colecraft, New Jersey, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1197 days.

(21) Appl. No.: 17/486,394

(22) Filed: Sep. 27, 2021

(65) Prior Publication Data

US 2022/0033493 A1 Feb. 3, 2022

Related U.S. Application Data

(63) Continuation of application No. PCT/US2020/025359, filed on Mar. 27, 2020.

(60) Provisional application No. 62/886,733, filed on Aug. 14, 2019, provisional application No. 62/883,637, filed on Aug. 6, 2019, provisional application No. 62/854,688, filed on May 30, 2019, provisional application No. 62/830,142, filed on Apr. 5, 2019, provisional application No. 62/825,784, filed on Mar. 28, 2019.

(51) Int. Cl.
*C07K 16/28* (2006.01)
*C12N 9/10* (2006.01)
*C12N 9/12* (2006.01)

(52) U.S. Cl.
CPC .............. *C07K 16/28* (2013.01); *C12N 9/104* (2013.01); *C12N 9/12* (2013.01); *C07K 2317/22* (2013.01); *C07K 2317/569* (2013.01); *C07K 2319/00* (2013.01)

(58) Field of Classification Search
None
See application file for complete search history.

(56) References Cited

U.S. PATENT DOCUMENTS 5,851,783 A 12/1998 Appel et al.
2015/0250854 A1 9/2015 Beguin et al.

FOREIGN PATENT DOCUMENTS

WO 2009019508 2/2009

OTHER PUBLICATIONS

Van Petegem, et al. "Structure of a complex between a voltage-gated calcium channel beta-subunit and an alpha-subunit domain," Nature. 2004;429:671-675. doi: 10.1038/nature02588.

Waithe, et al. "Beta-subunits promote the expression of ca(V)2.2 channels by reducing their proteasomal degradation," The Journal of Biological Chemistry. 2011;286:9598-9611. doi: 10.1074/jbc.M110.195909.

Ward, et al. "Phosphorylation of critical serine residues in gem separates cytoskeletal reorganization from down-regulation of calcium channel activity," Molecular and Cellular Biology. 2004;24:651-661. doi: 10.1128/MCB.24.2.651-661.2004.

Xu, et al. "Molecular mechanisms, and selective pharmacological rescue, of Rem-inhibited CaV1.2 channels in heart," Circulation Research. 2010;107:620-630. doi: 10.1161/CIRCRESAHA.110.224717.

Yang, et al. "Rem, a member of the RGK GTPases, inhibits recombinant CaV1.2 channels using multiple mechanisms that require distinct conformations of the GTPase," The Journal of Physiology. 2010;588:1665-1681. doi: 10.1113/jphysiol.2010.187203.

Yang, et al. "Bio-inspired voltage-dependent calcium channel blockers," Nature Communications. 2013;4:2540. doi: 10.1038/ncomms3540.

Yang, et al. "Cardiac CaV1.2 channels require 13 subunits for 13-adrenergic-mediated modulation but not trafficking," Journal of Clinical Investigation. 2019;129:647-658. doi: 10.1172/JCI123878.

Yang and Berggren "The role of voltage-gated calcium channels in pancreatic beta-cell physiology and pathophysiology," Endocrine Reviews. 2006;27:621-676. doi: 10.1210/er.2005-0888.

Yang and Colecraft "Regulation of voltage-dependent calcium channels by RGK proteins," Biochimica Et Biophysica Acta (BBA) Biomembranes. 2013;1828:1644-1654. doi: 10.1016/j.bbamem.2012.10.005.

Young, et al. "Identification of a calcium channel modulator using a high throughput yeast two-hybrid screen," Nature Biotechnology. 1998;16:946-950. doi: 10.1038/nbt1098-946.

Zamponi, et al. "The physiology, pathology, and pharmacology of Voltage-Gated calcium channels and their future therapeutic potential," Pharmacological Reviews. 2015;67:821-870. doi: 10.1124/pr.114.009654.

(Continued)

*Primary Examiner* — Ruixiang Li
(74) *Attorney, Agent, or Firm* — Bryan Cave Leighton Paisner LLP

(57) ABSTRACT

The present disclosure provides, inter alia, nanobodies targeting a $Ca_V\beta$ auxiliary subunit and compositions thereof. Methods for blocking a High-Voltage Activated Calcium Channel (HVACC) using such compositions, methods for selectively targeting a population of cells in a subject, and methods for treating or ameliorating the effects of a disease in a subject are also provided.

14 Claims, 54 Drawing Sheets
(51 of 54 Drawing Sheet(s) Filed in Color)
Specification includes a Sequence Listing.

(56) References Cited

OTHER PUBLICATIONS

Zamponi "Targeting voltage-gated calcium channels in neurological and psychiatric diseases," Nature Reviews Drug Discovery. 2016;15:19-34. doi: 10.1038/nrd.2015.5.
International Search Report and Written Opinion for PCT/US20/25359 dated Jul. 22, 2020.
Morgenstern, et al. "A Potent Voltage-Gated Calcium Channel Inhibitor Engineered from a Nanobody Targeted to Auxiliary CaVβ Subunites," eLife Aug. 12, 2019, vol. 8, e49253 pp. 1-23.
Albuquerque, et al. "Dissection, plating, and maintenance of dorsal root ganglion neurons for monoculture and for coculture with dorsal horn neurons," Cold Spring Harbor Protocols. 2009 prot5275.
Andris-Widhopf, et al. "Methods for the generation of chicken monoclonal antibody fragments by phage display," Journal of Immunological Methods. 2000;242:159-181 doi: 10.1016/S0022-1759(00)00221-0.
Aromolaran, et al. "LQT1 mutations in KCNQ1 C-terminus assembly domain suppress IKs using different mechanisms," Cardiovascular Research. 2014; 104:501-511. doi: 10.1093/cvr/cvu231.
Bannister, et al. "Rem inhibits skeletal muscle EC coupling by reducing the number of functional L-type Ca2+ channels," Biophysical Journal. 2008;94:2631-2638. doi: 10.1529/biophysj.107.116467.
Béguin, et al. "Regulation of Ca2+ channel expression at the cell surface by the small G-protein kir/Gem," Nature. 2001;411:701-706. doi: 10.1038/35079621.
Béguin, et al. "14-3-3 and calmodulin control subcellular distribution of kir/Gem and its regulation of cell shape and calcium channel activity," Journal of Cell Science. 2005;118:1923-1934. doi: 10.1242/jcs.02321.
Bers, "Cardiac excitation-contraction coupling," Nature. 2002;415:198-205. doi: 10.1038/415198a.
Brice and Dolphin, "Differential plasma membrane targeting of voltage-dependent calcium channel subunits expressed in a polarized epithelial cell line," The Journal of Physiology. 1999;515:685-694. doi: 10.1111/j.1469-7793.1999.685ab.x.
Buraei and Yang "The β subunit of voltage-gated Ca2+ channels," Physiological Reviews. 2010;90:1461-1506. doi: 10.1152/physrev.00057.2009.
Campiglio and Flucher "The role of auxiliary subunits for the functional diversity of voltage-gated calcium channels," Journal of Cellular Physiology. 2015;230:2019-2031. doi: 10.1002/jcp.24998.
Chen, et al. "Structural basis of the α1-β subunit interaction of voltage-gated Ca2+ channels," Nature. 2004;429:675-6 doi: 10.1038/nature02641.
Chen, et al. "Expression of Rem2, an RGK family small GTPase, reduces N-type calcium current without affecting channel surface density," Journal of Neuroscience. 2005;25:9762-9772. doi: 10.1523/JNEUROSCI.3111-05.2005.
Chen, "Small-molecule CaValpha1CaVbeta antagonist suppresses neuronal voltage-gated calcium-channel trafficking," PNAS. 2018;115:E10566-E10575. doi: 10.1073/pnas.1813157115.
Chien, et al. "Identification of palmitoylation sites within the L-type calcium channel beta2a subunit and effects on channel function," Journal of Biological Chemistry. 1996;271:26465-26468. doi: 10.1074/jbc.271.43.26465.
Colecraft, et al. "Novel functional properties of ca(2+) channel beta subunits revealed by their expression in adult rat heart cells," The Journal of Physiology. 2002;541:435-452. doi: 10.1113/jphysiol.2002.018515.
Copits and Swanson "Dancing partners at the synapse: auxiliary subunits that shape kainate receptor function," Nature Reviews Neuroscience. 2012; 13:675-686. doi: 10.1038/nrn3335.
Correll, et al. "The RGK family of GTP-binding proteins: regulators of voltage-dependent calcium channels and cytoskeleton remodeling," Cellular Signalling. 2008;20:292-300. doi: 10.1016/j.cellsig.2007.10.028.
Dolphin, "Calcium channel auxiliary a2δ and β subunits: trafficking and one step beyond," Nature Reviews Neuroscience. 2012;13:542-555. doi: 10.1038/nrn3311.
Findeisen, et al. "Stapled Voltage-Gated calcium channel (CaV) α-Interaction Domain (AID) Peptides Act As Selective Protein-Protein Interaction Inhibitors of CaV Function," ACS Chemical Neuroscience. 2017;8:1313-1326. doi: 10.1021/acschemneuro.6b00454.
Finlin, et al. "Regulation of voltage-gated calcium channel activity by the rem and rad GTPases," PNAS. 2003;100:14469-14474. doi: 10.1073/pnas.2437756100.
Gao, et al. "Ubiquitin ligase Nedd4L targets activated Smad2/3 to limit TGF-beta signaling," Molecular Cell. 2009;36:457-468. doi: 10.1016/j.molcel.2009.09.043.
Gee, et al. "The novel anticonvulsant drug, gabapentin (Neurontin), binds to the alpha2delta subunit of a calcium channel," Journal of Biological Chemistry. 1996;271:5768-5776. doi: 10.1074/jbc.271.10.5768.
Gibson,et al. Enzymatic assembly of DNA molecules up to several hundred kilobases. Nature Methods. 2009;6:343-345. doi: 10.1038/nmeth.1318.
Goehring, et al. Screening and large-scale expression of membrane proteins in mammalian cells for structural studies. Nature Protocols. 2014;9:2574-2585. doi: 10.1038/nprot.2014.173.
Han, et al. "A subpopulation of nociceptors specifically linked to itch," Nature Neuroscience. 2013;16:174-182. doi: 10.1038/nn.3289.
Jagodic, et al. "Upregulation of the T-type calcium current in small rat sensory neurons after chronic constrictive injury of the sciatic nerve," Journal of Neurophysiology. 2008;99:3151-3156. doi: 10.1152/jn.01031.2007.
Kanner, et al. "Sculpting ion channel functional expression with engineered ubiquitin ligases," eLife. 2017;6:e29744. doi: 10.7554/eLife.29744.
Khanna, et al. "Targeting the CaVα-CaVβ interaction yields an antagonist of the N-type CaV2.2 channel with broad antinociceptive efficacy," Pain. 2019;160:1644-1661. doi: 10.1097/j.pain.0000000000001524.
Kim, et al. "Coupled activation of primary sensory neurons contributes to chronic pain," Neuron. 2016;91:1085-1096. doi: 10.1016/j.neuron.2016.07.044.
Kim and Huibregtse "Polyubiquitination by HECT E3s and the determinants of chain type specificity," Molecular and Cellular Biology. 2009;29:3307-3318. doi: 10.1128/MCB.00240-09.
Makarewich, et al. "A caveolae-targeted L-type Ca2+ channel antagonist inhibits hypertrophic signaling without reducing cardiac contractility," Circulation Research. 2012;110:669-674.doi: 10.1161/CIRCRESAHA.111.264028.
McCallum, et al. "Subtype-specific reduction of voltage-gated calcium current in medium-sized dorsal root ganglion neurons after painful peripheral nerve injury," Neuroscience. 2011;179:244-255. doi: 10.1016/j.neuroscience.2011.01.049.
McEnery, et al. "Altered expression and assembly of N-type calcium channel alpha1B and beta subunits in epileptic lethargic (lh/lh) mouse," The Journal of Biological Chemistry. 1998;273:21435-21438. doi: 10.1074/jbc.273.34.21435.
McMahon, et al. "Yeast surface display platform for rapid discovery of conformationally selective nanobodies," Nature Structural & Molecular Biology. 2018;25:289-296. doi: 10.1038/s41594-018-0028-6.
Meissner, et al. "Moderate calcium channel dysfunction in adult mice with inducible cardiomyocyte-specific excision of the cacnb2 gene," Journal of Biological Chemistry. 2011;286:15875-15882. doi: 10.1074/jbc.M111.227819.
Murali, et al. "High-voltage-activated calcium current subtypes in mouse DRG neurons adapt in a subpopulation-specific manner after nerve injury," Journal of Neurophysiology. 2015;113:1511-1519. doi: 10.1152/jn.00608.2014.
Murata, et al. "Creation of a genetic calcium channel blocker by targeted gem gene transfer in the heart," Circulation Research. 2004;95:398-405. doi: 10.1161/01.RES.0000138449.85324.c5.

(56) References Cited

OTHER PUBLICATIONS

O'Malley and Isom "Sodium channel β subunits: emerging targets in channelopathies," Annual Review of Physiology. 2015;77:481-504. doi: 10.1146/annurev-physiol-021014-071846.
Opatowsky, et al. "The voltage-dependent calcium channel beta subunit contains two stable interacting domains," Journal of Biological Chemistry. 2003;278:52323-52332. doi: 10.1074/jbc.M303564200.
Pardon, et al. "A general protocol for the generation of nanobodies for structural biology," Nature Protocols. 2014;9:674-693. doi: 10.1038/nprot.2014.039.
Pragnell, et al. "Calcium channel beta-subunit binds to a conserved motif in the I-II cytoplasmic Linker of the alpha 1-subunit," Nature. 1994;368:67-70. doi: 10.1038/368067a0.
Puckerin, et al. "Engineering selectivity into RGK GTPase inhibition of voltage-dependent calcium channels," PNAS. 2018;115:12051-12056. doi: 10.1073/pnas.1811024115.
Rink, et al. "Rab conversion as a mechanism of progression from early to late endosomes," Cell. 2005;122:735-749. doi: 10.1016/j.cell.2005.06.043.
Royer, et al. "The Ras-like GTPase Rem2 is a potent inhibitor of calcium/calmodulin-dependent kinase II activity," Journal of Biological Chemistry. 2018;293:14798-14811. doi: 10.1074/jbc.RA118.003560.
Scheffner and Kumar "Mammalian HECT ubiquitin-protein ligases: biological and pathophysiological aspects," Biochimica Et Biophysica Acta (BBA)—Molecular Cell Research. 2014;1843:61-74. doi: 10.1016/j.bbamcr.2013.03.024.
Scriven, et al. "Distribution of proteins implicated in excitation-contraction coupling in rat ventricular myocytes," Biophysical Journal. 2000;79:2682-2691. doi: 10.1016/S0006-3495(00)76506-4.
Shaw and Colecraft "L-type calcium channel targeting and local signalling in cardiac myocytes," Cardiovascular Research. 2013;98:177-186. doi: 10.1093/cvr/cvt021.
Stull, et al. "Mouse islet of Langerhans isolation using a combination of purified collagenase and neutral protease," Journal of Visualized Experiments. 2012;4137:e4137. doi: 10.3791/4137.
Subramanyam "Manipulating L-type calcium channels in cardiomyocytes using split-intein protein transsplicing," PNAS. 2013;110:15461-15466.
Trimmer "Subcellular localization of K+ channels in mammalian brain neurons: remarkable precision in the midst of extraordinary complexity," Neuron. 2015;85:238-256. doi: 10.1016/j.neuron.2014.12.042.
Rosa, "The [beta] and [alpha]2[delta] auxiliary subunits of voltage-gated calcium channel 1 (Cav1) are required for TH2 lymphocyte function and acute allergic airway inflammation", Journal of Allergy and Clinical Immunology, vol. 142, No. 3.
Bannas, "Nanobodies and Nanobody-Based Human Heavy Chain Antibodies As Antitumor Therapeutics", Frontiers in Immunology, vol. 8, Nov. 22, 2017.
Unciti-Broceta, "Novel therapy based on camelid nanobodies", Therapeutic Delivery, vol. 4, No. 10, Oct. 1, 2013.
Communication Pursuant to Rule 164(1), EP Application No. 20780047.5, dated Mar. 17, 2023.

Figure 1E

```
                   FW3         CDR3          FW4
A1.p1    KPEDTAVYYCAAIEGMRIS-PVVTGIPAFDFGSWGQGTQVTVSS  (see SEQ ID NO: 4)
D1.p1    KPEDTAVYYCTLYMRTE------AQSRGTGYDYWGQGTQVTVSS  (see SEQ ID NO: 12)
A11.p2   KPEDTAVYYCAAHY--QGS-----YGSALAYDTWGQGTQVTVSS  (see SEQ ID NO: 24)
D10.p3   KPEDTAVYYCALDDDTFG------VTTSTHYDYWGQGTQVTVSS  (see SEQ ID NO: 40)
E11.p3   KPEDTAVYYCAAEVFYSGSYDDTLRVQSHEYDYWGQGTQVTVSS  (see SEQ ID NO: 48)
A7.p1    KPEDTAVYYCAADTYYGSR-------MWNEYDYWGQGTQVTVSS  (see SEQ ID NO: 8)
F3.p3    KPEDTAVYYCAASSYWS-R-------SVDEYDYWGQGTQVTVSS  (see SEQ ID NO: 86)
         **********:                   : :***********
```

| | |
|---|---|
| N | 0.93 ± 0.02 |
| $K_d$ (nM) | 13.2 ± 7.2 |
| $K_a$ ($M^{-1}$x$10^7$) | 10.7 ± 5.8 |
| ΔH (kcal $mol^{-1}$) | -14.9 ± 5.8 |
| ΔS (cal $mol^{-1}$ $K^{-1}$) | -13.8 ± 20.5 |

SEQUENCE LISTING

```
<160> NUMBER OF SEQ ID NOS: 98

<210> SEQ ID NO 1
<211> LENGTH: 9
<212> TYPE: PRT
<213> ORGANISM: Artificial Sequence
<220> FEATURE:
<223> OTHER INFORMATION: nanobody

<400> SEQUENCE: 1

Ser Gly Phe Thr Phe Asp Asp Tyr Ala
1               5
```

<210> SEQ ID NO 2
<211> LENGTH: 10
<212> TYPE: PRT
<213> ORGANISM: Artificial Sequence
<220> FEATURE:
<223> OTHER INFORMATION: nanobody

<400> SEQUENCE: 2

```
Val Ser Cys Phe Ser Ser Ser Asp Gly Ser
1               5                   10
```

<210> SEQ ID NO 3
<211> LENGTH: 20
<212> TYPE: PRT
<213> ORGANISM: Artificial Sequence
<220> FEATURE:
<223> OTHER INFORMATION: nanobody

<400> SEQUENCE: 3

```
Ile Glu Gly Met Arg Ile Ser Pro Val Val Thr Gly Ile Pro Ala Phe
1               5                   10                  15

Asp Phe Gly Ser
            20
```

<210> SEQ ID NO 4
<211> LENGTH: 129
<212> TYPE: PRT
<213> ORGANISM: Artificial Sequence
<220> FEATURE:
<223> OTHER INFORMATION: nanobody

<400> SEQUENCE: 4

```
Gln Val Gln Leu Gln Glu Ser Gly Gly Gly Leu Val Gln Pro Gly Gly
1               5                   10                  15

Ser Leu Arg Leu Ser Cys Ala Val Ser Gly Phe Thr Phe Asp Asp Tyr
            20                  25                  30

Ala Ile Gly Trp Phe Arg Gln Ala Pro Gly Lys Glu Arg Glu Ala Val
        35                  40                  45

Ser Cys Phe Ser Ser Ser Asp Gly Ser Thr Tyr Tyr Ala Asp Ser Val
    50                  55                  60

Lys Gly Arg Phe Thr Ile Ser Ser Asp Asn Asp Lys Asn Met Val Tyr
65                  70                  75                  80

Leu Gln Met Asn Ser Leu Lys Pro Glu Asp Thr Ala Val Tyr Tyr Cys
                85                  90                  95

Ala Ala Ile Glu Gly Met Arg Ile Ser Pro Val Val Thr Gly Ile Pro
            100                 105                 110

Ala Phe Asp Phe Gly Ser Trp Gly Gln Gly Thr Gln Val Thr Val Ser
        115                 120                 125

Ser
```

<210> SEQ ID NO 5
<211> LENGTH: 9
<212> TYPE: PRT
<213> ORGANISM: Artificial Sequence
<220> FEATURE:
<223> OTHER INFORMATION: nanobody

<400> SEQUENCE: 5

```
Ser Gly Arg Thr Phe Ser Ser Tyr Thr
1               5
```

<210> SEQ ID NO 6
<211> LENGTH: 6
<212> TYPE: PRT
<213> ORGANISM: Artificial Sequence
<220> FEATURE:
<223> OTHER INFORMATION: nanobody

<400> SEQUENCE: 6

```
Ile Ser Trp Ser Gly Gly
1               5
```

<210> SEQ ID NO 7
<211> LENGTH: 11
<212> TYPE: PRT
<213> ORGANISM: Artificial Sequence
<220> FEATURE:
<223> OTHER INFORMATION: nanobody

<400> SEQUENCE: 7

```
Asp Thr Tyr Tyr Gly Ser Arg Met Trp Asn Glu
1               5                   10
```

<210> SEQ ID NO 8
<211> LENGTH: 123
<212> TYPE: PRT
<213> ORGANISM: Artificial Sequence
<220> FEATURE:
<223> OTHER INFORMATION: nanobody

<400> SEQUENCE: 8

```
Gln Val Gln Leu Gln Glu Ser Gly Gly Gly Leu Val Gln Ala Gly Gly
1               5                   10                  15

Ser Val Arg Leu Ser Cys Ala Ala Ser Gly Arg Thr Phe Ser Ser Tyr
            20                  25                  30

Thr Met Gly Trp Phe Arg Gln Ala Pro Gly Lys Glu Arg Glu Phe Val
        35                  40                  45

Ala Ala Ile Ser Trp Ser Gly Gly Thr Thr Tyr Tyr Ala Asp Ser Val
    50                  55                  60

Lys Gly Arg Phe Ala Ile Ala Arg Asp Asn Ala Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Ala Asp Thr Tyr Tyr Gly Ser Arg Met Trp Asn Glu Tyr Asp Tyr
            100                 105                 110

Trp Gly Gln Gly Thr Gln Val Thr Val Ser Ser
        115                 120
```

<210> SEQ ID NO 9
<211> LENGTH: 9
<212> TYPE: PRT
<213> ORGANISM: Artificial Sequence
<220> FEATURE:
<223> OTHER INFORMATION: nanobody

<400> SEQUENCE: 9

```
Ser Gly Ser Ile Leu Thr Ile Asn Val
1               5
```

<210> SEQ ID NO 10
<211> LENGTH: 7
<212> TYPE: PRT
<213> ORGANISM: Artificial Sequence
<220> FEATURE:

<223> OTHER INFORMATION: nanobody

<400> SEQUENCE: 10

His Ala Ser Ser Gly Gly Ser
1 5

<210> SEQ ID NO 11
<211> LENGTH: 14
<212> TYPE: PRT
<213> ORGANISM: Artificial Sequence
<220> FEATURE:
<223> OTHER INFORMATION: nanobody

<400> SEQUENCE: 11

Thr Leu Tyr Met Arg Thr Glu Ala Gln Ser Arg Gly Thr Gly
1 5 10

<210> SEQ ID NO 12
<211> LENGTH: 123
<212> TYPE: PRT
<213> ORGANISM: Artificial Sequence
<220> FEATURE:
<223> OTHER INFORMATION: nanobody

<400> SEQUENCE: 12

Gln Val Gln Leu Gln Glu Ser Gly Gly Gly Leu Val Gln Pro Gly Gly
1 5 10 15

Ser Leu Arg Leu Ser Cys Thr Ala Ser Gly Ser Ile Leu Thr Ile Asn
20 25 30

Val Met Gly Trp Tyr Arg Gln Ala Pro Gly Lys Gln Arg Glu Leu Val
35 40 45

Ala His Ala Ser Ser Gly Gly Ser Thr Asp Tyr Ala Asp Ser Val Lys
50 55 60

Gly Arg Phe Thr Ile Ser Arg Asp Asn Ala Lys Asn Thr Trp Tyr Leu
65 70 75 80

Gln Met Asn Asn Leu Lys Pro Glu Asp Thr Ala Val Tyr Tyr Cys Thr
85 90 95

Leu Tyr Met Arg Thr Glu Ala Gln Ser Arg Gly Thr Gly Tyr Asp Tyr
100 105 110

Trp Gly Gln Gly Thr Gln Val Thr Val Ser Ser
115 120

<210> SEQ ID NO 13
<211> LENGTH: 9
<212> TYPE: PRT
<213> ORGANISM: Artificial Sequence
<220> FEATURE:
<223> OTHER INFORMATION: nanobody

<400> SEQUENCE: 13

Ser Gly Arg Thr Phe Ser Ser Tyr Ala
1 5

<210> SEQ ID NO 14
<211> LENGTH: 10
<212> TYPE: PRT
<213> ORGANISM: Artificial Sequence
<220> FEATURE:
<223> OTHER INFORMATION: nanobody

<400> SEQUENCE: 14

Ile Glu Arg Ser Gly Gly Thr Ala Ser His
1 5 10

<210> SEQ ID NO 15
<211> LENGTH: 10
<212> TYPE: PRT
<213> ORGANISM: Artificial Sequence
<220> FEATURE:
<223> OTHER INFORMATION: nanobody

<400> SEQUENCE: 15

```
Ser Ser Tyr Trp Ser Arg Ser Val Ala Glu
1               5                   10
```

<210> SEQ ID NO 16
<211> LENGTH: 122
<212> TYPE: PRT
<213> ORGANISM: Artificial Sequence
<220> FEATURE:
<223> OTHER INFORMATION: nanobody

<400> SEQUENCE: 16

```
Gln Val Gln Leu Gln Glu Ser Gly Gly Gly Leu Val Gln Ala Gly Gly
1               5                   10                  15

Ser Val Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Glu Arg Ser Gly Gly Thr Ala Ser His Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Ser Cys
                85                  90                  95

Ala Ala Ser Ser Tyr Trp Ser Arg Ser Val Ala Glu Tyr Asp Tyr Trp
            100                 105                 110

Gly Gln Gly Thr Gln Val Thr Val Ser Ser
        115                 120
```

<210> SEQ ID NO 17
<211> LENGTH: 9
<212> TYPE: PRT
<213> ORGANISM: Artificial Sequence
<220> FEATURE:
<223> OTHER INFORMATION: nanobody

<400> SEQUENCE: 17

```
Ser Glu Arg Thr Phe Ser Arg Tyr Ala
1               5
```

<210> SEQ ID NO 18
<211> LENGTH: 7
<212> TYPE: PRT
<213> ORGANISM: Artificial Sequence
<220> FEATURE:
<223> OTHER INFORMATION: nanobody

<400> SEQUENCE: 18

```
Ile Asn Trp Ser Gly Ser Ser
1               5
```

<210> SEQ ID NO 19
<211> LENGTH: 11
<212> TYPE: PRT
<213> ORGANISM: Artificial Sequence
<220> FEATURE:
<223> OTHER INFORMATION: nanobody

<400> SEQUENCE: 19

His Tyr Gln Gly Ser Tyr Gly Ser Ala Leu Ala
1 5 10

<210> SEQ ID NO 20
<211> LENGTH: 123
<212> TYPE: PRT
<213> ORGANISM: Artificial Sequence
<220> FEATURE:
<223> OTHER INFORMATION: nanobody

<400> SEQUENCE: 20

Gln Val Gln Leu Gln Glu Ser Gly Gly Gly Leu Val Gln Ala Gly Gly
1 5 10 15

Ser Leu Arg Leu Ser Cys Ala Ala Ser Glu Arg Thr Phe Ser Arg Tyr
20 25 30

Ala Met Gly Trp Phe Arg Gln Ala Pro Glu Lys Glu Arg Glu Phe Val
35 40 45

Ala Ala Ile Asn Trp Ser Gly Ser Ser Thr Tyr Tyr Ala Asp Ser Val
50 55 60

Lys Gly Arg Phe Thr Val Ser Arg Asp Asp Ala Lys Asn Thr Val Tyr
65 70 75 80

Leu Gln Met Asn Ser Leu Lys Pro Glu Asp Thr Ala Val Tyr Tyr Cys
85 90 95

Ala Ala His Tyr Gln Gly Ser Tyr Gly Ser Ala Leu Ala Tyr Asp Ile
100 105 110

Trp Gly Gln Gly Thr Gln Val Thr Val Ser Ser
115 120

<210> SEQ ID NO 21
<211> LENGTH: 9
<212> TYPE: PRT
<213> ORGANISM: Artificial Sequence
<220> FEATURE:
<223> OTHER INFORMATION: nanobody

<400> SEQUENCE: 21

Ser Glu Arg Thr Phe Ser Arg Tyr Ala
1 5

<210> SEQ ID NO 22
<211> LENGTH: 7
<212> TYPE: PRT
<213> ORGANISM: Artificial Sequence
<220> FEATURE:
<223> OTHER INFORMATION: nanobody

<400> SEQUENCE: 22

Ile Asn Trp Ser Gly Ser Ser
1 5

<210> SEQ ID NO 23
<211> LENGTH: 11
<212> TYPE: PRT
<213> ORGANISM: Artificial Sequence
<220> FEATURE:
<223> OTHER INFORMATION: nanobody

<400> SEQUENCE: 23

His Tyr Gln Gly Ser Tyr Gly Ser Ala Leu Ala 1 5 10

<210> SEQ ID NO 24
<211> LENGTH: 123
<212> TYPE: PRT
<213> ORGANISM: Artificial Sequence
<220> FEATURE:
<223> OTHER INFORMATION: nanobody

<400> SEQUENCE: 24

Gln Val Gln Leu Gln Glu Ser Gly Gly Gly Leu Val Gln Ala Gly Gly
1 5 10 15

Ser Leu Arg Leu Ser Cys Ala Ala Ser Glu Arg Thr Phe Ser Arg Tyr
20 25 30

Ala Met Gly Trp Phe Arg Gln Ala Pro Glu Lys Glu Arg Glu Phe Val
35 40 45

Ala Ala Ile Asn Trp Ser Gly Ser Ser Thr Tyr Tyr Ala Asp Ser Val
50 55 60

Lys Gly Arg Phe Thr Val Ser Arg Asp Asp Ala Lys Asn Thr Val Tyr
65 70 75 80

Leu Gln Met Asn Ser Leu Lys Pro Glu Asp Thr Ala Val Tyr Tyr Cys
85 90 95

Ala Ala His Tyr Gln Gly Ser Tyr Gly Ser Ala Leu Ala Tyr Asp Thr
100 105 110

Trp Gly Gln Gly Thr Gln Val Thr Val Ser Ser
115 120

<210> SEQ ID NO 25
<211> LENGTH: 9
<212> TYPE: PRT
<213> ORGANISM: Artificial Sequence
<220> FEATURE:
<223> OTHER INFORMATION: nanobody

<400> SEQUENCE: 25

Ser Gly Arg Thr Phe Ser Arg Asn Ala
1 5

<210> SEQ ID NO 26
<211> LENGTH: 7
<212> TYPE: PRT
<213> ORGANISM: Artificial Sequence
<220> FEATURE:
<223> OTHER INFORMATION: nanobody

<400> SEQUENCE: 26

Ile Ser Trp Ser Gly Arg Asn
1 5

<210> SEQ ID NO 27
<211> LENGTH: 21
<212> TYPE: PRT
<213> ORGANISM: Artificial Sequence
<220> FEATURE:
<223> OTHER INFORMATION: nanobody

<400> SEQUENCE: 27

Val Gly Ala Asp Trp Arg Val Tyr Asp Glu Ser Tyr Tyr Ser Thr Ala
1 5 10 15

His Tyr Tyr Glu Tyr
20

<210> SEQ ID NO 28
<211> LENGTH: 129
<212> TYPE: PRT
<213> ORGANISM: Artificial Sequence
<220> FEATURE:
<223> OTHER INFORMATION: nanobody

<400> SEQUENCE: 28

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Arg Thr Phe Ser Arg Asn
            20                  25                  30

Ala Met Gly Trp Phe Arg Gln Ala Pro Gly Lys Glu Arg Glu Phe Val
        35                  40                  45

Ala Ala Ile Ser Trp Ser Gly Arg Asn Thr Tyr Tyr Ala Asp Ser Val
    50                  55                  60

Lys Gly Arg Phe Thr Ile Ser Arg Asp Asn Ala Lys Asn Thr Leu Ser
65                  70                  75                  80

Leu Gln Met Asn Ser Leu Lys Pro Glu Asp Ser Ala Val Tyr Ile Cys
                85                  90                  95

Ala Val Gly Ala Asp Trp Arg Val Tyr Asp Glu Ser Tyr Tyr Ser Thr
            100                 105                 110

Ala His Tyr Tyr Glu Tyr Trp Gly Gln Gly Thr Gln Val Thr Val Ser
        115                 120                 125

Ser
```

<210> SEQ ID NO 29
<211> LENGTH: 9
<212> TYPE: PRT
<213> ORGANISM: Artificial Sequence
<220> FEATURE:
<223> OTHER INFORMATION: nanobody

<400> SEQUENCE: 29

```
Ser Gly Arg Thr Phe Ser Ser Tyr Ala
1               5
```

<210> SEQ ID NO 30
<211> LENGTH: 10
<212> TYPE: PRT
<213> ORGANISM: Artificial Sequence
<220> FEATURE:
<223> OTHER INFORMATION: nanobody

<400> SEQUENCE: 30

```
Ile Glu Arg Ser Gly Gly Thr Ala Ser His
1               5                   10
```

<210> SEQ ID NO 31
<211> LENGTH: 10
<212> TYPE: PRT
<213> ORGANISM: Artificial Sequence
<220> FEATURE:
<223> OTHER INFORMATION: nanobody

<400> SEQUENCE: 31

```
Ser Ser Tyr Trp Ser Arg Ser Val Asp Glu
1               5                   10
```

<210> SEQ ID NO 32
<211> LENGTH: 122
<212> TYPE: PRT
<213> ORGANISM: Artificial Sequence

```
<220> FEATURE:
<223> OTHER INFORMATION: nanobody

<400> SEQUENCE: 32

Gln Val Gln Leu Gln Glu Ser Gly Gly Gly Leu Val Gln Gly Gly Gly
1               5                   10                  15

Ser Arg Arg Phe Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Glu Arg Ser Gly Gly Thr Ala Ser His Ala Asp Ser Lys
    50                  55                  60

Lys Gly Arg Phe Thr Ile Ser Arg Asp Asn Thr Lys Asn Thr Val Tyr
65                  70                  75                  80

Gln Gln Met Asn Ser Lys Lys Pro Glu Asp Thr Ala Val Tyr Tyr Cys
                85                  90                  95

Ala Ala Ser Ser Tyr Trp Ser Arg Ser Val Asp Glu Tyr Asp Tyr Trp
            100                 105                 110

Gly Gln Gly Thr Gln Val Thr Val Ser Ser
        115                 120


<210> SEQ ID NO 33
<211> LENGTH: 9
<212> TYPE: PRT
<213> ORGANISM: Artificial Sequence
<220> FEATURE:
<223> OTHER INFORMATION: nanobody

<400> SEQUENCE: 33

Ser Glu Arg Thr Phe Ser Arg Tyr Ala
1               5


<210> SEQ ID NO 34
<211> LENGTH: 7
<212> TYPE: PRT
<213> ORGANISM: Artificial Sequence
<220> FEATURE:
<223> OTHER INFORMATION: nanobody

<400> SEQUENCE: 34

Ile Asn Trp Ser Gly Ser Ser
1               5


<210> SEQ ID NO 35
<211> LENGTH: 11
<212> TYPE: PRT
<213> ORGANISM: Artificial Sequence
<220> FEATURE:
<223> OTHER INFORMATION: nanobody

<400> SEQUENCE: 35

His Tyr Gln Gly Ser Tyr Gly Ser Ala Ser Ala
1               5                   10


<210> SEQ ID NO 36
<211> LENGTH: 123
<212> TYPE: PRT
<213> ORGANISM: Artificial Sequence
<220> FEATURE:
<223> OTHER INFORMATION: nanobody

<400> SEQUENCE: 36

Gln Val Gln Leu Gln Glu Ser Gly Gly Gly Leu Val Gln Ala Gly Gly
```

```
1               5                   10                  15

Ser Leu Arg Leu Ser Cys Ala Ala Ser Glu Arg Thr Phe Ser Arg Tyr
            20                  25                  30

Ala Met Gly Trp Phe Arg Gln Ala Pro Glu Lys Glu Arg Glu Phe Val
        35                  40                  45

Ala Ala Ile Asn Trp Ser Gly Ser Ser Thr Tyr Tyr Ala Asp Ser Val
    50                  55                  60

Lys Gly Arg Phe Thr Val Ser Arg Asp Asp Ala Lys Asn Thr Val Asn
65                  70                  75                  80

Leu Glu Met Asn Ser Leu Lys Pro Glu Asp Thr Ala Val Tyr Tyr Cys
                85                  90                  95

Ala Ala His Tyr Gln Gly Ser Tyr Gly Ser Ala Ser Ala Tyr Asp Thr
            100                 105                 110

Trp Gly Gln Gly Thr Gln Val Thr Val Ser Ser
        115                 120


<210> SEQ ID NO 37
<211> LENGTH: 9
<212> TYPE: PRT
<213> ORGANISM: Artificial Sequence
<220> FEATURE:
<223> OTHER INFORMATION: nanobody

<400> SEQUENCE: 37

Ser Gly Arg Thr Phe Ser Pro Tyr Ala
1               5


<210> SEQ ID NO 38
<211> LENGTH: 7
<212> TYPE: PRT
<213> ORGANISM: Artificial Sequence
<220> FEATURE:
<223> OTHER INFORMATION: nanobody

<400> SEQUENCE: 38

Ile Thr Trp Ser Gly Gly Leu
1               5


<210> SEQ ID NO 39
<211> LENGTH: 15
<212> TYPE: PRT
<213> ORGANISM: Artificial Sequence
<220> FEATURE:
<223> OTHER INFORMATION: nanobody

<400> SEQUENCE: 39

Cys Ala Leu Asp Asp Asp Thr Phe Gly Val Thr Thr Ser Thr His
1               5                   10                  15


<210> SEQ ID NO 40
<211> LENGTH: 124
<212> TYPE: PRT
<213> ORGANISM: Artificial Sequence
<220> FEATURE:
<223> OTHER INFORMATION: nanobody

<400> SEQUENCE: 40

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Pro Tyr
            20                  25                  30

Ala Met Gly Trp Phe Arg Gln Ala Pro Gly Lys Glu Arg Glu Phe Val
```

35 40 45

Ala Ala Ile Thr Trp Ser Gly Gly Leu Thr Tyr Tyr Ala Asp Ser Val
50 55 60

Lys Gly Arg Phe Thr Ile Ser Arg Asp Asn Ser Lys Asn Thr Val Ser
65 70 75 80

Leu Gln Met Asn Ser Leu Lys Pro Glu Asp Thr Ala Val Tyr Tyr Cys
85 90 95

Ala Leu Asp Asp Asp Thr Phe Gly Val Thr Thr Ser Thr His Tyr Asp
100 105 110

Tyr Trp Gly Gln Gly Thr Gln Val Thr Val Ser Ser
115 120

<210> SEQ ID NO 41
<211> LENGTH: 9
<212> TYPE: PRT
<213> ORGANISM: Artificial Sequence
<220> FEATURE:
<223> OTHER INFORMATION: nanobody

<400> SEQUENCE: 41

Ser Gly Arg Thr Phe Ser Lys Asn Ala
1 5

<210> SEQ ID NO 42
<211> LENGTH: 9
<212> TYPE: PRT
<213> ORGANISM: Artificial Sequence
<220> FEATURE:
<223> OTHER INFORMATION: nanobody

<400> SEQUENCE: 42

Val Ala Ile Ser Trp Ser Gly Arg Asn
1 5

<210> SEQ ID NO 43
<211> LENGTH: 22
<212> TYPE: PRT
<213> ORGANISM: Artificial Sequence
<220> FEATURE:
<223> OTHER INFORMATION: nanobody

<400> SEQUENCE: 43

Cys Ala Val Gly Gly Asp Trp Arg Val Tyr Asp Ile Ser Phe Tyr Tyr
1 5 10 15

Thr Ala His Gln Tyr Glu
20

<210> SEQ ID NO 44
<211> LENGTH: 129
<212> TYPE: PRT
<213> ORGANISM: Artificial Sequence
<220> FEATURE:
<223> OTHER INFORMATION: nanobody

<400> SEQUENCE: 44

Gln Val Gln Leu Gln Glu Ser Gly Gly Gly Ser Val Gln Ala Gly Gly
1 5 10 15

Ser Leu Arg Leu Ser Cys Ala Ala Ser Gly Arg Thr Phe Ser Lys Asn
20 25 30

Ala Met Gly Trp Phe Arg Gln Ala Pro Gly Lys Glu Arg Glu Phe Val
35 40 45

Val Ala Ile Ser Trp Ser Gly Arg Asn Thr Tyr Tyr Ala Asp Ser Val

```
    50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Ser Ala Val Tyr Tyr Cys
                85                  90                  95

Ala Val Gly Gly Asp Trp Arg Val Tyr Asp Ile Ser Phe Tyr Tyr Thr
            100                 105                 110

Ala His Gln Tyr Glu Tyr Trp Gly Gln Gly Thr Gln Val Thr Val Ser
        115                 120                 125

Ser


<210> SEQ ID NO 45
<211> LENGTH: 9
<212> TYPE: PRT
<213> ORGANISM: Artificial Sequence
<220> FEATURE:
<223> OTHER INFORMATION: nanobody

<400> SEQUENCE: 45

Ser Leu Gly Thr Phe Ser Arg Tyr Ala
1               5


<210> SEQ ID NO 46
<211> LENGTH: 13
<212> TYPE: PRT
<213> ORGANISM: Artificial Sequence
<220> FEATURE:
<223> OTHER INFORMATION: nanobody

<400> SEQUENCE: 46

Val Ser Ala Ile Ser Trp Ser Gly Gly Ser Thr Leu Tyr
1               5                   10


<210> SEQ ID NO 47
<211> LENGTH: 18
<212> TYPE: PRT
<213> ORGANISM: Artificial Sequence
<220> FEATURE:
<223> OTHER INFORMATION: nanobody

<400> SEQUENCE: 47

Glu Val Phe Tyr Ser Gly Ser Tyr Asp Asp Thr Leu Arg Val Gln Ser
1               5                   10                  15

His Glu


<210> SEQ ID NO 48
<211> LENGTH: 130
<212> TYPE: PRT
<213> ORGANISM: Artificial Sequence
<220> FEATURE:
<223> OTHER INFORMATION: nanobody

<400> SEQUENCE: 48

Gln Val Gln Leu Gln Glu Ser Gly Gly Gly Leu Val Gln Ala Gly Gly
1               5                   10                  15

Ser Leu Arg Leu Ser Cys Ala Ala Ser Leu Gly Thr Phe Ser Arg Tyr
            20                  25                  30

Ala Met Gly Trp Phe Arg Gln Ala Pro Gly Lys Glu Arg Glu Phe Val
        35                  40                  45

Ser Ala Ile Ser Trp Ser Gly Gly Ser Thr Leu Tyr Ala Asp Ser Val
    50                  55                  60
```

Lys Gly Arg Phe Ala Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Glu Val Phe Tyr Ser Gly Ser Tyr Asp Asp Thr Leu Arg Val
100 105 110

Gln Ser His Glu Tyr Asp Tyr Trp Gly Gln Gly Thr Gln Val Thr Val
115 120 125

Ser Ser
130

<210> SEQ ID NO 49
<211> LENGTH: 9
<212> TYPE: PRT
<213> ORGANISM: Artificial Sequence
<220> FEATURE:
<223> OTHER INFORMATION: nanobody

<400> SEQUENCE: 49

Ser Gly Arg Thr Phe Ser Ser Tyr Thr
1 5

<210> SEQ ID NO 50
<211> LENGTH: 7
<212> TYPE: PRT
<213> ORGANISM: Artificial Sequence
<220> FEATURE:
<223> OTHER INFORMATION: nanobody

<400> SEQUENCE: 50

Ile Ser Trp Ser Gly Gly Thr
1 5

<210> SEQ ID NO 51
<211> LENGTH: 11
<212> TYPE: PRT
<213> ORGANISM: Artificial Sequence
<220> FEATURE:
<223> OTHER INFORMATION: nanobody

<400> SEQUENCE: 51

Asp Thr Tyr Tyr Gly Ser Arg Met Trp Asn Glu
1 5 10

<210> SEQ ID NO 52
<211> LENGTH: 123
<212> TYPE: PRT
<213> ORGANISM: Artificial Sequence
<220> FEATURE:
<223> OTHER INFORMATION: nanobody

<400> SEQUENCE: 52

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Ser Tyr
20 25 30

Thr Met Gly Trp Phe Arg Gln Ala Pro Gly Lys Glu Arg Glu Phe Val
35 40 45

Ala Ala Ile Ser Trp Ser Gly Gly Thr Thr Tyr Tyr Ala Asp Ser Val
50 55 60

Lys Gly Arg Phe Ala Ile Ala Arg Asp Asn Ala Lys Asn Thr Ala Tyr
65 70 75 80

```
Leu Gln Met Asn Ser Leu Lys Pro Glu Asp Thr Ala Val Tyr Tyr Cys
                85                  90                  95

Ala Ala Asp Thr Tyr Tyr Gly Ser Arg Met Trp Asn Glu Tyr Asp Tyr
            100                 105                 110

Trp Gly Gln Gly Thr Gln Val Thr Val Ser Ser
        115                 120


<210> SEQ ID NO 53
<211> LENGTH: 9
<212> TYPE: PRT
<213> ORGANISM: Artificial Sequence
<220> FEATURE:
<223> OTHER INFORMATION: nanobody

<400> SEQUENCE: 53

Ser Glu Arg Thr Phe Ser Arg Tyr Ala
1               5


<210> SEQ ID NO 54
<211> LENGTH: 7
<212> TYPE: PRT
<213> ORGANISM: Artificial Sequence
<220> FEATURE:
<223> OTHER INFORMATION: nanobody

<400> SEQUENCE: 54

Ile Asn Trp Ser Gly Ser Ser
1               5


<210> SEQ ID NO 55
<211> LENGTH: 72
<212> TYPE: PRT
<213> ORGANISM: Artificial Sequence
<220> FEATURE:
<223> OTHER INFORMATION: nanobody

<400> SEQUENCE: 55

Gln Val Gln Leu Gln Glu Ser Gly Gly Gly Leu Val Gln Ala Gly Gly
1               5                   10                  15

Ser Leu Arg Leu Ser Cys Ala Ala Ser Glu Arg Thr Phe Ser Arg Tyr
            20                  25                  30

Ala Met Gly Trp Phe Arg Gln Ala Pro Glu Lys Glu Arg Glu Phe Val
        35                  40                  45

Ala Ala Ile Asn Trp Ser Gly Ser Ser Thr Tyr Tyr Ala Asp Ser Val
    50                  55                  60

Lys Gly Arg Phe Thr Val Ser Ser
65                  70


<210> SEQ ID NO 56
<211> LENGTH: 9
<212> TYPE: PRT
<213> ORGANISM: Artificial Sequence
<220> FEATURE:
<223> OTHER INFORMATION: nanobody

<400> SEQUENCE: 56

Ser Gly Arg Thr Phe Ser Arg Asn Ala
1               5


<210> SEQ ID NO 57
<211> LENGTH: 7
<212> TYPE: PRT
<213> ORGANISM: Artificial Sequence
<220> FEATURE:
```

<223> OTHER INFORMATION: nanobody

<400> SEQUENCE: 57

Ile Asn Trp Ser Gly Ser Ser
1 5

<210> SEQ ID NO 58
<211> LENGTH: 72
<212> TYPE: PRT
<213> ORGANISM: Artificial Sequence
<220> FEATURE:
<223> OTHER INFORMATION: nanobody

<400> SEQUENCE: 58

Gln Val Gln Leu Gln Glu Ser Gly Gly Gly Ser Val Gln Ala Gly Gly
1 5 10 15

Ser Leu Arg Leu Ser Cys Ala Ala Ser Gly Arg Thr Phe Ser Arg Asn
20 25 30

Ala Met Gly Trp Phe Arg Gln Ala Pro Gly Lys Glu Arg Glu Phe Val
35 40 45

Ala Ala Ile Asn Trp Ser Gly Ser Ser Thr Tyr Tyr Ala Asp Ser Val
50 55 60

Lys Gly Arg Phe Thr Val Ser Ser
65 70

<210> SEQ ID NO 59
<211> LENGTH: 9
<212> TYPE: PRT
<213> ORGANISM: Artificial Sequence
<220> FEATURE:
<223> OTHER INFORMATION: nanobody

<400> SEQUENCE: 59

Ser Glu Arg Thr Phe Ser Arg Tyr Ala
1 5

<210> SEQ ID NO 60
<211> LENGTH: 7
<212> TYPE: PRT
<213> ORGANISM: Artificial Sequence
<220> FEATURE:
<223> OTHER INFORMATION: nanobody

<400> SEQUENCE: 60

Ile Asn Trp Ser Gly Ser Ser
1 5

<210> SEQ ID NO 61
<211> LENGTH: 11
<212> TYPE: PRT
<213> ORGANISM: Artificial Sequence
<220> FEATURE:
<223> OTHER INFORMATION: nanobody

<400> SEQUENCE: 61

His Tyr Gln Gly Ser Tyr Gly Ser Ala Ser Ala
1 5 10

<210> SEQ ID NO 62
<211> LENGTH: 123
<212> TYPE: PRT
<213> ORGANISM: Artificial Sequence
<220> FEATURE:
<223> OTHER INFORMATION: nanobody

<400> SEQUENCE: 62

Gln Val Gln Leu Gln Glu Ser Gly Gly Gly Leu Val Gln Ala Gly Gly
1               5                   10                  15

Ser Leu Arg Leu Ser Cys Ala Ala Ser Glu Arg Thr Phe Ser Arg Tyr
            20                  25                  30

Ala Met Gly Trp Phe Arg Gln Ala Pro Glu Lys Glu Arg Glu Phe Val
        35                  40                  45

Ala Ala Ile Asn Trp Ser Gly Ser Ser Thr Tyr Tyr Ala Asp Ser Val
    50                  55                  60

Lys Gly Arg Phe Thr Val Ser Arg Asp Asp Ala Lys Asn Thr Val Asn
65                  70                  75                  80

Leu Glu Met Asn Ser Leu Lys Pro Glu Asp Thr Ala Val Tyr Tyr Cys
                85                  90                  95

Ala Ala His Tyr Gln Gly Ser Tyr Gly Ser Ala Ser Ala Tyr Asp Thr
            100                 105                 110

Trp Gly Gln Gly Thr Gln Val Thr Val Ser Ser
        115                 120

<210> SEQ ID NO 63
<211> LENGTH: 11
<212> TYPE: PRT
<213> ORGANISM: Artificial Sequence
<220> FEATURE:
<223> OTHER INFORMATION: nanobody

<400> SEQUENCE: 63

Ser Gly Phe Ser Phe Asp Asp Tyr Thr Leu Gly
1               5                   10

<210> SEQ ID NO 64
<211> LENGTH: 10
<212> TYPE: PRT
<213> ORGANISM: Artificial Sequence
<220> FEATURE:
<223> OTHER INFORMATION: nanobody

<400> SEQUENCE: 64

Val Ser Cys Ile Ser Ser Ser Asp Gly Ser
1               5                   10

<210> SEQ ID NO 65
<211> LENGTH: 22
<212> TYPE: PRT
<213> ORGANISM: Artificial Sequence
<220> FEATURE:
<223> OTHER INFORMATION: nanobody

<400> SEQUENCE: 65

Val Val Gly Leu Arg Leu Pro Thr Tyr Ala Ser Asn Ser Cys Lys Ile
1               5                   10                  15

Val Ala Asp Phe Gly Ser
            20

<210> SEQ ID NO 66
<211> LENGTH: 131
<212> TYPE: PRT
<213> ORGANISM: Artificial Sequence
<220> FEATURE:
<223> OTHER INFORMATION: nanobody

<400> SEQUENCE: 66

Gln Val Gln Leu Gln Glu Ser Gly Gly Gly Leu Val Gln Ala Gly Gly

-continued

```
1               5                   10                  15

Ser Leu Arg Leu Ser Cys Ala Ala Ser Gly Phe Ser Phe Asp Asp Tyr
            20                  25                  30

Thr Leu Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Ser Gly Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Val Gly Leu Arg Leu Pro Thr Tyr Ala Ser Asn Ser Cys
            100                 105                 110

Lys Ile Val Ala Asp Phe Gly Ser Trp Gly Gln Gly Thr Gln Val Thr
        115                 120                 125

Val Ser Ser
    130


<210> SEQ ID NO 67
<211> LENGTH: 11
<212> TYPE: PRT
<213> ORGANISM: Artificial Sequence
<220> FEATURE:
<223> OTHER INFORMATION: nanobody

<400> SEQUENCE: 67

Val Ala Ser Gly Arg Thr Phe Ser Ser Tyr Ala
1               5                   10


<210> SEQ ID NO 68
<211> LENGTH: 10
<212> TYPE: PRT
<213> ORGANISM: Artificial Sequence
<220> FEATURE:
<223> OTHER INFORMATION: nanobody

<400> SEQUENCE: 68

Ile Asp Trp Ser Gly Gly Thr Ala Ser His
1               5                   10


<210> SEQ ID NO 69
<211> LENGTH: 22
<212> TYPE: PRT
<213> ORGANISM: Artificial Sequence
<220> FEATURE:
<223> OTHER INFORMATION: nanobody

<400> SEQUENCE: 69

Cys Ala Val Gly Gly Asp Trp Arg Val Tyr Asp Ile Ser Phe Tyr Tyr
1               5                   10                  15

Thr Ala His Gln Tyr Glu
            20


<210> SEQ ID NO 70
<211> LENGTH: 129
<212> TYPE: PRT
<213> ORGANISM: Artificial Sequence
<220> FEATURE:
<223> OTHER INFORMATION: nanobody

<400> SEQUENCE: 70

Gln Val Gln Leu Gln Glu Ser Gly Gly Gly Leu Val Gln Ala Gly Gly
```

1 5 10 15

Ser Leu Arg Leu Ser Cys Val Ala Ser Gly Arg Thr Phe Ser Ser Tyr
20 25 30

Ala Met Gly Trp Phe Arg Gln Ala Pro Gly Lys Glu Arg Glu Phe Val
35 40 45

Ala Ala Ile Asp Trp Ser Gly Gly Thr Ala Ser His Ala Asp Ser Val
50 55 60

Lys Gly Arg Phe Thr Ile Ser Arg Asp Asn Ala Lys Asn Thr Val Asp
65 70 75 80

Leu Gln Met Asn Ser Leu Lys Pro Glu Asp Ser Ala Val Tyr Tyr Cys
85 90 95

Ala Val Gly Gly Asp Trp Arg Val Tyr Asp Ile Ser Phe Tyr Tyr Thr
100 105 110

Ala His Gln Tyr Glu Tyr Trp Gly Gln Gly Thr Gln Val Thr Val Ser
115 120 125

Ser

<210> SEQ ID NO 71
<211> LENGTH: 9
<212> TYPE: PRT
<213> ORGANISM: Artificial Sequence
<220> FEATURE:
<223> OTHER INFORMATION: nanobody

<400> SEQUENCE: 71

Ser Gly Arg Thr Phe Ser Arg Asn Ala
1 5

<210> SEQ ID NO 72
<211> LENGTH: 7
<212> TYPE: PRT
<213> ORGANISM: Artificial Sequence
<220> FEATURE:
<223> OTHER INFORMATION: nanobody

<400> SEQUENCE: 72

Ile Ser Trp Ser Gly Arg Asn
1 5

<210> SEQ ID NO 73
<211> LENGTH: 11
<212> TYPE: PRT
<213> ORGANISM: Artificial Sequence
<220> FEATURE:
<223> OTHER INFORMATION: nanobody

<400> SEQUENCE: 73

His Tyr Gln Gly Ser Tyr Gly Ser Ala Leu Ala
1 5 10

<210> SEQ ID NO 74
<211> LENGTH: 123
<212> TYPE: PRT
<213> ORGANISM: Artificial Sequence
<220> FEATURE:
<223> OTHER INFORMATION: nanobody

<400> SEQUENCE: 74

Gln Val Gln Leu Gln Glu Ser Gly Gly Gly Ser Val Gln Ala Gly Gly
1 5 10 15

Ser Leu Arg Leu Ser Cys Ala Ala Ser Gly Arg Thr Phe Ser Arg Asn
20 25 30

```
Ala Met Gly Trp Phe Arg Gln Ala Pro Gly Lys Glu Arg Glu Phe Val
        35                  40                  45

Ala Ala Ile Ser Trp Ser Gly Arg Asn Thr Tyr Tyr Ala Asp Ser Val
    50                  55                  60

Lys Gly Arg Phe Thr Val Ser Arg Asp Asp Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Tyr Gln Gly Ser Tyr Gly Ser Ala Leu Ala Tyr Asp Thr
            100                 105                 110

Trp Gly Gln Gly Thr Gln Val Thr Val Ser Ser
        115                 120


<210> SEQ ID NO 75
<211> LENGTH: 9
<212> TYPE: PRT
<213> ORGANISM: Artificial Sequence
<220> FEATURE:
<223> OTHER INFORMATION: nanobody

<400> SEQUENCE: 75

Ser Gly Arg Thr Phe Ser Asn Phe Ala
1               5


<210> SEQ ID NO 76
<211> LENGTH: 7
<212> TYPE: PRT
<213> ORGANISM: Artificial Sequence
<220> FEATURE:
<223> OTHER INFORMATION: nanobody

<400> SEQUENCE: 76

Ile Thr Trp Ser Arg Gly Ser
1               5


<210> SEQ ID NO 77
<211> LENGTH: 16
<212> TYPE: PRT
<213> ORGANISM: Artificial Sequence
<220> FEATURE:
<223> OTHER INFORMATION: nanobody

<400> SEQUENCE: 77

Gly Leu Trp Arg Tyr Tyr Thr Glu Ser Tyr Phe Tyr Thr Glu Asp Arg
1               5                   10                  15


<210> SEQ ID NO 78
<211> LENGTH: 128
<212> TYPE: PRT
<213> ORGANISM: Artificial Sequence
<220> FEATURE:
<223> OTHER INFORMATION: nanobody

<400> SEQUENCE: 78

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Phe
            20                  25                  30

Ala Met Gly Trp Phe Arg Gln Ala Pro Gly Lys Glu Arg Glu Phe Val
        35                  40                  45

Ala Ala Ile Thr Trp Ser Arg Gly Ser Thr Tyr Tyr Thr Asp Ser Val
    50                  55                  60
```

Lys Gly Arg Phe Thr Ile Ser Arg Asp Asn Ala Lys Asn Thr Gly Tyr
65 70 75 80

Leu Gln Met Asn Ser Leu Lys Pro Glu Asp Ser Ala Val Tyr Tyr Cys
85 90 95

Ala Ala Gly Leu Trp Arg Tyr Tyr Thr Glu Ser Tyr Phe Tyr Thr Glu
100 105 110

Asp Arg Tyr Asp Tyr Trp Gly Gln Gly Thr Gln Val Thr Val Ser Ser
115 120 125

<210> SEQ ID NO 79
<211> LENGTH: 12
<212> TYPE: PRT
<213> ORGANISM: Artificial Sequence
<220> FEATURE:
<223> OTHER INFORMATION: nanobody

<400> SEQUENCE: 79

Ala Val Ser Gly Phe Thr Leu Asp Asn Tyr Ala Ile
1 5 10

<210> SEQ ID NO 80
<211> LENGTH: 10
<212> TYPE: PRT
<213> ORGANISM: Artificial Sequence
<220> FEATURE:
<223> OTHER INFORMATION: nanobody

<400> SEQUENCE: 80

Val Ser Cys Ile Ser Ser Ser Asp Gly Ser
1 5 10

<210> SEQ ID NO 81
<211> LENGTH: 19
<212> TYPE: PRT
<213> ORGANISM: Artificial Sequence
<220> FEATURE:
<223> OTHER INFORMATION: nanobody

<400> SEQUENCE: 81

Thr His Glu Gln Val Trp Lys Thr Leu Phe Ser Ser Cys Thr Val Glu
1 5 10 15

Arg Asp Asp

<210> SEQ ID NO 82
<211> LENGTH: 130
<212> TYPE: PRT
<213> ORGANISM: Artificial Sequence
<220> FEATURE:
<223> OTHER INFORMATION: nanobody

<400> SEQUENCE: 82

Gln Val Gln Leu Gln Glu Ser Gly Gly Gly Leu Val Gln Pro Gly Gly
1 5 10 15

Ser Leu Arg Leu Ser Cys Ala Val Ser Gly Phe Thr Leu Asp Asn Tyr
20 25 30

Ala Ile Gly Trp Phe Arg Gln Ala Pro Gly Lys Glu Arg Glu Gly Val
35 40 45

Ser Cys Ile Ser Ser Ser Asp Gly Ser Thr Tyr Tyr Ala Asp Ser Val
50 55 60

Lys Gly Arg Phe Thr Ile Ser Ser Asp Asn Asp Lys Asn Met Val Tyr
65 70 75 80

```
Leu Gln Met Asn Ser Leu Lys Pro Glu Asp Thr Ala Val Tyr Tyr Cys
                85                  90                  95

Ala Thr His Glu Gln Val Trp Lys Thr Leu Phe Ser Ser Cys Thr Val
            100                 105                 110

Glu Arg Asp Asp Tyr Asp Tyr Trp Gly Gln Gly Thr Gln Val Thr Val
        115                 120                 125

Ser Ser
    130


<210> SEQ ID NO 83
<211> LENGTH: 11
<212> TYPE: PRT
<213> ORGANISM: Artificial Sequence
<220> FEATURE:
<223> OTHER INFORMATION: nanobody

<400> SEQUENCE: 83

Val Ala Ser Gly Arg Thr Phe Ser Ser Tyr Ala
1               5                   10


<210> SEQ ID NO 84
<211> LENGTH: 10
<212> TYPE: PRT
<213> ORGANISM: Artificial Sequence
<220> FEATURE:
<223> OTHER INFORMATION: nanobody

<400> SEQUENCE: 84

Ile Asp Trp Ser Gly Gly Thr Ala Ser His
1               5                   10


<210> SEQ ID NO 85
<211> LENGTH: 10
<212> TYPE: PRT
<213> ORGANISM: Artificial Sequence
<220> FEATURE:
<223> OTHER INFORMATION: nanobody

<400> SEQUENCE: 85

Ser Ser Tyr Trp Ser Arg Ser Val Asp Glu
1               5                   10


<210> SEQ ID NO 86
<211> LENGTH: 122
<212> TYPE: PRT
<213> ORGANISM: Artificial Sequence
<220> FEATURE:
<223> OTHER INFORMATION: nanobody

<400> SEQUENCE: 86

Gln Val Gln Leu Gln Glu Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Asp Trp Ser Gly Gly Thr Ala Ser His Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95
```

```
Ala Ala Ser Ser Tyr Trp Ser Arg Ser Val Asp Glu Tyr Asp Tyr Trp
            100                 105                 110

Gly Gln Gly Thr Gln Val Thr Val Ser Ser
        115                 120


<210> SEQ ID NO 87
<211> LENGTH: 11
<212> TYPE: PRT
<213> ORGANISM: Artificial Sequence
<220> FEATURE:
<223> OTHER INFORMATION: nanobody

<400> SEQUENCE: 87

Ser Gly Phe Thr Leu Asp Asn Tyr Ala Ile Gly
1               5                   10


<210> SEQ ID NO 88
<211> LENGTH: 10
<212> TYPE: PRT
<213> ORGANISM: Artificial Sequence
<220> FEATURE:
<223> OTHER INFORMATION: nanobody

<400> SEQUENCE: 88

Val Ser Cys Ile Ser Ser Ser Asp Gly Ser
1               5                   10


<210> SEQ ID NO 89
<211> LENGTH: 19
<212> TYPE: PRT
<213> ORGANISM: Artificial Sequence
<220> FEATURE:
<223> OTHER INFORMATION: nanobody

<400> SEQUENCE: 89

Thr His Glu Gln Val Trp Lys Thr Leu Phe Ser Ser Cys Thr Val Glu
1               5                   10                  15

Arg Asp Asp


<210> SEQ ID NO 90
<211> LENGTH: 130
<212> TYPE: PRT
<213> ORGANISM: Artificial Sequence
<220> FEATURE:
<223> OTHER INFORMATION: nanobody

<400> SEQUENCE: 90

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Asn Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Ala Tyr
65                  70                  75                  80

Leu Gln Leu Asn Ser Leu Lys Pro Glu Asp Thr Ala Val Tyr Tyr Cys
                85                  90                  95

Ala Thr His Glu Gln Val Trp Lys Thr Leu Phe Ser Ser Cys Thr Val
            100                 105                 110

Glu Arg Asp Asp Tyr Asp Tyr Trp Gly Gln Gly Thr Gln Val Thr Val
```

```
        115                 120                 125

Ser Ser
    130


<210> SEQ ID NO 91
<211> LENGTH: 11
<212> TYPE: PRT
<213> ORGANISM: Artificial Sequence
<220> FEATURE:
<223> OTHER INFORMATION: nanobody

<400> SEQUENCE: 91

Ser Gly Phe Thr Leu Asp Asn Tyr Ala Ile Gly
1               5                   10


<210> SEQ ID NO 92
<211> LENGTH: 10
<212> TYPE: PRT
<213> ORGANISM: Artificial Sequence
<220> FEATURE:
<223> OTHER INFORMATION: nanobody

<400> SEQUENCE: 92

Val Ser Cys Ile Ser Ser Ser Asp Gly Ser
1               5                   10


<210> SEQ ID NO 93
<211> LENGTH: 19
<212> TYPE: PRT
<213> ORGANISM: Artificial Sequence
<220> FEATURE:
<223> OTHER INFORMATION: nanobody

<400> SEQUENCE: 93

Thr His Glu Gln Val Trp Lys Thr Leu Phe Ser Ser Cys Thr Val Glu
1               5                   10                  15

Arg Asp Asp


<210> SEQ ID NO 94
<211> LENGTH: 130
<212> TYPE: PRT
<213> ORGANISM: Artificial Sequence
<220> FEATURE:
<223> OTHER INFORMATION: nanobody

<400> SEQUENCE: 94

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Leu Asp Asn Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Ala Tyr
65                  70                  75                  80

Leu Gln Leu Asn Ser Leu Lys Pro Glu Asp Thr Ala Val Tyr Tyr Cys
                85                  90                  95

Ala Thr His Glu Gln Val Trp Lys Thr Leu Phe Ser Ser Cys Thr Val
            100                 105                 110

Glu Arg Asp Asp Tyr Asp Tyr Trp Gly Gln Gly Thr Gln Val Thr Val
        115                 120                 125
```

Ser Ser
130

<210> SEQ ID NO 95
<211> LENGTH: 9
<212> TYPE: PRT
<213> ORGANISM: Artificial Sequence
<220> FEATURE:
<223> OTHER INFORMATION: nanobody

<400> SEQUENCE: 95

Ser Gly Arg Thr Phe Ser Ser Tyr Ala
1 5

<210> SEQ ID NO 96
<211> LENGTH: 10
<212> TYPE: PRT
<213> ORGANISM: Artificial Sequence
<220> FEATURE:
<223> OTHER INFORMATION: nanobody

<400> SEQUENCE: 96

Ile Asp Trp Ser Gly Gly Thr Ser Val His
1 5 10

<210> SEQ ID NO 97
<211> LENGTH: 10
<212> TYPE: PRT
<213> ORGANISM: Artificial Sequence
<220> FEATURE:
<223> OTHER INFORMATION: nanobody

<400> SEQUENCE: 97

Thr Ser Tyr Trp Ser Thr Ala Glu Tyr Glu
1 5 10

<210> SEQ ID NO 98
<211> LENGTH: 122
<212> TYPE: PRT
<213> ORGANISM: Artificial Sequence
<220> FEATURE:
<223> OTHER INFORMATION: nanobody

<400> SEQUENCE: 98

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Ser Tyr
20 25 30

Ala Met Gly Trp Phe Arg Gln Thr Pro Gly Lys Glu Arg Glu Phe Val
35 40 45

Ala Ala Ile Asp Trp Ser Gly Gly Thr Ser Val His Ala Asp Ser Val
50 55 60

Lys Gly Arg Phe Thr Ile Ala Arg Asp Asn Ala Lys Asn Thr Val Tyr
65 70 75 80

Leu Gln Met Ser Ser Leu Lys Pro Glu Asp Thr Ala Thr Tyr Tyr Cys
85 90 95

Ala Ala Thr Ser Tyr Trp Ser Thr Ala Glu Tyr Glu Tyr Asp Tyr Trp
100 105 110

Gly Gln Gly Thr Gln Val Thr Val Ser Ser
115 120

COMPOSITIONS AND METHODS FOR GENETICALLY-ENCODED HIGH VOLTAGE-ACTIVATED CALCIUM CHANNEL BLOCKERS USING ENGINEERED UBIQUITIN LIGASES

CROSS REFERENCE TO RELATED APPLICATIONS

The present application is a continuation of PCT international application no. PCT/US2020/025359, filed on Mar. 27, 2020, which claims benefit of U.S. Provisional Patent Application Ser. No. 62/886,733, filed on Aug. 14, 2019, U.S. Provisional Patent Application Ser. No. 62/883,637, filed on Aug. 6, 2019, U.S. Provisional Patent Application Ser. No. 62/854,688, filed on May 30, 2019, U.S. Provisional Patent Application Ser. No. 62/830,142, filed on Apr. 5, 2019, and U.S. Provisional Patent Application Ser. No. 62/825,784, filed on Mar. 28, 2019, which applications are incorporated by reference herein in their entireties.

GOVERNMENT FUNDING

This invention was made with government support under grant nos. GM107585, DK118866, and HL142111 awarded by the National Institutes of Health (NIH). The government has certain rights in the invention.

FIELD OF DISCLOSURE

The present disclosure provides, inter alia, genetically-encoded High-Voltage Activated Calcium Channel (HVACC) inhibitors including nanobodies targeting a $Ca_V\beta$ auxiliary subunit and compositions thereof. Also provided are treatment methods using the same.

INCORPORATION BY REFERENCE OF SEQUENCE LISTING

This application contains references to amino acids and/or nucleic acid sequences that have been filed concurrently herewith as sequence listing text file "CU19283-pro4-seq.txt", file size of 43 KB, created on Aug. 6, 2019. The aforementioned sequence listing is hereby incorporated by reference in its entirety pursuant to 37 C.F.R. § 1.52(e)(5).

BACKGROUND OF THE DISCLOSURE

High-Voltage Activated Calcium Channels (HVACCs) are critical for the function of excitable cells such as neurons. They permit the release of neurotransmitters, hormones, and initiate the contraction of both skeletal and cardiac muscle. As such, calcium channel blockers have been prominent drug targets for diseases as diverse as hypertension, cardiac arrhythmias, diabetes, Parkinson's disease, and chronic pain. The latter is estimated to affect 20% of the global population, with large economic and social consequences. Despite this large prevalence, current treatments for chronic pain remain inadequate, as exemplified with a common treatment for chronic pain that has led to an epidemic of opioids.

Among HVACCs, the N-type calcium channel is a primary target for the treatment of chronic pain. It is well established that these channels are expressed in the sensory neurons that transmit the sensation of pain, that blockade of these channels can disrupt pain perception, and that these channels are upregulated in multiple models of pain. An N-type calcium channel blocker derived from marine snail venom (Prialt) is currently used in limited situations for pain management, but is limited by a narrow therapeutic window. The therapeutic potential to decrease/inhibit HVACCs in particular tissues extends beyond pain: calcium channel blockers are currently in clinical trials for the treatment of diabetes as well as Parkinson's disease. All current drugs block the channel at its functional location, the plasma membrane, by disrupting its ability to permit calcium entry into the cell. Given their central importance in many cells, a primary concern with all current pharmacological HVACC blockers is off-target effects.

Most drugs against HVACCs target the pore-forming $\alpha_1$ subunit of the channel, disrupting the ability of the channel to permit calcium entry into the cell. HVACCs are also composed of auxiliary $\beta$ and $\alpha_2$-$\delta$ subunits which function to facilitate trafficking of the $\alpha_1$ subunit to the plasma membrane and fine-tune its properties once there. As critical regulators of channel function, these auxiliary subunits are potential therapeutic targets. Indeed, Gabapentin (Pregabalin or Lyrica), is used for treatment of chronic pain and works by downregulating N-type calcium channels via an association with the $\alpha_2$-$\delta$ subunit of the channel (the exact mechanism of how this occurs is under intense study). Gabapentin-based treatment produces fewer side effects compared to other treatment options such as opioids or tricyclic antidepressants, but full alleviation of pain is rare. Thus, there is a significant need for improved treatment options for this common condition. The auxiliary $\beta$ subunit is obligatory for proper channel trafficking. Yet, despite efforts to target the $\alpha_1$-$\beta$ binding interface, this subunit remains an untapped therapeutic target.

Currently, there is no genetically-encoded molecule or means to specifically block all HVACCs. Naturally occurring genetically-encoded inhibitors like RGK proteins bind other proteins and affect other cellular processes, such as regulating the cytoskeleton. This means that a cocktail of HVACC blockers, some of them expensive venom-derived peptides, must be co-administered.

Accordingly, there is a need for genetically-encoded HVACC inhibitors, as well as for compositions and methods for the treatment of various diseases associated with HVACCs. This disclosure is directed to meeting these and other needs.

SUMMARY OF THE DISCLOSURE

Inhibiting high-voltage-activated calcium channels (HVACCs, $Ca_V1/Ca_V2$) is therapeutic for myriad cardiovascular and neurological diseases. For particular applications, genetically-encoded HVACC blockers may enable channel inhibition with greater tissue-specificity and versatility than is achievable with small molecules. In the present disclosure, a genetically-encoded HVACC inhibitor was engineered by first isolating an immunized llama nanobody (nb.F3) that binds auxiliary HVACC $Ca_V\beta$ subunits. Nb.F3 by itself is functionally inert, providing a convenient vehicle to target active moieties to $Ca_V\beta$-associated channels. Nb.F3 fused to the catalytic HECT domain of Nedd4L ($Ca_V$-a$\beta$lator), an E3 ubiquitin ligase, ablated currents from diverse HVACCs reconstituted in HEK293 cells, and from endogenous $Ca_V1/Ca_V2$ channels in mammalian cardiomyocytes, dorsal root ganglion neurons, and pancreatic $\beta$ cells. In cardiomyocytes, $Ca_V$-a$\beta$lator redistributed $Ca_V1.2$ channels from dyads to Rab-7-positive late endosomes. The present disclosure introduces $Ca_V$-a$\beta$lator as a potent genetically-encoded HVACC inhibitor, and describes a general approach that can be broadly adapted to generate versatile modulators for macro-molecular membrane protein complexes.

Accordingly, one embodiment of the present disclosure is a nanobody capable of binding to a $Ca_V\beta$ auxiliary subunit, comprising SEQ ID NOs: 1-3, SEQ ID NOs: 5-7, SEQ ID NOs: 9-11, SEQ ID NOs: 13-15, SEQ ID NOs: 17-19, SEQ ID NOs: 21-23, SEQ ID NOs: 25-27, SEQ ID NOs: 29-31, SEQ ID NOs: 33-35, SEQ ID NOs: 37-39, SEQ ID NOs: 41-43, SEQ ID NOs: 45-47, SEQ ID NOs: 49-51, SEQ ID NOs: 53-54, SEQ ID NOs: 56-57, SEQ ID NOs: 59-61, SEQ ID NOs: 63-65, SEQ ID NOs: 67-69, SEQ ID NOs: 71-73, SEQ ID NOs: 75-77, SEQ ID NOs: 79-81, SEQ ID NOs: 83-85, SEQ ID NOs: 87-89, SEQ ID NOs: 91-93, or SEQ ID NOs: 95-97.

Another embodiment of the present disclosure is a composition comprising: (i) a nanobody as disclosed herein; and (ii) a catalytic domain of an E3 ubiquitin ligase operably connected to the nanobody.

Another embodiment of the present disclosure is a composition comprising a genetically encoded calcium channel blocker comprising a nucleic acid encoding: (i) a nanobody as disclosed herein; and (ii) a catalytic domain of an E3 ubiquitin ligase.

A further embodiment of the present disclosure is a method of blocking a High-Voltage Activated Calcium Channel (HVACC) in a cell, comprising contacting the cell with an effective amount of a composition as disclosed herein.

Another embodiment of the present disclosure is a method of selectively targeting a population of cells in a subject, comprising administering to the subject an effective amount of a composition as disclosed herein.

Another embodiment of the present disclosure is a composition for inducible inhibition of a High-Voltage Activated Calcium Channel (HVACC) in a cell comprising: (i) a nanobody as disclosed herein; and (ii) a C1 domain from protein kinase Cγ($C1_{PKC}$) operably connected to the nanobody; wherein the composition is effective to inactivate the HVACC after induction with phorbol-12,13-dibutyrate (PdBu).

An additional embodiment of the present disclosure is a composition comprising a genetically encoded inducible calcium channel blocker comprising a nucleic acid encoding: (i) a nanobody as disclosed herein; and (ii) a C1 domain from protein kinase Cγ($C1_{PKC}$) operably connected to the nanobody.

Another embodiment of the present disclosure is a method of blocking a High-Voltage Activated Calcium Channel (HVACC) in a cell, comprising the step of: (i) contacting the cell with an effective amount of a composition as disclosed herein; and (ii) contacting the cell with phorbol-12,13-dibutyrate (PdBu); wherein the contacting of steps (i) and (ii) are effective to remove the HVACC from its functional location on a plasma membrane of the cell.

Still another embodiment of the present disclosure is a method for treating or ameliorating the effects of a disease in a subject, comprising administering to the subject an effective amount of a composition as disclosed herein.

BRIEF DESCRIPTION OF THE DRAWINGS

The application file contains at least one drawing executed in color. Copies of this patent application with color drawing(s) will be provided by the Office upon request and payment of the necessary fee.

FIGS. 1A-1G show the development of a pan-$Ca_V\beta$ nanobody. FIG. 1A shows the size-exclusion chromatograph and Coomassie gel (inset) showing purified $Ca_v\beta_1$ from baculovirus-infected HEK293 GnTI$^-$ cells. FIG. 1B provides a representative flow-chart of nanobody generation according to the present disclosure. FIG. 1C shows a phage ELISA using $Ca_V\beta_1$ as bait and periplasmic extracts from single infected *E. coli* clones. Red bars represent clones that were selected for subsequent analyses; blue bar represents a negative control from an *E. coli* expressing an anti-GFP nanobody. FIG. 1D is a cartoon showing conventional IgG antibody (left) and camelid heavy-chain antibody (center). On the right is a schematic representation of the variable heavy chain (VHH or nanobody) of camelid heavy-chain antibodies. The three CDR loops which are the primary determinants of antigen-binding are shown in red, green, and blue. FIG. 1E shows the sequence alignment of CDR3 from selected clones. In FIG. 1F, on the left is a schematic of a co-translocation assay to determine nanobody/$Ca_V\beta$ interaction in HEK293 cells. On the right are the confocal images showing membrane co-translocation of $Ca_V\beta_X$-YFP and nb.F3-CFP-$C1_{PKC\gamma}$ in response to treatment with 1 μM of the phorbol ester, phorbol 12,13-dibutyrate (PdBu). In FIG. 1G, on the left shows an exemplar isothermal titration calorimetry trace using purified $Ca_V\beta_{2b}$ and nb.F3. On the Right shows a summary of ITC thermodynamic parameters. N, stoichiometry; $K_d$, dissociation constant; $K_a$, affinity constant; ΔH, enthalpic change; ΔS entropic change. T=298K.

FIG. 2A is a schematic of an experimental strategy according to the present disclosure in which BBS-$\alpha_{1B}$-YFP was transfected in HEK293 cells with $\alpha_2\delta$, $Ca_V\beta$ and either CFP or nb.F3-P2A-CFP. FIG. 2B shows a representative flow cytometry dot plot of cells expressing BBS-$\alpha_{1B}$-YFP+$Ca_V\beta_1$+$\alpha_2\delta$-1 and either CFP (left) or nb.F3-P2A-CFP (right). Approximately 100,000 cells are represented here and throughout. Horizontal and vertical lines represent the threshold for YFP- and Alexa-647-positive cells, respectively, as determined with single color controls. FIG. 2C shows the cumulative distribution histogram of Alexa-647 (left) or YFP fluorescence (right) from CFP (black) or nb.F3 (red) expressing cells. YFP-positive cells were selected for the analysis; dashed lines represent thresholds for Alexa-647 and YFP fluorescence signals above background. FIG. 2D shows a summary of flow cytometry data of surface (647, filled) and total (YFP, patterned) levels of BBS-$\alpha_{1B}$-YFP. Data from nb.F3-expressing cells was normalized to CFP control group. n=>5,000 cells analyzed per experiment, N=4 separate experiments, error bars, s.e.m. FIG. 2E shows a representative experimental strategy according to the present disclosure in which HEK293 cells were transfected with BBS-$\alpha_{1B}$+$Ca_V\beta$-YFP+$\alpha_2\delta$-1. FIGS. 2F-2H are in the same format as FIGS. 2B-2D for cells expressing BBS-$\alpha_{1B}$+$Ca_V\beta$-YFP+$\alpha_2\delta$-1±nb.F3-P2A-CFP. FIG. 2I shows representative whole-cell $Ba^{2+}$ currents (top) and population I-V curves (bottom) in HEK293 cells expressing $\alpha_{1B}$+$Ca_V\beta_1$+$\alpha_2\delta$-1 and either CFP (black) or nb.F3-P2A-CFP (red). FIGS. 2J-2L are in the same format as FIG. 2I for cells expressing $Ca_V\beta_2$ (FIG. 2J), $Ca_V\beta_3$ (FIG. 2K), and $Ca_V\beta_4$ (FIG. 2L). Scale bar 1 nA, 10 ms. Data are means±s.e.m., n=10 for each point.

FIG. 3A is a schematic of a representative experimental design according to the present disclosure in which HEK293 cells were transfected with BBS-$\alpha_{1B}$+$Ca_V\beta$-

YFP+$\alpha_2\delta$-1, and either nb.F3, nb.F3-Nedd4L, or nb.F3-Nedd4L[C942S]. FIG. 3B shows representative histograms (left) and summary data (right) of flow cytometry experiments measuring total (YFP) levels of $Ca_V\beta_{1b}$-YFP. Each data set was normalized to a control group that expressed CFP. n>5,000 cells analyzed per experiment, N=3 separate experiments, error bars, s.e.m. FIG. 3C shows representative histograms (left) and summary data (right) of flow cytometry experiments measuring surface (647) levels of BBS-$\alpha_{1B}$. The white dashed line is the threshold for 647 signal above background. FIG. 3D shows an experimental strategy according to the present disclosure, which has the same format as in FIG. 3A except YFP was fused to BBS-$\alpha_{1B}$, enabling measurement of the total levels of the $\alpha_{1B}$ subunit. FIGS. 3E-3F are in the same format as FIGS. 3B-3D for cells expressing BBS-$\alpha_{1B}$-YFP+$Ca_V\beta$+$\alpha_2\delta$-1. FIG. 3G shows representative traces (top) and population I-V curves (bottom) from whole-cell patch clamp measurements in HEK293 cells expressing $\alpha_{1B}$+$Ca_V\beta_{1b}$+$\alpha_2\delta$-1 and nb.F3 (black, $I_{peak,\ 0mV}$=−103.5±39.5 pA/pF, n=10), nb.F3-Nedd4L (red, $I_{peak,\ 0mV}$=−3±0.53 pA/pF, n=11), or nb.F3-Nedd4L[C942S] (green, $I_{peak,\ 0mV}$=−117±34.8 pA/pF, n=8). FIGS. 3H-3J are in the same format as FIG. 3G for $Ca_V2.2$ channels reconstituted with $Ca_V\beta_2$ (FIG. 3H), $Ca_V\beta_3$ (FIG. 3I), and $Ca_V\beta_4$ (FIG. 3J) with nb.F3 (black) or nb.F3-Nedd4L (red). Scale bar 1 nA, 10 ms. Data are means±s.e.m., n=10 for each point. *P<0.05 compared with control, one-way ANOVA with Tukey's multiple comparison test. †P<0.01 compared with control, unpaired, two-tailed Student's t-test.

FIG. 4A shows population I-V curves from HEK293 expressing $\alpha_{1C}$+$\beta_{1b}$+$\alpha_2\delta$-1 with either nb.F3 (black, $I_{peak,\ 0mV}$=−48.4±8.4 pA/pF, n=12) or $Ca_V$-aβlator (red, $I_{peak,\ 0mV}$=−0.93±0.16 pA/pF, n=8). FIGS. 4B-4D are in the same format as FIG. 4A for cells expressing reconstituted $Ca_V1.3$ (FIG. 4B), $Ca_V2.1$ (FIG. 4C), or $Ca_V2.3$ (FIG. 4D) channels. Data are means±s.e.m. †p<0.01 compared with control, unpaired, two-tailed Student's t-test.

FIG. 5A shows confocal images (top) and representative traces from whole-cell recordings of uninfected guinea pig cardiomyocytes (left), or infected with adenovirus expressing either $Ca_V$-βlator (middle) or nb.F3-Nedd4L[C942S] (right). Scale bar 0.2 nA, 10 ms. FIG. 5B shows population I-V curves from cardiomyocytes expressing $Ca_V$-βlator (red), nb.F3-Nedd4L[C942S] (green), or an uninfected control (black). In FIG. 5C, on the left, shows representative confocal images of cardiomyocytes fixed and immunostained with $\alpha_{1C}$ (green) and ryanodine receptor (RyR2, magenta) antibodies. The yellow boxes indicate regions of high-zoom merge image. On the right, a graph shows co-localization between $\alpha_{1C}$ and RyR in uninfected cardiomyocytes (gray, PCC=0.47±0.02, n=15), and those expressing either $Ca_V$-aβlator (red, PCC=0.24±0.02 n=19), or nb.F3-Nedd4L[C942S] (green, PCC=0.50±0.01, n=17). In FIG. 5D, on the left, shows representative confocal images of fixed cardiomyocytes immunostained with $\alpha_{1C}$ (green) and Rab7 (magenta) antibodies. The yellow boxes indicate regions of high-zoom merge image. On the right, a graph shows colocalization between $\alpha_{1C}$ and Rab7 in uninfected cardiomyocytes (gray, PCC=0.29±0.02, n=16), and those expressing either $Ca_V$-aβlator (red, PCC=0.42±0.02, n=18), or nb.F3-Nedd4L[C942S] (green, PCC=0.30±0.03, n=16). FIG. 5E shows the pulldown of $\alpha_{1C}$ in HEK293 cells expressing $\alpha_{1C}$, $\beta_{1b}$ and either CFP, nb.F3, $Ca_V$-aβlator, or nb.F3-Nedd4L-[C942S]. Top panel, shows probing pull-down with $\alpha_{1C}$ antibody. Bottom panel, shows the same blot stripped and re-probed with ubiquitin antibody. FIG. 5F shows the quantification of four separate experiments, as performed in FIG. 5E. Data are means±s.e.m for each point. *p<0.05 compared to control, one-way ANOVA with Tukey's multiple comparison test. FIG. 5G shows the pull-down of $Ca_V\beta_1$b, as in FIG. 5E. Left panel, shows probing with $Ca_V\beta_1$b. Right panel, shows the same blot stripped and re-probed with ubiquitin antibody. FIG. 5H is a cartoon illustrating $Ca_V$-aβlator-induced relocation of $Ca_V1.2$ from dyads to Rab7-positive late endosomes in cardiomyocytes.

FIG. 6A shows representative Fura-2 traces of murine DRG neurons infected with GFP (left panel), F3-Nedd4L (middle panel), F3-Nedd4L [C942S] (right panel), with confocal images in inset. The orange bars represent depolarization with 40 mM KCl. FIG. 6B shows a summary of the maximum responses from neurons infected with GFP (Peak response=1.25±0.04, n=84), F3-Nedd4L (1.04±0.01, n=77), and F3-Nedd4L [C942S] (1.30±0.05, n=92) in response to 40 mM KCl. Peaks were normalized to the baseline, defined as 1 min prior to the addition of KCl. FIG. 6C shows representative traces of DRG neurons infected with GFP (left), F3-Nedd4L (middle), F3-Nedd4L[C942S] (right). Traces were collected at both a holding potential of −90 mV (top) and −50 mV (bottom). Notably, $Ca_V$-aβlator-infected neurons still show robust T-type current when held at −90 mV. FIG. 6D shows population I-V curves from DRG neurons infected as in FIG. 6A. Measurements were made at a holding potential of −90 mV. Symbols are mean currents calculated from 15 to 20 ms of a 20 ms test pulse. Data are means±s.e.m. FIG. 6E shows representative fura-2 traces from dispersed pancreatic islets infected with $Ca_V$-aβlator (left) or F3-Nedd4L[C942S] (right) challenged with 16.8 mM glucose (blue bars) and 40 mM KCl (orange bars). FIG. 6F shows a summary of the maximum responses from pancreatic β-cells infected with GFP (Peak response=1.22±0.02, n=53), F3-Nedd4L (Peak response=1.04±0.01, n=62), and F3-Nedd4L[C942S] (Peak response=1.18±0.01, n=122) in response to 16.8 mM glucose. FIG. 6G shows a summary of the maximum responses from pancreatic β-cells infected with GFP (Peak response=1.25±0.02, n=77), F3-Nedd4L (Peak response=1.04±0.01, n=62), and F3-Nedd4L[C942S] (Peak response=1.21±0.01, n=122) in response to 40 mM KCl. Data are means±s.e.m. *p<0.05 compared to control, one-way ANOVA with Tukey's multiple comparison test.

FIG. 8A shows representative flow cytometry dot plot of cells transfected with BBS-$\alpha_{1B}$, $\alpha_2$-δ, YFP-$Ca_V\beta_2$ and CFP (left) or nb.F3 (right). FIG. 8B shows a cumulative distribution histogram of data from FIG. 8A of Alexa-647 (left) or YFP fluorescence (right) from CFP (black) or nb.F3 (red) expressing cells. YFP-positive cells (n=>5,000 cells/experiment) were selected for analysis; the threshold for 647 labeling and YFP fluorescence above background is represented with the dashed line. FIGS. 8C and 8D are in the same format as in FIGS. 8A and 8B for cells expressing YFP-$Ca_V\beta_3$. FIGS. 8E and 8F are in the same format as in FIGS. 8A and 8B for cells expressing $Ca_V\beta_4$.

FIG. 9A shows a cartoon of an experimental strategy according to the present disclosure. BBS-$\alpha_{1C}$ was transfected in HEK293 cells with each YFP-$Ca_V\beta$ and either CFP or nb.F3-P2A-CFP. FIG. 9B shows a representative flow cytometry dot plot of cells transfected with BBS-$\alpha_{1C}$, $Ca_V\beta_1$ and CFP (left) or nb.F3 (right). FIG. 9C shows a cumulative distribution histogram of Alexa-647 (left) or YFP fluorescence (right) from CFP (black) or nb.F3 (red) expressing cells. YFP-positive cells (n>5,000 cells/experiment) were selected for analysis; the threshold for 647 labeling and YFP fluorescence above background is represented with the dashed line. FIG. 9D shows a summary of flow cytometry data of surface (647, filled) and total (YFP, patterned) levels of BBS-$\alpha_{1C}$. Data from nb.F3 was normalized to CFP control group. N=4 separate experiments, error bars, s.e.m. FIG. 9E shows population I-V curves from whole-cell patch clamp measurements in HEK293 cells expressing $\alpha_{1C}$, $Ca_V\beta_{2a}$, and CFP (black, n=9) or nb.F3 (red, n=12). Data are means±s.e.m.

FIG. 10A shows a representative flow cytometry dot plot of cells transfected with BBS-$\alpha_{1B}$, $\alpha_2$-δ, YFP-$Ca_V\beta_1$ and nb.F3 (left), nb.F3-Nedd4L (middle) or nb.F3-Nedd4L[C942S] (right). FIG. 10B shows a histogram of YFP (left) or Alexa-647 fluorescence (right) from samples in FIG. 10A. YFP-positive cells (n>5,000/experiment) were selected for analysis, the threshold for 647 labeling above background is represented with the dashed line. FIGS. 10C and 10D are in the same format as FIGS. 10A and 10B for cells expressing YFP-$Ca_V\beta_2$. FIGS. 10E and 10F are in the same format as FIGS. 10A and 10B for cells expressing YFP-$Ca_V\beta_3$. FIGS. 10G and 10H are in the same format as FIGS. 10A and 10B for cells expressing YFP-$Ca_V\beta_4$.

FIG. 11A shows a schematic of an experimental design according to the present disclosure. HEK293 cells were transfected with BBS-$\alpha_{1C}$, YFP-$Ca_V\beta$, and either nb.F3, nb.F3-Nedd4L or nb.F3-Nedd4L[0942S]. FIG. 11B shows a representative flow cytometry dot plot of cells transfected with BBS-$\alpha_{1C}$, YFP-$Ca_V\beta_{1b}$ and nb.F3 (left), nb.F3-Nedd4L (middle) or nb.F3-Nedd4L[0942S] (right). FIGS. 11C and 11D show histograms of YFP (FIG. 11C) and Alexa-647 (FIG. 11D) fluorescence from samples in FIG. 11B (left) and summary data from N=3 separate experiments (right). YFP-positive cells (n>5,000 cells per experiment) were selected for analysis, the threshold for 647 labeling above background is represented with the dashed line. *p<0.05 compared with control, one-way ANOVA with Tukey's multiple comparison test.

FIG. 12A shows a comparison of total $\alpha_{1C}$ levels in uninfected cardiomyocytes (gray, n=15) and those infected with nb.F3-Nedd4L (red, n=19). FIG. 12B shows a comparison of total $\beta_2$ levels in uninfected cardiomyocytes (gray, n=15) and those infected with nb.F3-Nedd4L (red, n=16), normalized to uninfected controls. Data are means±s.e.m. FIG. 12C (left panel) shows representative confocal images of uninfected (top) or F3-Nedd4L-infected (bottom) guinea pig cardiomyocytes, fixed and immunostained with antibodies towards $\alpha_{1C}$ (left) and LAMP1 (middle). The right panel shows colocalization between $\alpha_{1C}$ and Rab5 in uninfected cardiomyocytes (gray, n=7) and those expressing F3-Nedd4L (red, n=7). Data are means±s.e.m. FIG. 12D is in the same format as FIG. 12C, showing immunostaining and colocalization analysis of cardiomyocytes immunostained against $\alpha_{1C}$ and Rab5.

DETAILED DESCRIPTION OF THE DISCLOSURE

Figure 1A:
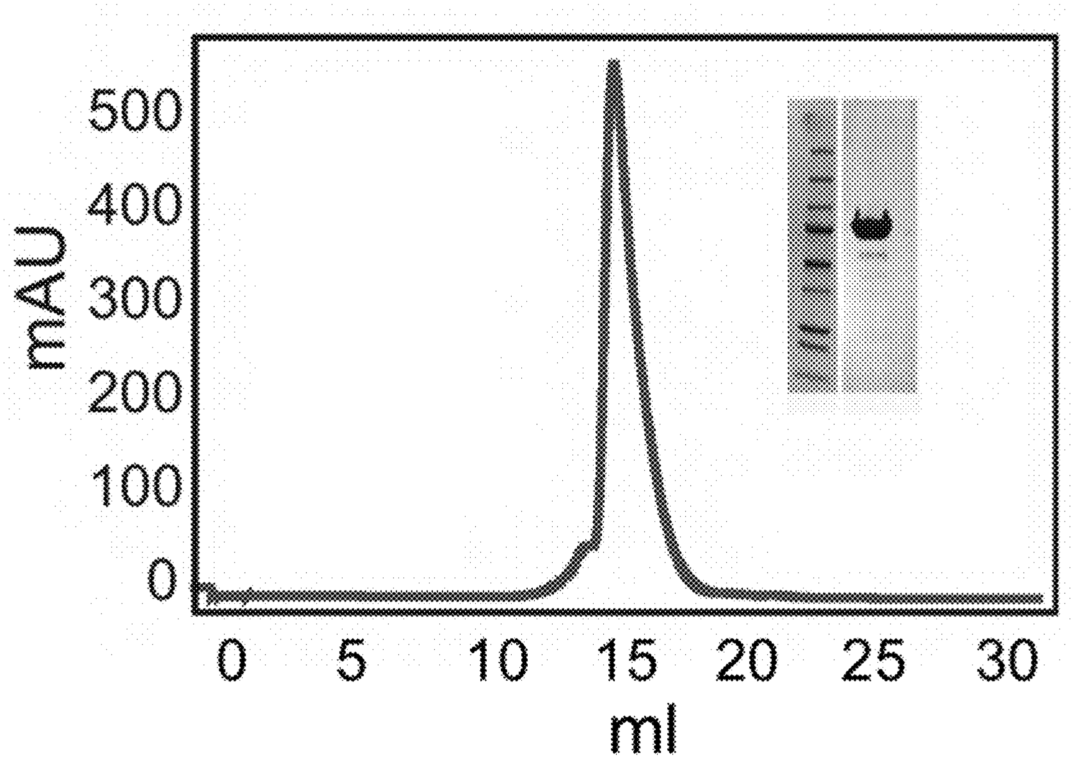

Inhibition of high-voltage-activated calcium channels (HVACCs) is an important prevailing or potential therapy for diverse cardiovascular (hypertension, cardiac arrhythmias, cerebral vasospasm) and neurological diseases (epilepsy, chronic pain, Parkinson's disease) (Zamponi et al., 2015). Small molecule HVACC inhibitors include $Ca_V1$ blockers (dihydropyridines, benzothiazepenes phenylalkylamines) and venom peptides that target $Ca_V2.1$ (ω-agatoxin), $Ca_V2.2$ (ω-conotoxin), and $Ca_V2.3$ (SNX-482) channels. When introduced into an organism, small-molecule HVACC blockers are typically widely distributed leading to off-target effects that can narrow the therapeutic window and, thereby, adversely impact therapy. Genetically-encoded HVACC inhibitors can circumvent off-target effects because they can be selectively expressed in target tissues or cells; thus, they may be useful alternatives or complements to small molecule therapy (Yang et al., 2013; Murata et al., 2004).

There are seven distinct HVACCs ($Ca_V1.1$-$Ca_V1.4$, $Ca_V2.1$-$Ca_V2.3$) which exist in cells as multi-subunit complexes comprising pore-forming al-subunits assembled with auxiliary proteins which include β, $\alpha_2$-δ, and γ subunits (Zamponi et al., 2015; Buraei and Yang, 2010; Dolphin, 2012). HVACCs are named according to the identity of the component $\alpha_1$ subunit ($\alpha_{1A}$-$\alpha_{1F}$; $\alpha_{1S}$) which also contains the voltage sensor, selectivity filter, and channel pore. The various auxiliary subunits typically regulate HVACC trafficking, gating, and modulation, and are recognized as potential targets for developing HVACC-directed therapeutics. For example, gabapentin, which is clinically utilized for treating epilepsy and neuropathic pain, targets HVACC $\alpha_2$-δ subunits (Gee et al., 1996). Based on the presumption that the association of $\alpha_1$ with β is obligatory for the formation of surface-targeted functional HVACCs as indicated by heterologous expression experiments (Buraei and Yang, 2010), disruption of the $\alpha_1$-β interaction has been long pursued as a strategy to develop HVACC inhibitors (Young et al., 1998; Findeisen et al., 2017; Chen, 2018; Khanna et al., 2019). To this end, over-expression of peptides derived from the al-interaction domain (AID) which contains the amino acid sequence responsible for high-affinity $\alpha_1$-β association (Pragnell et al., 1994; Van Petegem et al., 2004; Chen et al., 2004; Opatowsky et al., 2003), has been utilized by several groups as putative genetically-encoded HVACC inhibitors (Findeisen et al., 2017; Yang et al., 2019). However, the efficacy of this approach in vivo may be limited as recent data suggests that in some adult tissue the $\alpha_1$-β interaction is not absolutely essential for surface trafficking of HVACCs (Yang et al., 2019; Meissner et al., 2011).

Rad/Rem/Rem2/Gem/Kir (RGK) proteins are endogenous small Ras-like G-proteins that profoundly inhibit all HVACCs when over-expressed in either heterologous cells or native tissue (Beguin et al., 2001; Finlin et al., 2003; Chen et al., 2005; Xu et al., 2010). They form ternary complexes with HVACCs via binding to constituent β subunits and inhibit currents via multiple mechanisms including removal of surface channels and impairing gating (Yang and Colecraft, 2013; Yang et al., 2010). Despite their efficacy, utility of RGKs as genetically-encoded HVACC inhibitors is confounded by potential off-target effects since they interact with and regulate other binding partners such as cytoskeletal proteins, 14-3-3, calmodulin, and CaM kinase II (Yang and Colecraft, 2013; Correll et al., 2008; Royer et al., 2018; Béguin et al., 2005; Ward et al., 2004). A critical unmet need is the development of genetically-encoded HVACC inhibitors that possess the high efficacy of RGKs but lack the problematic interactions with other signaling proteins. The present disclosure achieves this goal by fusing the homologous to the E6-AP carboxyl terminus (HECT) catalytic domain of the E3 ubiquitin ligase, neural precursor cell developmentally down-regulated protein 4 (Nedd4-2 or hereafter referred to as Nedd4L), to a $Ca_V\beta$-targeted nanobody. The resulting construct, termed $Ca_V$-aβlator, eliminated diverse HVACCs both in both reconstituted systems and native excitable cells, providing a unique new tool for probing $Ca_V1/Ca_V2$ signaling and regulation in vivo, and potential development into a therapeutic.

Ubiquitin (Ub) is a small, 9 kilodalton protein that is covalently attached to a target protein as a post-translational modification. The transfer of cytosolic Ub onto a protein is a multi-step reaction that culminates with a class of enzymes called E3 ubiquitin ligases mediating the final step of Ub attachment. There are more than 600 E3 ubiquitin ligases in the human genome; this diversity could in part be explained by the diverse nature of the ubiquitin code: Ub chains are formed by the subsequent addition of Ub onto an existing Ub bound to the target protein. Complexity arises as Ub itself has 7 lysine residues that can be potentially ubiquitinated (as well as its N-terminal methionine). The shape of the resulting polyubiquitin chains can alter the downstream fate of the target protein. For example, K48 E3 ligases have been demonstrated in vitro to add Ub onto the 48th residue of an existing Ub, forming K48 polyubiquitin chains which have been characterized as a signal for proteosomal degradation of the target protein. Additional signaling roles for ubiquitin have been characterized such as K63 branches coordinating endocytosis of plasma membrane proteins. In particular, the HECT family ligase Nedd4-2 has been well characterized to target to the plasma membrane, where it mediates endocytosis and ultimately lysosomal degradation of a host of PY-containing transmembrane proteins such as ENaC, KCNQ1, and NaV1.5.

The present disclosure provides, inter alia, a strategy to genetically encode HVACC inhibitors, providing a means to spatially restrict therapy to a certain tissue or cell population, by utilizing the ubiquitin pathway. According to some embodiments, certain aspects of the present disclosure target the β subunit and take advantage of the ubiquitin pathway to remove HVACCs from the cell surface.

In some embodiments, the present disclosure comprises two elements: 1) a novel nanobody that is able to bind all four $Ca_V$13 auxiliary subunits, and linked to 2) a catalytic domain of an E3 ubiquitin ligase. In some embodiments, rather than physically blocking the channel from performing its function, the channel is removed from its functional destination, the plasma membrane. In some embodiments, the channel is removed from its functional destination in a genetically-encoded manner, allowing cellular specificity to be achieved with, but not limited to, transfection or viral-vector based methods. In some embodiments, the ubiquitin signaling system present in all eukaryotic cells is utilized in order to redirect ubiquitination, and thus functional knockdown of HVACCs.

In order to direct the ubiquitin machinery to HVACCs, in some embodiments, the present disclosure provides a generated nanobody towards the auxiliary β subunit ($Ca_V\beta$) of HVACCs. As used herein, the term "nanobodies" means small antibody fragments derived from a class of camelid antibodies having a small size (1/10th the size of a conventional antibody). According to some embodiments, the nanobodies are amenable to genetic engineering and further, they are able to bind their antigen with a single heavy variable chain, endowing them with unique stability within the reducing environment of a living cell. According to some embodiments, the present disclosure provides an engineered catalytic domain of the HECT domain E3 ubiqutin ligase Nedd4-2 onto a $Ca_V\beta$ nanobody to create a genetically-encoded calcium channel blocker. In some embodiments, by engineering the catalytic domain of a ubiquitin ligase, including but not limited to Nedd4-2, onto the nanobody, the ubiquitination of the β auxiliary subunit is targeted, which is necessary for proper HVACC trafficking to the plasma membrane. In some embodiments, this targeting is sufficient to abolish surface levels of some, including a minority, a majority and even all HVACCs. In some embodiments, the present disclosure provides a genetically-encoded calcium channel blocker. In some embodiments, the calcium channel blocker of the present disclosure blocks HVACCs in a spatially defined manner.

According to some embodiments, this disclosure provides a novel means to block all HVACCs by a fundamentally different mechanism than that of typical HVACC blockers. In some embodiments, the HVACC blockers of the present disclosure may be used for treatment of diabetes and Parkinson's disease, and as a gene therapy approach for a number of diseases. In some embodiments, the disclosure is genetically encoded to be delivered with spatial precision, minimizing off-target effects.

According to some embodiments, the present disclosure provides a nanobody that recognizes some or all $Ca_V\beta$ subunits enabling the targeting of endogenous HVACCs. In some embodiments, the catalytic subunit of the E3 ubiquitin ligase Nedd4-2 is used with a nanobody.

According to some embodiments, the present disclosure provides, 1) a means to block all HVACCs, without the need for several pharmacological agents, including expensive venom-derived peptides, to achieve similar functional effects; 2) a genetically-encoded means to achieve HVACC blockade, which may target a particular tissue and may be delivered via adenovirus/AAV or transfection methods, providing a means to target specific tissues; 3) a gene therapy by selectively targeting populations of neurons that mediate pain sensation; and 4) a nanobody homing device that can be used to target other active protein moieties to HVACCs.

According to some embodiments, the present disclosure provides a genetically-encoded HVACC blocker (in contrast to several expensive pharmacological agents). In some embodiments, the present disclosure provides a gene therapy to selectively down-regulate function of HVACCs in specific populations of cells.

In particular, twenty-five unique $Ca_V\beta$-targeted nanobodies were developed and identified based on the unique sequences within complementarity determining regions (CDR1-3), the major determinants of antigen binding. These nanobodies may be incorporated into $Ca_V$ channel complexes but be functionally silent, and thereby serve as a vehicle to potentially address distinct enzymatic moieties or sensors to endogenous channels.

Accordingly, one embodiment of the present disclosure is a nanobody capable of binding to a $Ca_V\beta$ auxiliary subunit, comprising SEQ ID NOs: 1-3, SEQ ID NOs: 5-7, SEQ ID NOs: 9-11, SEQ ID NOs: 13-15, SEQ ID NOs: 17-19, SEQ ID NOs: 21-23, SEQ ID NOs: 25-27, SEQ ID NOs: 29-31, SEQ ID NOs: 33-35, SEQ ID NOs: 37-39, SEQ ID NOs:

41-43, SEQ ID NOs: 45-47, SEQ ID NOs: 49-51, SEQ ID NOs: 53-54, SEQ ID NOs: 56-57, SEQ ID NOs: 59-61, SEQ ID NOs: 63-65, SEQ ID NOs: 67-69, SEQ ID NOs: 71-73, SEQ ID NOs: 75-77, SEQ ID NOs: 79-81, SEQ ID NOs: 83-85, SEQ ID NOs: 87-89, SEQ ID NOs: 91-93, or SEQ ID NOs: 95-97.

In some embodiments, the nanobody comprises SEQ ID NO: 4, SEQ ID NO: 8, SEQ ID NO: 12, SEQ ID NO: 16, SEQ ID NO: 22, SEQ ID NO: 26, SEQ ID NO: 30, SEQ ID NO: 34, SEQ ID NO: 38, SEQ ID NO: 42, SEQ ID NO: 46, SEQ ID NO: 48, SEQ ID NO: 52, SEQ ID NO: 55, SEQ ID NO: 58, SEQ ID NO: 62, SEQ ID NO: 66, SEQ ID NO: 70, SEQ ID NO: 74, SEQ ID NO: 78, SEQ ID NO: 82, SEQ ID NO: 86, SEQ ID NO: 90, SEQ ID NO: 94, or SEQ ID NO: 98.

Another embodiment of the present disclosure is a composition comprising: (i) a nanobody as disclosed herein; and (ii) a catalytic domain of an E3 ubiquitin ligase operably connected to the nanobody. In this context, the term "operably connected" means that one function is regulated by another thing by association with a polypeptide sequence on, e.g., a single polypeptide.

In some embodiments, the composition is effective to remove a High-Voltage Activated Calcium Channel (HVACC) from its functional location on a plasma membrane of a cell. In some embodiments, the HVACC is selected from the group consisting of $Ca_V1.1$, $Ca_V1.2$, $Ca_V1.3$, $Ca_V1.4$, $Ca_V2.1$, $Ca_V2.2$, $Ca_V2.3$, and combinations thereof. In some embodiments, the HVACC is one or more of $Ca_V1.2$, $Ca_V1.3$, $Ca_V2.1$, and $Ca_V2.3$. In some embodiments, the composition is effective to achieve functional knockdown of the HVACC. In some embodiments, the E3 ubiquitin ligase comprises the catalytic domain of Nedd4-2. In some embodiments, the composition is effective to impair the function of a $Ca_V\beta$ auxiliary subunit of trafficking the HVACC to the plasma membrane. In some embodiments, the composition is effective to abolish surface levels of some, including a minority of, a majority of and even all HVACCs. In some embodiments, the composition is effective to reduce or eliminate HVACC currents.

Another embodiment of the present disclosure is a composition comprising a genetically encoded calcium channel blocker comprising a nucleic acid encoding: (i) a nanobody as disclosed herein; and (ii) a catalytic domain of an E3 ubiquitin ligase.

In some embodiments, the E3 ubiquitin ligase comprises a catalytic domain of Nedd4-2. In some embodiments, the nanobody and the catalytic domain of the E3 ubiquitin ligase are operably connected, i.e., functionally linked. In this context, the term "operably connected" means that one function is regulated by another thing by association with a polynucleotide sequence on, e.g., a single polynucleotide. In some embodiments, the nanobody and the catalytic domain of the E3 ubiquitin ligase are expressed to form a contiguous polypeptide. In some embodiments, the contiguous polypeptide is effective to remove a High-Voltage Activated Calcium Channel (HVACC) from its functional location on a plasma membrane of a cell. In some embodiments, the HVACC is selected from the group consisting of $Ca_V1.1$, $Ca_V1.2$, $Ca_V1.3$, $Ca_V1.4$, $Ca_V2.1$, $Ca_V2.2$, $Ca_V2.3$, and combinations thereof. In some embodiments, the HVACC is one or more of $Ca_V1.2$, $Ca_V1.3$, $Ca_V2.1$, and $Ca_V2.3$. In some embodiments, the contiguous polypeptide is effective to achieve functional knockdown of a HVACC in the cell. In some embodiments, the contiguous polypeptide is effective to impair, e.g., to decrease or abolish the function of a $Ca_V\beta$ auxiliary subunit of trafficking a HVACC to the plasma membrane. In some embodiments, the contiguous polypeptide is effective to abolish surface levels of all HVACCs. In some embodiments, the contiguous polypeptide is effective to reduce or eliminate HVACC currents. In some embodiments, the nucleic acid encoding (i) and (ii) is carried on an expression vector. In some embodiments, the expression vector further comprises a tissue specific promoter.

A further embodiment of the present disclosure is a method of blocking a High-Voltage Activated Calcium Channel (HVACC) in a cell, comprising contacting the cell with an effective amount of a composition as disclosed herein.

In some embodiments, the cell is a neuron or a cardiac myocyte.

Another embodiment of the present disclosure is a method of selectively targeting a population of cells in a subject, comprising administering to the subject an effective amount of a composition as disclosed herein.

In some embodiments, the cells are neurons that mediate pain sensation or cardiac myocytes.

In some embodiments, the subject is a mammal. In some embodiments, the subject is a human.

Another embodiment of the present disclosure is a composition for inducible inhibition of a High-Voltage Activated Calcium Channel (HVACC) in a cell comprising: (i) a nanobody as disclosed herein; and (ii) a C1 domain from protein kinase $C\gamma(C1_{PKC})$ operably connected to the nanobody; wherein the composition is effective to inactivate the HVACC after induction with phorbol-12,13-dibutyrate (PdBu). In the present disclosure, the C1 domain of protein kinase Cγ may be induced using known inducing agents, such as, e.g., phorbol esters, including PdBu. Although, PdBu is exemplified herein, other protein kinase Cγ inducing agents may be used, including but not limited to, e.g., Bryostatin 1, ingenol-3-angelate (I3A, PEP005), phorbol-12-myristate-13-acetate (PMA), prostratin, SC-9, SC-10, 1-oleoyl-2-acetyl-sn-glycerol, (−)-indolactam V, ingenol, 1-stearoyl-2-arachidonoyl-sn-glycerol.

In some embodiments, the composition is effective to achieve functional knockdown of the HVACC. In this context, the term "functional knockdown" means using an agent such as the composition according to the present disclosure to cause transient loss of normal function of a HVACC, including, e.g., exciting neurons, releasing neurotransmitters, hormones, or initiating the contraction of both skeletal and cardiac muscle, etc. The "functional knockdown" of a HVACC can be quantified by conventional techniques such as, e.g., RT-qPCR.

An additional embodiment of the present disclosure is a composition comprising a genetically encoded inducible calcium channel blocker comprising a nucleic acid encoding: (i) a nanobody as disclosed herein; and (ii) a C1 domain from protein kinase $C\gamma(C1_{PKC})$ operably connected to the nanobody.

In some embodiments, the nanobody and the C1 domain are expressed to form a contiguous polypeptide. In some embodiments, the nucleic acid encoding (i) and (ii) is carried on an expression vector. In some embodiments, the expression vector further comprises a tissue specific promoter. In the present disclosure, non-limiting exemplary tissue specific promoters include, e.g., native promoters such as B29 promoter, CD14 promoter, CD43 promoter, CD45 promoter, CD68 promoter, desmin promoter, elastase-1 promoter, endoglin promoter, fibronectin promoter, flt-1 promoter, GFAP promoter, GPIIb promoter, ICAM-2 promoter, mouse INF-β promoter, Mb promoter, NpshI promoter, OG-2 promoter, SP-B promoter, SYN-1 promoter, WASP promoter, and composite promoters such as SV40/bAlb promoter, SV40/hAlb promoter, SV40/CD43 promoter, SV40/CD45 promoter, NSE/RU5' promoter.

Another embodiment of the present disclosure is a method of blocking a High-Voltage Activated Calcium Channel (HVACC) in a cell, comprising the step of: (i) contacting the cell with an effective amount of a composition as disclosed herein; and (ii) contacting the cell with a protein kinase Cy inducing agent, such as phorbol-12,13-dibutyrate (PdBu); wherein the contacting of steps (i) and (ii) are effective to remove the HVACC from its functional location on a plasma membrane of the cell. As used herein, the term "blocking" means partially or completely interfering with the HVACC so as to achieve a desired clinical effect.

In some embodiments, the cell is f a neuron or a cardiac myocyte.

Still another embodiment of the present disclosure is a method for treating or ameliorating the effects of a disease in a subject, comprising administering to the subject an effective amount of a composition as disclosed herein.

In some embodiments, the subject is a mammal. In some embodiments, the subject is a human.

In some embodiments, the disease is associated with dysregulation of a high-voltage-activated calcium channel (HVACC). In some embodiments, the HVACC is selected from the group consisting of $Ca_V1.1$, $Ca_V1.2$, $Ca_V1.3$, $Ca_V1.4$, $Ca_V2.1$, $Ca_V2.2$, $Ca_V2.3$, and combinations thereof. In some embodiments, the HVACC is one or more of $Ca_V1.2$, $Ca_V1.3$, $Ca_V2.1$, and $Ca_V2.3$.

In some embodiments, the disease is selected from the group consisting of a cardiovascular disease, a neurological disease, and combinations thereof. Non-limiting examples of a cardiovascular disease include angina, myocardial infarction, stroke, heart failure, hypertension, cardiac arrhythmias, cerebral vasospasm, rheumatic heart disease, cardiomyopathy, abnormal heart rhythms, congenital heart disease, valvular heart disease, carditis, endocarditis, myocarditis, eosinophilic myocarditis, aortic aneurysms, peripheral artery disease, thromboembolic disease, venous thrombosis, and combinations thereof. In some embodiments, the cardiovascular disease is selected from the group consisting of hypertension, cardiac arrhythmias, cerebral vasospasm, and combinations thereof.

Non-limiting examples of a neurological disease include epilepsy, chronic pain, Parkinson's disease, amyotrophic lateral sclerosis (ALS), Alzheimer's disease, aneurysm, back pain, Bell's palsy, birth defects of the brain and spinal cord, brain injury, brain tumor, cerebral palsy, chronic fatigue syndrome, consussion, dementia, Disk disease of neck and lower back, dizziness, Guillain-Barré syndrome, headaches and migraines, multiple sclerosis, muscular dystrophy, neuralgia, neuropathy, neuromuscular and related diseases, severe depression, obsessive-compulsive disorder, scoliosis, seizures, spinal cord injury, spinal deformity and disorders, spine tumor, stroke, vertigo, and combinations thereof. In some embodiments, the neurological disease is selected from the group consisting of epilepsy, chronic pain, Parkinson's disease, and combinations thereof.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present disclosure may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population, may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present disclosure include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include primates, rats, mice, rabbits, guinea pigs, etc.

As used herein, the term "contacting" means bringing a composition and optionally one or more additional therapeutic agents into close proximity to the cells in need of modulation such as blocking or inhibiting HVACC activities. This may be accomplished using conventional techniques of drug delivery to the subject or in the in vitro situation by, e.g., providing the compound and optionally other therapeutic agents to a culture media in which the cells are located.

In the present disclosure, an "effective amount" or "therapeutically effective amount" of a composition is an amount of such a composition that is sufficient to effect beneficial or desired results as described herein when administered to a subject or contacted with a cell. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of the subject, and like factors well known in the arts of, e.g., medicine and veterinary medicine. In general, a suitable dose of a composition according to the disclosure will be that amount of the composition, which is the lowest dose effective to produce the desired effect with no or minimal side effects. The effective dose of a composition according to the present disclosure may be administered as two, three, four, five, six or more sub-doses, administered separately at appropriate intervals throughout the day.

A suitable, non-limiting example of a dosage of a composition according to the present disclosure is from about 1 ng/kg to about 1000 mg/kg, such as from about 1 mg/kg to about 100 mg/kg, including from about 5 mg/kg to about 50 mg/kg. Other representative dosages of a composition of the present disclosure include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

A composition of the present disclosure may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a composition of the present disclosure may be administered in conjunction with other treatments. A composition of the present disclosure may be encapsulated or otherwise protected against gastric or other secretions, if desired.

The following examples are provided to further illustrate the methods of the present disclosure. These examples are illustrative only and are not intended to limit the scope of the disclosure in any way.

EXAMPLES

Example 1

Materials and Methods

Protein Purification

The BacMam expression system was used to purify $Ca_V\beta_{1B}$ and $Ca_V\beta_3$ (Goehring et al., 2014). Briefly, full-length $Ca_V\beta_{1b}$ and $Ca_V\beta_3$ were cloned into a modified pEG BacMam vector with a C-terminal FLAG tag using BamHI and EcoRI sites. BacMam virus was subsequently generated in Sf9 cells and harvested after three rounds of amplification. 100 mL of BacMam virus was used to infect 1 L of HEK293 $GnTI^-$ cells (N-acetylglucosaminyltransferase I-negative) and kept shaking at 37° C. After 18 hrs the cells were stimulated with 10 mM sodium butyrate and harvested 72 hrs later. Cells were lysed using an Avestin Emulsiflex-C3 homogenizer in buffer containing 50 mM Tris, 150 mM KCl, 10% sucrose, 1 mM PMSF (phenylmethylsulfonyl fluoride), and EDTA-free Complete protease inhibitor cocktail (Roche), pH 7.4. Lysate was spun down at 35,000 g for 1 hr. $Ca_V\beta$ was subsequently isolated from supernatant with anti-FLAG antibody (M2) affinity chromatography, and eluted with 100 µg/mL FLAG peptide (Sigma Millipore) in 50 mM TrisHCl, 150 mM KCl, pH 7.4. The protein was then applied to an ion exchange column (MonoQ, GE) and eluted with a linear KCl gradient of 50 mM to 1M. Peak fractions were collected and subjected to size exclusion chromatography (Superdex 200, GE) in a buffer containing 20 mM Tris, 150 mM KCl, pH 7.4. Proteins were brought to 20% glycerol, flash frozen, and stored at −80° C.

For isothermal titration calorimetry experiments, both $Ca_V\delta_{2b}$ and nb.F3 were cloned via Gibson assembly (Gibson et al., 2009) into an IPTG (isopropyl δ-D-1-thiogalactopyranoside) inducible, kanamycin-resistant pET derived plasmid (Novagen, Madison, Wisconsin), with an N-terminal deca-histidine tag (His10) and transformed into Rosetta DE3 *E. coli* (Millipore Sigma), following manufacturers' instructions. Cells were grown at 37° C. in 1 L 2×TY media supplemented with 50 µg/mL carbenicillin and 35 µg/mL chloramphenicol and shook at 225 rpm. Protein expression was induced with 0.2 mM IPTG when the cells reached an OD of 0.6-0.8. The cells were then grown overnight at 22° C.

Nb.F3 was purified as previously described (McMahon et al., 2018): briefly, cells were harvested and resuspended in 100 mL buffer containing (mM) 500 sucrose, 200 Tris (pH 8), 0.5 EDTA and osmotically shocked with the addition of 200 mL water with stirring. The lysate was brought to a concentration of (mM) 150 NaCl, 2 $MgCl_2$, and 20 imidazole and centrifuged at 20,000 g, 4° C. for 30 min. The supernatant was combined with 2 mL Ni-NTA Sepharose resin (Qiagen) in batch, washed with 70 mM imidazole, and eluted with 350 mM imidazole. The eluant was dialyzed into a buffer containing 150 mM NaCl, 10 mM HEPES, pH 7.4 and purified with an S200 size exclusion column (GE Healthcare).

For the purification of $Ca_V\beta_{2b}$, cells were pelleted and resuspended in a buffer containing (mM) 300 NaCl, 20 Tris HCl, 10% glycerol, pH 7.4, 0.5 PMSF, and EDTA-free Complete protease inhibitor cocktail (Roche). Cells were lysed using an Avestin Emulisflex-C3 homogenizer and spun at 35,000 g for 30'. The solubilized protein was applied to Ni-NTA Sepharose (Qiagen) and purified as nb.F3.

Nanobody Generation

One llama was immunized with an initial injection of 600 µg purified $Ca_V\beta_{1b}$ and $Ca_V\beta_3$, with four boosters of 200 ug each protein administered every other week (Capralogics Inc, Hardwick, MA). 87 days after the first immunization, lymphocytes were isolated from blood and a cDNA library with ProtoScript II Reverse Transcriptase (New England Biolabs). Nanobodies were isolated as previously described (Pardon et al., 2014), using a two-step nested PCR. Amplified Vhh genes were cloned into the phagemid plasmid pComb3xSS. A phage display library was created using electrocompetent TG1 *E. coli* cells (Lucigen). Three rounds of phage display were performed as previously described (Pardon et al., 2014), using 100 nM biotinylated $Ca_V\beta_3$ as bait on neutravidin-coated Nunc-Immuno plates (Thermo Scientific). Clones of interest were subsequently cloned into mammalian expression systems for further study (see below).

Isothermal Titration Calorimetry

Isothermal Titraction calorimetry measurements were performed using an MicroCal Auto iTC 200 (Malvern Panalytical) at 25° C. Samples were dialyzed into 300 mM NaCl, 20 mM HEPES, 5% glycerol, pH 7.5 and filtered beforehand. Injections of 2 µL nb.F3 into 400 µL of $Ca_V\beta_{2b}$. Data were processed with MicroCal Origin 7.0.

Molecular Biology and Plasmid Construction

Potential nbs were PCR amplified with primers flanking their conserved framework (FW) FW1 and FW4 regions and inserted into the mammalian expression plasmid pcDNA3 (Invitrogen) using HindIII and EcoRI sites. An additional GSG linker was included in the PCR and the insert was ligated upstream of an enhanced CFP and C1 domain of human PKCγ (residues 51-180).

Rat $Ca_V\beta_{1b}$ was PCR amplified for subsequent overlap PCR with YFP, inserting a GSG linker between the two proteins. The resulting $Ca_V\beta_{1b}$-GSG-YFP sequence was digested with BamHI and NotI and ligated into a PiggyBac CMV mammalian expression vector (System Biosciences). A similar cloning strategy was used for $Ca_V\beta_3$ and $Ca_V\beta_4$. Rat $Ca_V\beta_{2a}$ was PCR amplified with an N-terminal YFP to prevent palmitoylation of the $\beta_{2a}$ subunit (Chien et al., 1996) and inserted with a similar strategy.

A customized bicistronic vector (xx-P2A-CFP) was synthesized in the pUC57 vector, in which coding sequence for P2A peptide was sandwiched between an upstream multiple cloning site and enhanced cyan fluorescent protein (CFP) (Genewiz). The xx-P2A-CFP fragment was amplified by PCR and cloned into the PiggyBac CMV mammalian expression vector (System Biosciences) using NheI/NotI sites. To generate nb.F3-P2A-CFP, we PCR amplified the coding sequence for nb.F3 and cloned it into xx-P2A-CFP using NheI/AflII sites. A similar backbone was created in the PiggyBac CMV mammalian expression vector in which CFP-P2A-xx contained a multiple cloning site downstream of the P2A site (Genewiz). Nb.F3 was PCR amplified and ligated into the vector with BglII/AscI sites. The HECT domain of human Nedd4L (Gao et al., 2009) consisting of residues 594-974 was PCR amplified and inserted downstream of nb.F3 using AscI/AgeI sites. Mutagenesis of C942S was accomplished using site-directed mutagenesis.

$\alpha_{1B}$-BBS, harboring two tandem 13 residue bungarotoxin-binding sites (SWRYYESSLEPYPD) in the domain IV S5-S6 extracellular loop, was obtained. $\alpha_{1C}$ and $\alpha_{1C}$-BBS, and $\alpha_{1C}$-BBS-YFP have been described previously (Yang et al., 2010; Kanner et al., 2017).

Cell Culture and Transfection

Human embryonic kidney (HEK293) cells were obtained Cells were *Mycoplasma* free, as determined by the MycoFluor *Mycoplasma* Detection Kit (Invitrogen, Carlsbad, CA). Low passage HEK293 cells were cultured at 37° C. in DMEM supplemented with 5% fetal bovine serum (FBS) and 100 mg/mL of penicillin-streptomycin. HEK293 cell transfection was accomplished using the calcium phosphate precipitation method. Briefly, plasmid DNA was mixed with 7.75 μL of 2 M $CaCl_2$ and sterile deionized water (to a final volume of 62 μL). The mixture was added dropwise, with constant tapping to 62 μL of 2× Hepes buffered saline containing (in mM): Hepes 50, NaCl 280, $Na_2HPO_4$ 1.5, pH 7.09. The resulting DNA-calcium phosphate mixture was incubated for 20 min at room temperature and then added dropwise to HEK293 cells (60-80% confluent). Cells were washed with $Ca^{2+}$-free phosphate buffered saline after 4-6 hr and maintained in supplemented DMEM.

Isolation of adult guinea pig cardiomyocytes was performed in accordance with the guidelines of Columbia University Animal Care and Use Committee. Prior to isolation, plating dishes were precoated with 15 μg/mL laminin (Gibco). Adult female Hartley guinea pigs (Charles River) were euthanized with 5% isoflurane, hearts were excised and ventricular myocytes isolated by first perfusing in KH solution (mM): 118 NaCl, 4.8 KCl, 1 $CaCl_2$) 25 HEPES, 1.25 $K_2HPO_4$, 1.25 $MgSO_4$, 11 glucose, 02 EGTA, pH 7.4, followed by KH solution without calcium using a Langendorff perfusion apparatus. Enzymatic digestion with 0.3 mg/mL Collagenase Type 4 (Worthington) with 0.08 mg/mL protease and. 05% BSA was performed in KH buffer without calcium for six minutes. After digestion, 40 mL of a high $K^+$ solution was perfused through the heart (mM): 120 potassium glutamate, 25 KCl, 10 HEPES, 1 $MgCl_2$, and 02 EGTA, pH 7.4. Cells were subsequently dispersed in high $K^+$ solution. Healthy rod-shaped myocytes were cultured in Medium 199 (Life Technologies) supplemented with (mM): 10 HEPES (Gibco), lx MEM non-essential amino acids (Gibco), 2 L-glutamine (Gibco), 20 D-glucose (Sigma Aldrich), 1% vol $vol^{-1}$ penicillin-streptomycin-glutamine (Fisher Scientific), 02 mg/mL Vitamin B-12 (Sigma Aldrich) and 5% (vol/vol) FBS (Life Technologies) to promote attachment to dishes. After 5 hr, the culture medium was switched to Medium 199 with 1% (vol/vol) serum, but otherwise supplemented as described above. Cultures were maintained in humidified incubators at 37° C. and 5% $CO_2$.

Murine dorsal root ganglion (DRG) neurons were obtained. DRG neurons were isolated as previously described (Albuquerque et al., 2009). DRG neurons were plated onto glass coverslips coated with 15 μg/mL laminin (Corning) and maintained in Neurobasal media (Thermo Fisher Scientific) supplemented with 1×B-27 (Thermo Fisher Scientific), 100 μg $mL^{-1}$ penicillin/streptomycin (Fisher Scientific), 0.29 mg/mL L-glutamine (Gibco), 50 ng $mL^{-1}$ NGF (Sigma Aldrich), 2 ng $mL^{-1}$ GDNF (Sigma Aldrich), and 10 μM cytosine β-D-arabinofuranoside (Sigma Aldrich).

Pancreatic Beta Cell Isolation and Culture

Murine pancreatic β-cells from Rip-Cre (Jackson Laboratories Stock #003573) mice crossed with Rosa26-tdTomato (Jackson Laboratories Stock #007909) mice were obtained. Islets were isolated as previously described (Stull et al., 2012), dispersed with 0.05% trypsin EDTA (Gibco) and plated onto 35 mm glass bottom dishes with 10 mm microwells (Cellvis) pre-coated with 10 mg/mL fibronectin (Sigma Aldrich). Islets were maintained in RPMI 1640 media (Corning) supplemented with 15% FBS and 100 μg $mL^{-1}$ penicillin/streptomycin. Islets were imaged 24-48 hr after adenoviral infection.

Adenoviral Generation

Adenoviral vectors expressing GFP and CFP-P2A-nb.F3-Nedd4L[C942S] were generated using the pAdEasy system (Stratagene) according to manufacturer's instructions as previously described (Kanner et al., 2017; Subramanyam, 2013). Plasmid shuttle vectors (pShuttle CMV) containing cDNA for CFP-P2A-nb.F3-Nedd4L[C942S] were linearized with PmeI and electroporated into BJ5183-AD-1 electrocompetent cells pre-transformed with the pAdEasy-1 viral plasmid (Stratagene). PacI restriction digestion was used to identify transformants with successful recombination. Positive recombinants were amplified using XL-10-Gold bacteria, and the recombinant adenoviral plasmid DNA linearized with PacI digestion. HEK cells cultured in 60 mm diameter dishes at 70-80% confluency were transfected with PacI-digested linearized adenoviral DNA. Transfected plates were monitored for cytopathic effects (CPEs) and adenoviral plaques. Cells were harvested and subjected to three consecutive freeze-thaw cycles, followed by centrifugation (2,500×g) to remove cellular debris. The supernatant (2 mL) was used to infect a 10 cm dish of 90% confluent HEK293 cells. Following observation of CPEs after 2-3 d, cell supernatants were used to re-infect a new plate of HEK293 cells. Viral expansion and purification was carried out as previously described (Colecraft et al., 2002). Briefly, confluent HEK293 cells grown on 15 cm culture dishes (×8) were infected with viral supernatant (1 mL) obtained as described above. After 48 hr, cells from all of the plates were harvested, pelleted by centrifugation, and resuspended in 8 mL of buffer containing (in mM) 20 Tris HCl, 1 $CaCl_2$), one and $MgCl_2$ (pH 8). Cells were lysed by four consecutive freeze-thaw cycles and cellular debris pelleted by centrifugation. The virus-laden supernatant was purified on a cesium chloride (CsCl) discontinuous gradient by layering three densities of CsCl (1.25, 1.33, and 1.45 g/mL). After centrifugation (50,000 rpm; SW41Ti Rotor, Beckman-Coulter Optima L-100K ultracentrifuge; 1 hr, 4° C.), a band of virus at the interface between the 1.33 and 1.45 g/mL layers was removed and dialyzed against PBS (12 hr, 4° C.). Adenoviral vector aliquots were frozen in 10% glycerol at −80° C. until use. Generation of CFP-P2A-nb.F3-Nedd4L was performed by Vector Biolabs (Malvern, PA).

Flow Cytometry Assay of Total and Surface Calcium Channels

Cell surface and total ion channel pools were assayed by flow cytometry in live, transfected HEK293 cells as previously described (Kanner et al., 2017; Aromolaran et al., 2014). Briefly, 48 hr post-transfection, cells cultured in 12-well plates were gently washed with ice cold PBS containing $Ca^{2+}$ and $Mg^{2+}$ (in mM: 0.9 $CaCl_2$), 0.49 MgCl2, pH 7.4), and then incubated for 30 min in blocking medium (DMEM with 3% BSA) at 4° C. HEK293 cells were then incubated with 1 μM Alexa Fluor 647 conjugated α-bungarotoxin (BTX647; Life Technologies) in DMEM/3% BSA on a rocker at 4° C. for 1 hr, followed by washing three times with PBS (containing $Ca^{2+}$ and $Mg^{2+}$). Cells were gently harvested in $Ca^{2+}$-free PBS, and assayed by flow cytometry using a BD Fortessa Cell Analyzer (BD Biosciences, San Jose, CA, USA). CFP- and YFP-tagged proteins were excited at 407 and 488 nm, respectively, and Alexa Fluor 647 was excited at 633 nm.

Electrophysiology

Whole-cell recordings of HEK293 cells were conducted 48 hr after transfection using an EPC-10 patch clamp amplifier (HEKA Electronics) controlled by Pulse software (HEKA). Micropipettes were prepared from 1.5 mm thin-walled glass (World Precision Instruments) using a P97 microelectrode puller (Sutter Instruments). Internal solution contained (m M): 135 cesium-methansulfonate ($CsMeSO_3$), 5 CsCl, 5 EGTA, 1 $MgCl_2$, 2 MgATP, and 10 HEPES (pH 7.3). Series resistance was typically between 1-2 MΩ. There was no electronic resistance compensation. External solution contained (m M): 140 tetraethylammonium-$MeSO_3$, 5 $BaCl_2$, and 10 HEPES (pH 7.4). Whole-cell I-V curves were generated from a family of step depolarizations (−60 mV to +80 mV from a holding potential of −90 mV). Currents were sampled at 20 kHz and filtered at 5 kHz. Traces were acquired at a repetition interval of 10 s. Leak and capacitive transients were subtracted using a P/4 protocol.

Whole-cell recordings of cardiomyocytes and DRG neurons were performed 48 hr after infection. HEK cell internal and external solutions were used for DRG experiments. Whole-cell recordings for guinea pig cardiomyocytes used internal solution comprised of (mM): 150 $CsMeSO_3$, 10 EGTA, 5 CsCl, $MgCl_2$, 4 MgATP, and 10 HEPES. For formation of gigaohm seals and initial break-in to the whole-cell configuration, cells were perfused in Tyrode solution containing (mM): 138 NaCl, 4 KCl, 2 $CaCl_2$), 1 $MgCl_2$, 0.33 $NaH_2PO_4$, and 10 HEPES (pH 7.4). Upon successful break-in, the perfusing media was switched to an external solution composed of (mM): 155 N-methyl-D-glucamine, 10 4-amino-pyridine, 1 $MgCl_2$, 5 $BaCl_2$, and 10 HEPES (pH 7.4). Currents were sampled at 20 kHz and filtered at 5 kHz. Leak and capacitive transients were subtracted using a P/4 protocol.

Immunofluorescence Staining

Approximately 48 hr after adenoviral infection, guinea pig cardiomyocytes were fixed in 4% paraformaldehyde (wt/vol, in PBS) for 20 min at RT. Cells were washed twice with PBS and then incubated in 0.1M glycine (in PBS) for 10 min at RT to block free aldehyde groups. Fixed cells were then permeabilized with 0.2% Triton X-100 (in PBS) for 20 min at RT. Non-specific binding was blocked with a 1 hr incubation at RT in PBS solution containing 3% (vol $vol^{-1}$) normal goat serum (NGS), 1% BSA, and 0.1% Triton X-100. Cells were then incubated with primary antibody in PBS containing 1% NGS, 1% BSA, and 0.1% BSA overnight at 4° C. Cells were washed three times for 10 min each with PBS with 0.1% Triton X-100 and then stained with secondary antibody for 1 hr at RT. Antibody dilutions were prepared in PBS solution containing 1% NGS, 1% BSA, and 0.1% Triton X-100. The cells were then washed in PBS with 0.1% Triton X-100 and imaged in the same solution. Primary antibodies and working dilutions were as follows: $\alpha_{1C}$: Alomone, 1:1000; UC Davis/NIH NeuroMab Facility, clone N263/31, 1:200. RyR: Sigma Aldrich, 1:1000. $Ca_V62$: Alomone, 1:200. Rab7: Cell Signaling Technology, 1:100. Rab5: Cell Signaling Technology, 1:200. Lamp1: Developmental Studies Hybridoma Bank, created by the NICHD of the NIH and maintained at The University of Iowa, Department of Biology, Iowa City, IA 52242, 1:100. Secondary antibodies (Thermofisher) were used at a dilution of 1:1000.

Confocal Microscopy

Cells were plated onto 35 mm MatTek imaging dishes (MatTek Corporation). Images were captured on a Nikon A1RMP confocal microscope with a 40× oil immersion objective (1.3 N.A.). CFP, Alexa-488, YFP, and Alexa-647 were imaged using 458, 488, 514 and 639 nm laser lines, respectively.

Pulldown Assays

Transfected HEK293 cells cultured in 60 mm dishes were harvested in PBS, centrifuged at 2,000 g (4° C.) for 5 min, and the pellet resuspended in RIPA lysis buffer containing (mM): 150 NaCl, 20 Tris HCl, 1 EDTA, 0.1% (wt $vol^{-1}$) SDS, 1% Triton X-100, 1% sodium deoxycholate, and supplemented with protease inhibitor mixture (10 μL $mL^{-1}$, Sigma Aldrich), 1 PMSF, 2 N-ethylmaleimide, 05 PR-619 deubiquitinase inhibitor (LifeSensors). Cells were lysed on ice for 1 hr with intermittent vortexing and centrifuged at 10,000 g for 10 min (4° C.). The soluble lysate collected and protein concentration determined with the bis-cinchonic acid protein estimation kit (Pierce Technologies).

For $Ca_V\beta_{1b}$ pulldowns, lysates were precleared with 10 μL of protein A/G sepharose beads (Rockland) for 1 hr at 4° C. and then incubated with 2 μg anti-$Ca_V\beta_1$ antibody (UC Davis/NIH NeuroMab Facility, clone N7/18) for 1 hr at 4° C. Equivalent amounts of protein were then added to spin columns with 25 μL equilibrated protein A/G sepharose beads and rotated overnight at 4° C. Immunoprecipitates were washed a total of five times with RIPA buffer and then eluted with 30 μL elution buffer (50 mM Tris, 10% (vol $vol^{-1}$) glycerol, 2% SDS, 100 mM DTT, and 0.2 mg $mL^{-1}$ bromophenol blue) at 55° C. for 15 min. For $\alpha_{1C}$ pulldowns, lysates were added to spin columns containing 10 μL of equilibrated RFP-trap agarose beads, rotated at 4° C. for 1 hr, and then washed/eluted as described above. Proteins were resolved on a 4-12% Bis Tris gradient precast gel (Life Technologies) in MOPS-SDS running buffer (Life Technologies) at 200 V constant for −1 hr. Protein bands were transferred by tank transfer onto a polyvinylidene difluoride (PVDF, EMD Millipore) membrane in transfer buffer (25 mM Tris pH 8.3, 192 mM glycine, 15% (vol/vol) methanol, and 0.1% SDS). The membranes were blocked with a solution of 5% nonfat milk (BioRad) in Tris-buffered saline-tween (TBS-T) (25 mM Tris pH 7.4, 150 mM NaCl, and 0.1% Tween-20) for 1 hr at RT and then incubated overnight at 4° C. with primary antibodies ($Ca_V\beta_1$, UC Davis/NIH NeuroMab Facility. Actin, Sigma Aldrich) in blocking solution. The blots were washed with TBS-T three times for 10 min each and then incubated with secondary horseradish peroxidase-conjugated antibody for 1 hr at RT. After washing in TBS-T, the blots were developed with a chemiluminiscent detection kit (Pierce Technologies) and then visualized on a gel imager. Membranes were then stripped with harsh stripping buffer (2% SDS, 62 mM Tris pH 6.8, 0.8% β-mercaptoethanol) at 50° C. for 30 min, rinsed under running water for 2 min, and washed with TBST (3×, 10 min). Membranes were pre-treated with 0.5% glutaraldehyde and re-blotted with anti-ubiquitin (VU1, LifeSensors) as per the manufacturers' instructions.

Calcium Imaging

DRG neurons were washed twice in basal solution containing (mM): 145 NaCl, 5 KCl, 2 $CaCl_2$, 1 MgCl2, one sodium citrate, 10 HEPES, 10 D-glucose, pH 7.4, and incubated in the same solution containing 5 uM fura-2 with 0.05% Pluronic F-127 detergent (Life Technologies) for 1 hr at 37° C., 5% $CO_2$. Afterwards, cells were washed twice in same solution and placed on an inverted Nikon Ti-eclipse microscope with a Nikon Plan fluor 20× objective (0.45 N.A.). Fura-2 measurements were recorded at excitation wavelengths of 340 and 380 nm using EasyRatioPro (HORIBA Scientific). DRG neurons were depolarized with a solution in which NaCl was reduced to 110 mM and KCl increased to 40 mM.

Pancreatic β-cells were imaged with a similar protocol. Cells were maintained in a basal KRBH solution composed of (mM): 134 NaCl, 3.5 KCl, 1.2 $KH_2PO_4$, 0.5 $MgSO_4$, 1.5 $CaCl_2$, 5 $NaHCO_3$, 10 HEPES, 2.8 D-glucose, pH 7.4. Stimulation solutions included either 16.8 mM glucose or 40 mM KCl, with NaCl concentrations adjusted accordingly to balance osmolarity with KRBH solution.

Data and Statistical Analysis

Data were analyzed off-line using FloJo, PulseFit (HEKA), Microsoft Excel, Origin and GraphPad Prism software. Statistical analyses were performed in Origin or GraphPad Prism using built-in functions. Statistically significant differences between means ($p<0.05$) were determined using Student's t test for comparisons between two groups or one-way ANOVA for three groups, with Tukey's post-hoc analysis. Data are presented as means±s.e.m.

Example 2

Isolation and Characterization of CaVβ-Targeted Nanobodies

Figure 1B:
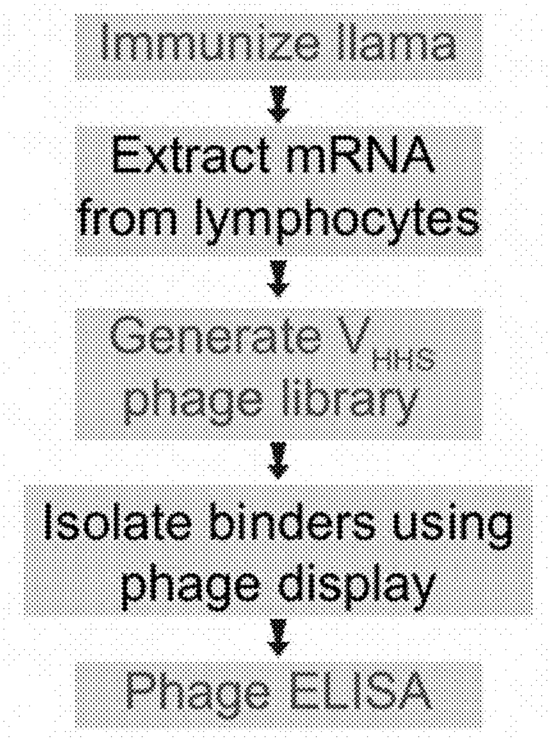
Figure 1C:
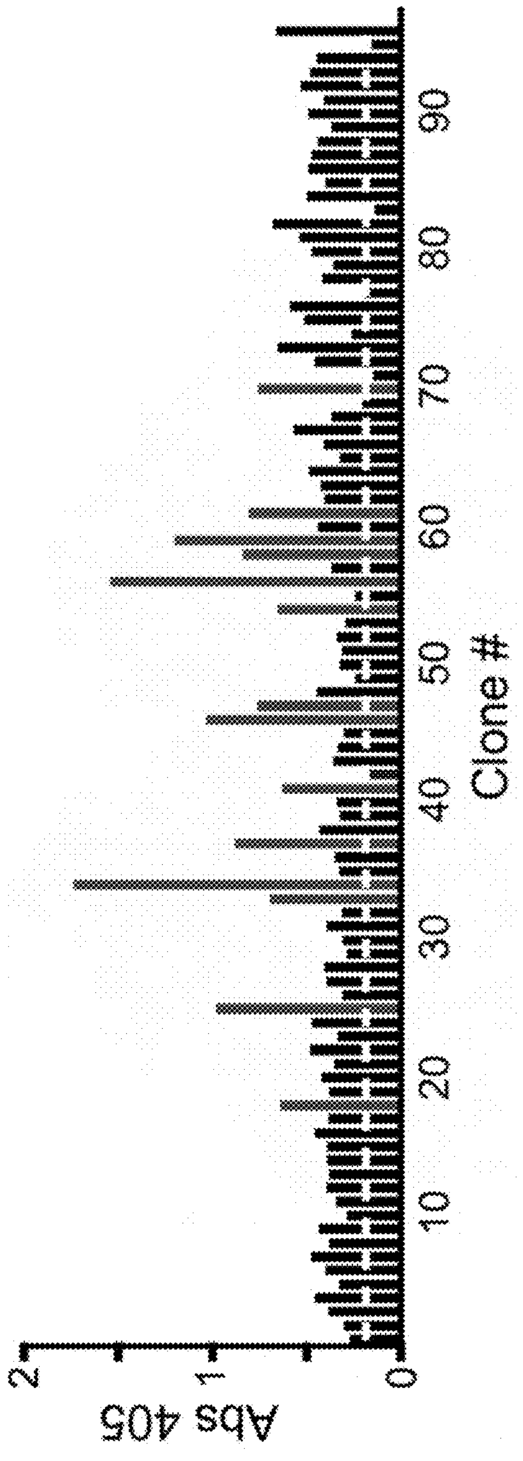
Figure 1D:
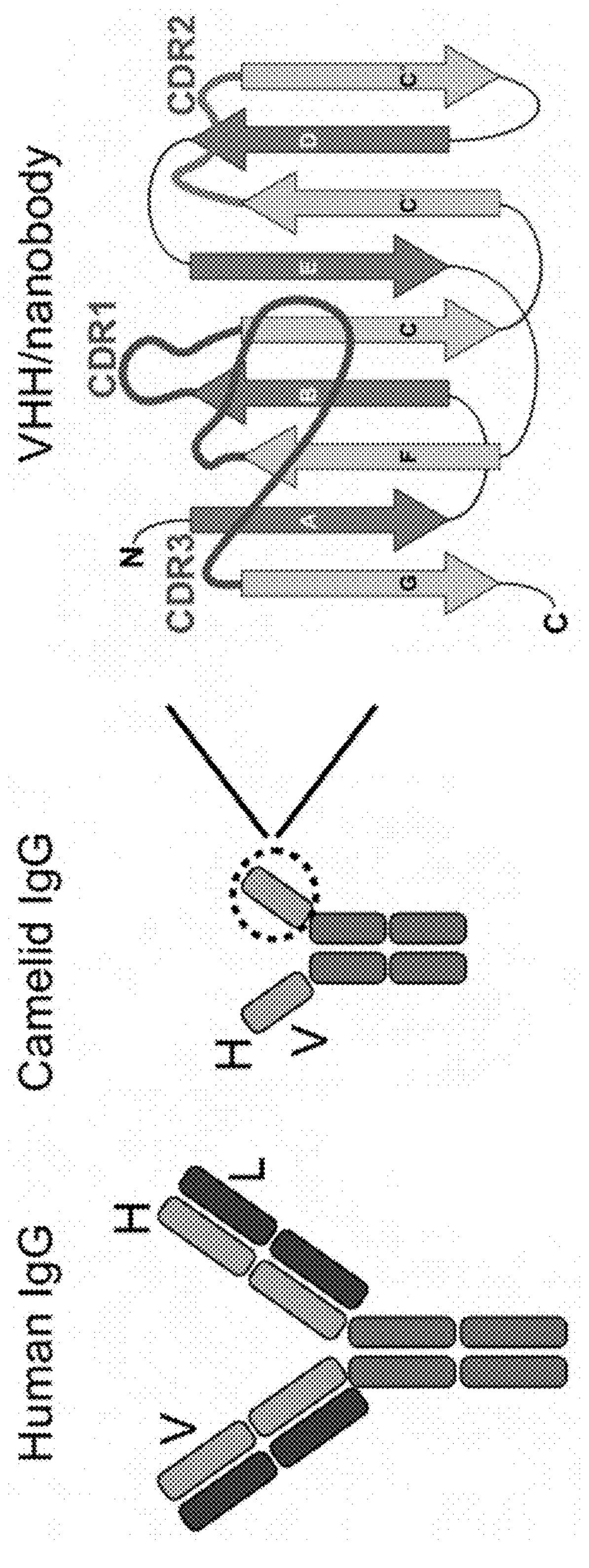

The present disclosure developed a nanobody targeted to $Ca_V\beta$s that would be incorporated into $Ca_V$ channel complexes but be functionally silent, to serve as a vehicle to potentially address distinct enzymatic moieties or sensors to endogenous channels. $Ca_V\beta_{1b}$ and $Ca_V\beta_3$ were expressed in HEK293 cells using BacMam expression and purified the proteins using affinity purification, ion exchange, and size exclusion chromatography (FIG. 1A). Purified $\delta_1$ and $\beta_3$ (1 mg each) were used for llama immunization, and successful serum conversion was confirmed by ELISA (not shown). Messenger RNA was extracted from isolated lymphocytes, PCR-amplified and cloned into a plasmid vector (pComb3XSS) to generate a $V_{HHS}$ phage library (FIG. 1B). Putative nanobody binders were enriched from the phage library using three rounds of phage display and panning (Pardon et al., 2014). A 96-well ELISA was performed on enriched phage libraries and selected 14 positive clones for sequencing (FIG. 10). At least seven distinct classes of nanobody binders were identified based on the unique sequences within complementarity determining regions (CDR1-3), the major determinants of antigen binding (FIGS. 1D and 1E). Sequence information of twenty-five nanobodies identified was summaried below in Table 1.

Figure 1F:
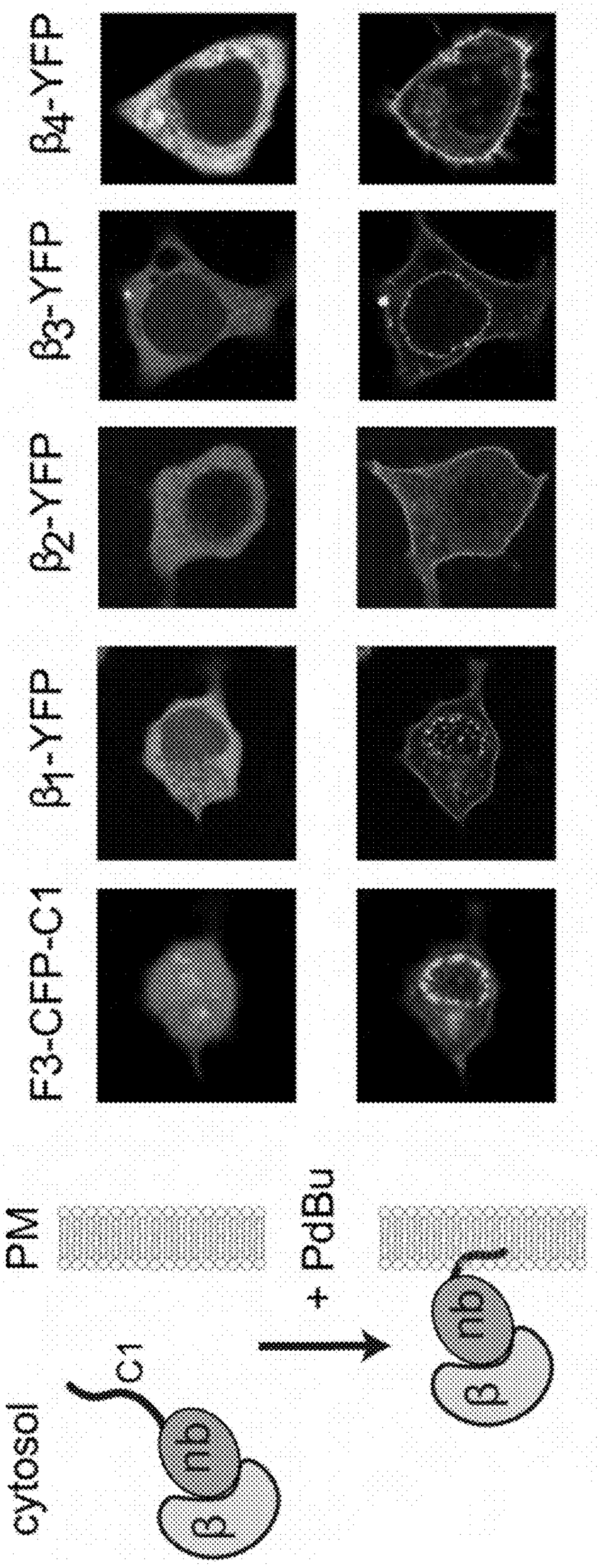
Figure 1G:
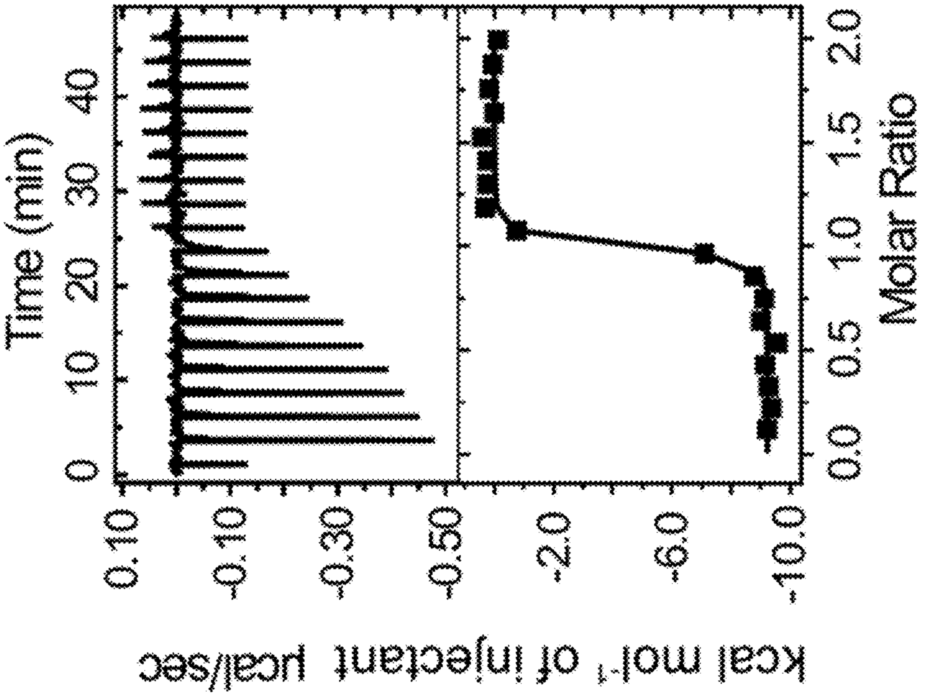
Figure 7:
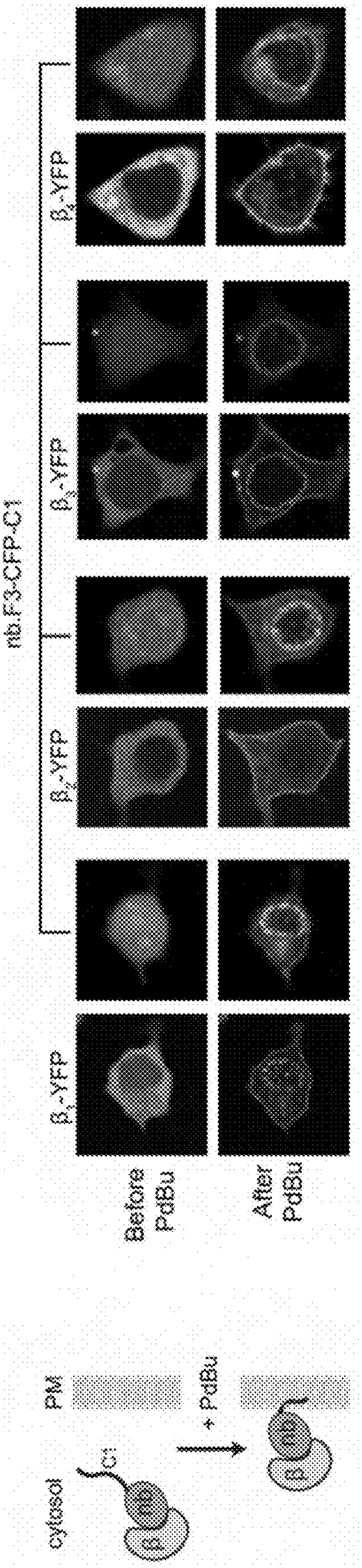
FIG. 7 shows that nb.F3 binds all four $Ca_V\beta$ subunits in the cytosol of mammalian cells. Left, is a schematic of the phorbol ester 12,13-dibutyrate (PdBu) translocation assay. Right, shows confocal images of HEK293 cells expressing nb.F3-CFP-$C1_{PKC\gamma}$ and a YFP-$Ca_V\beta$ before (top) and after (bottom) the addition of 1 μM Pdbu.
Figure 8A:
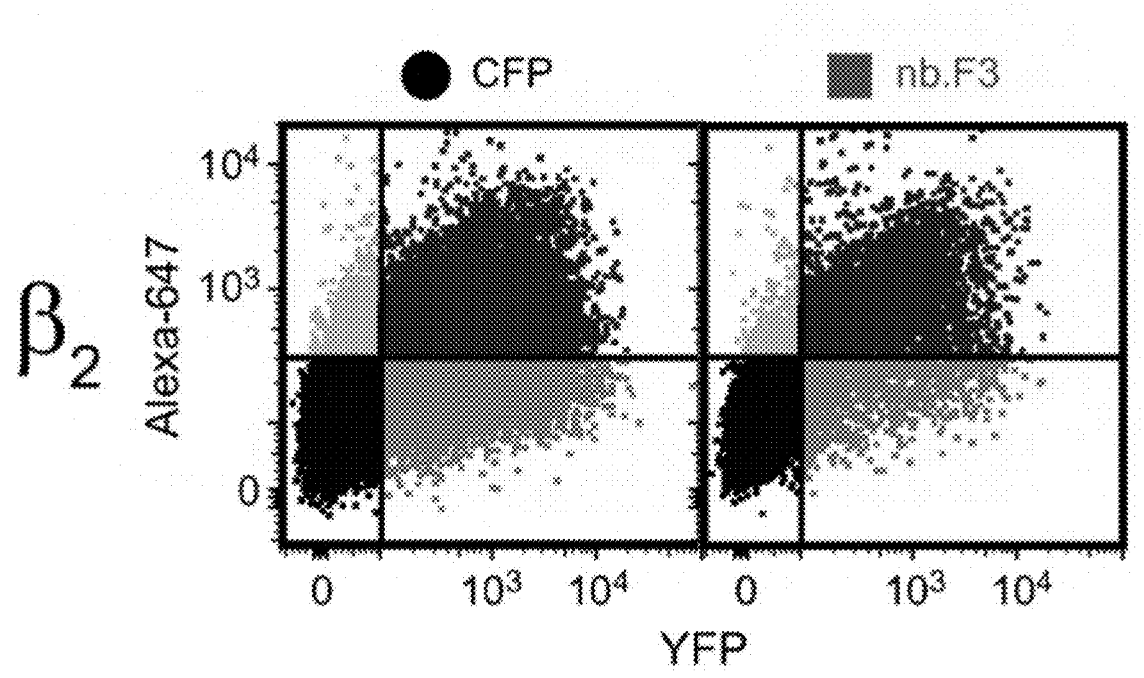
FIGS. 8A-8F show representative flow cytometry data for BBS-$\alpha_{1B}$ with YFP-$Ca_V\beta_2$-$Ca_V\beta_4$.
Figure 8B:
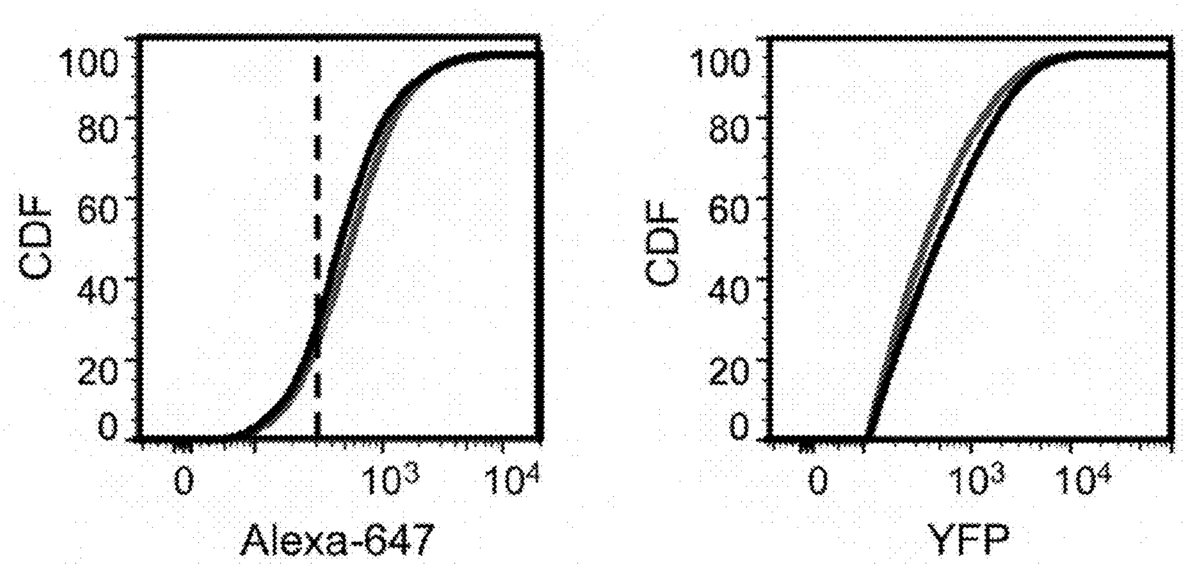
Figure 8C:
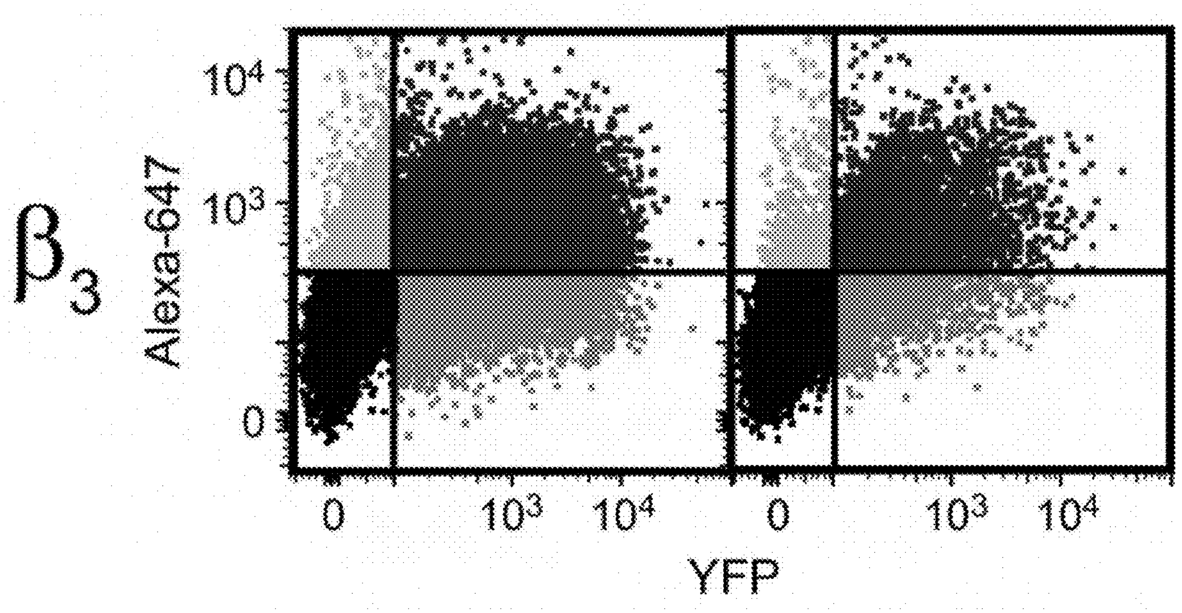
Figure 8D:
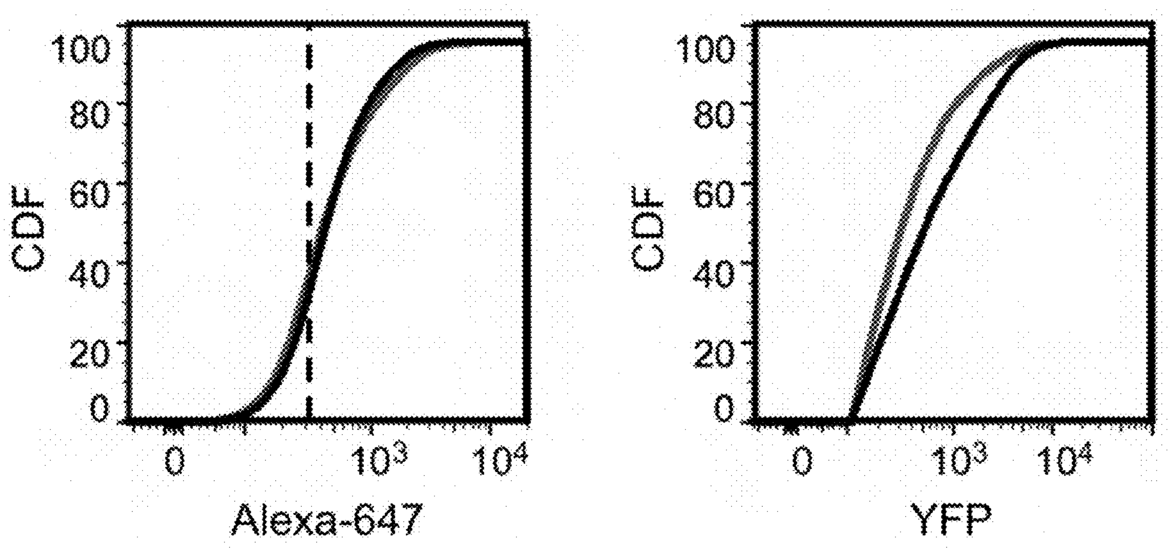
Figure 8E:
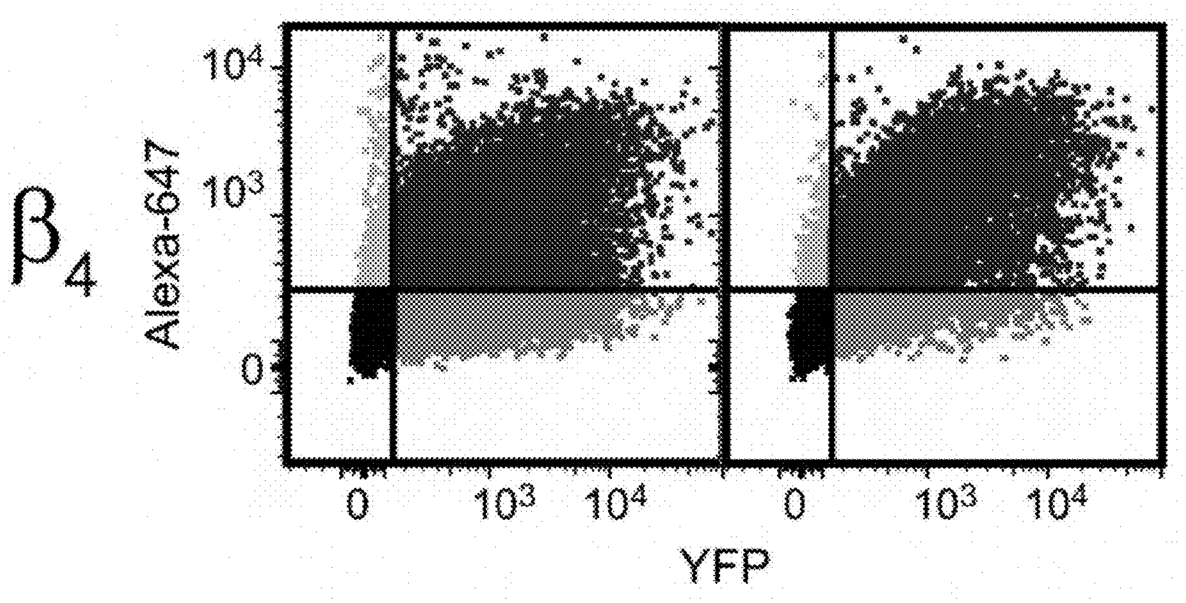
Figure 8F:
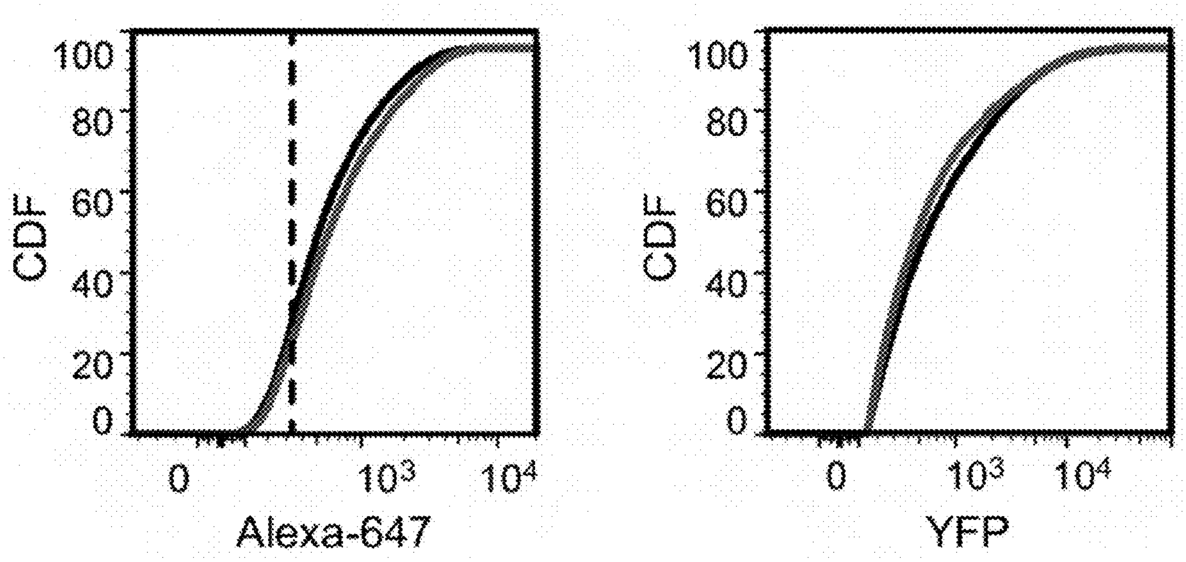
Figure 9A:
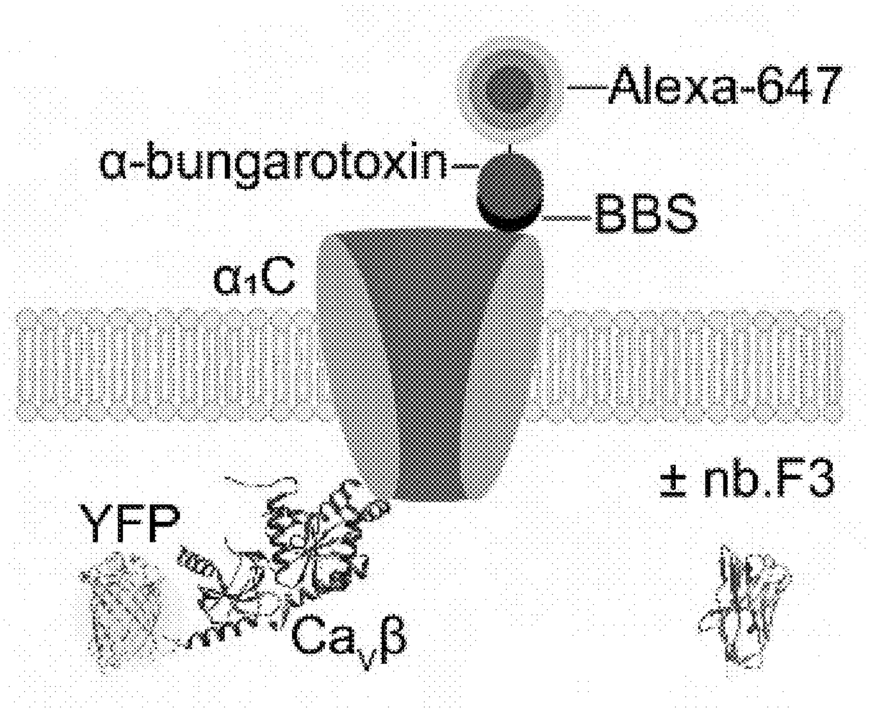
FIGS. 9A-9E show that nb.F3 is functionally silent on reconstituted $Ca_V1.2$ channels.
Figure 9B:
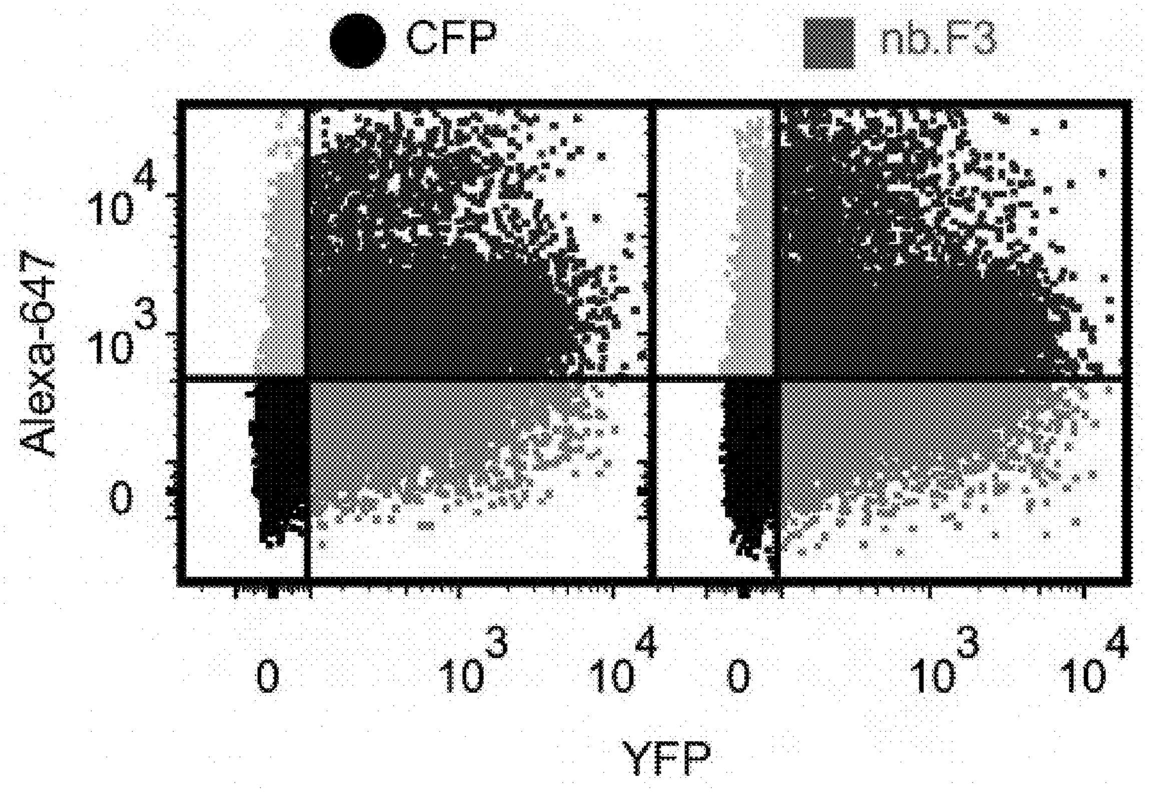
Figure 9C:
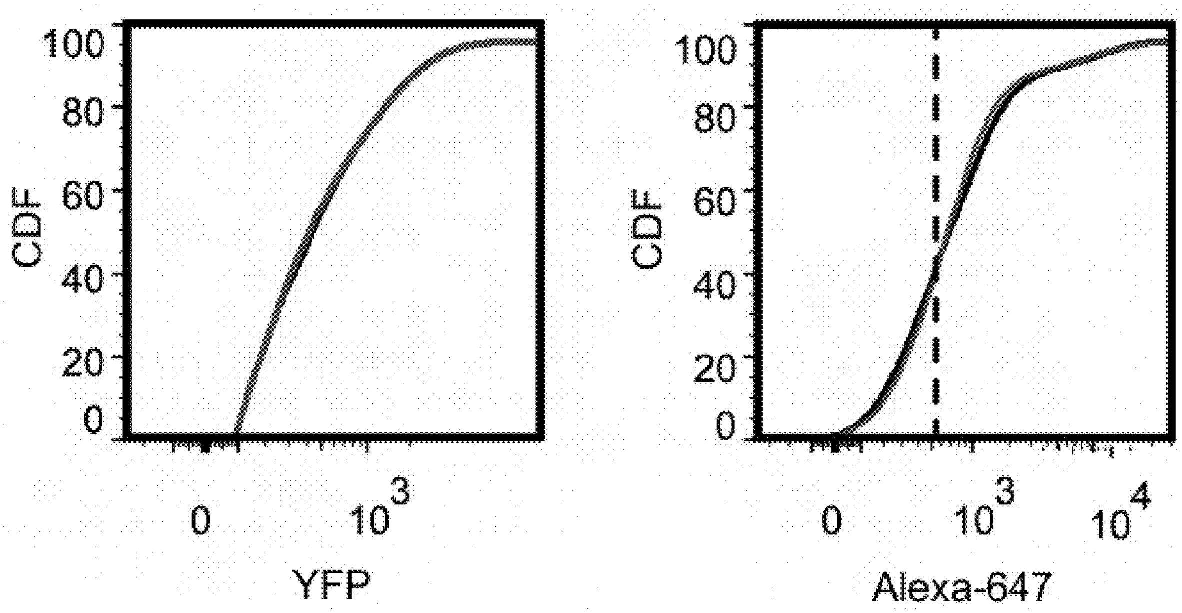
Figure 9D:
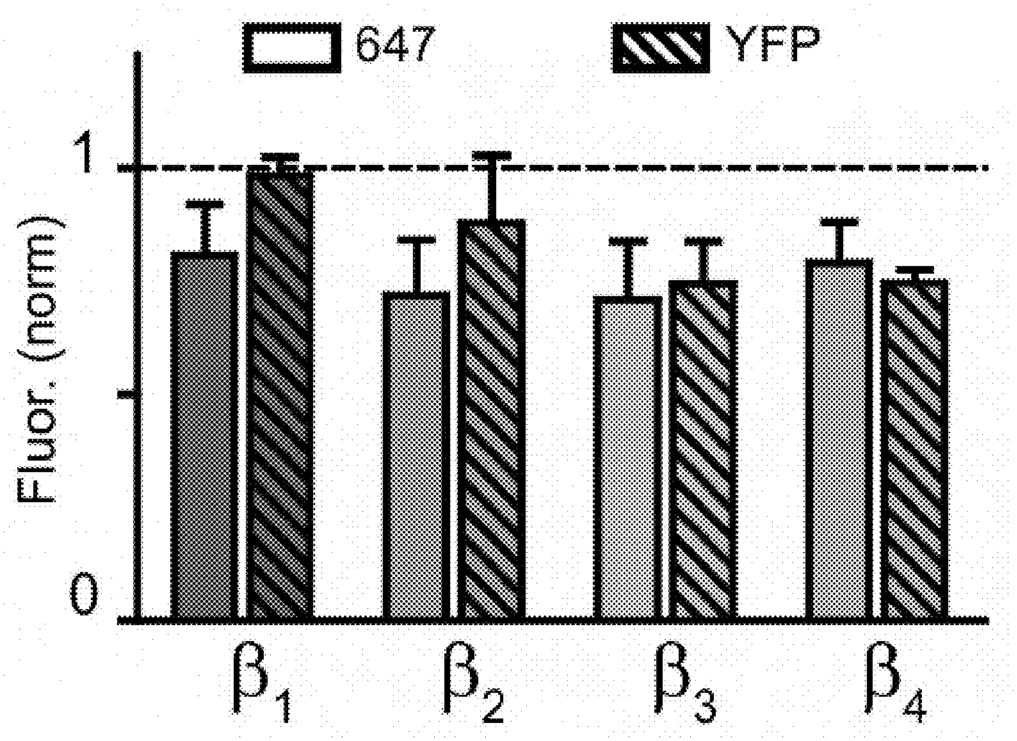
Figure 9E:
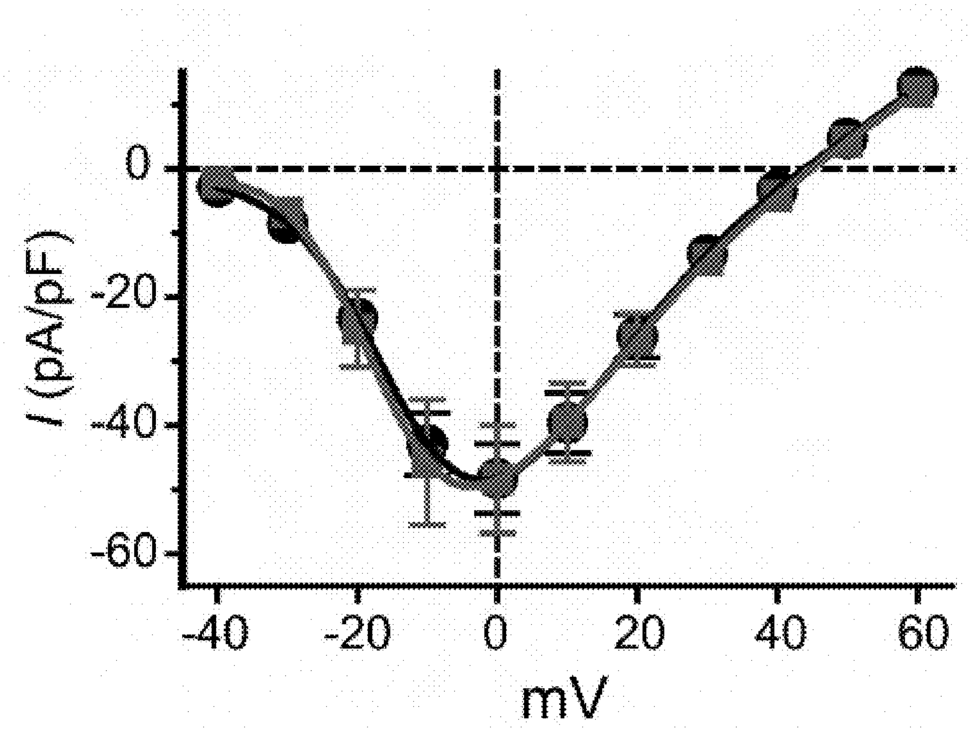
Figure 10A:
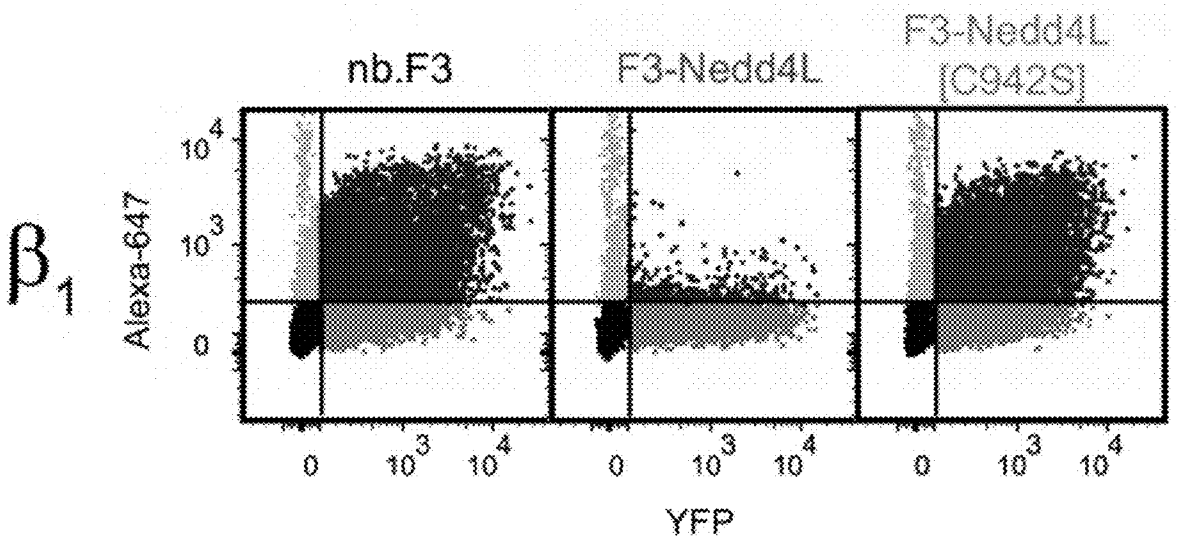
FIGS. 10A-10H show representative flow cytometry data for $Ca_V$-aβlation of BBS-$\alpha_{1B}$ with YFP-$Ca_V\beta_2$-$Ca_V\beta_4$.
Figure 10B:
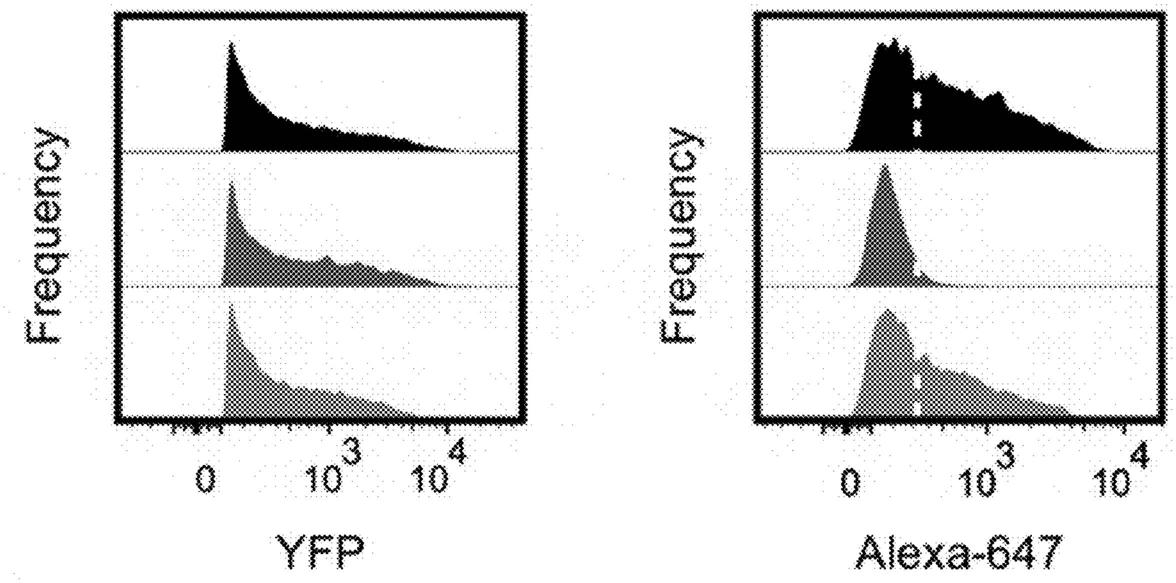
Figure 10C:
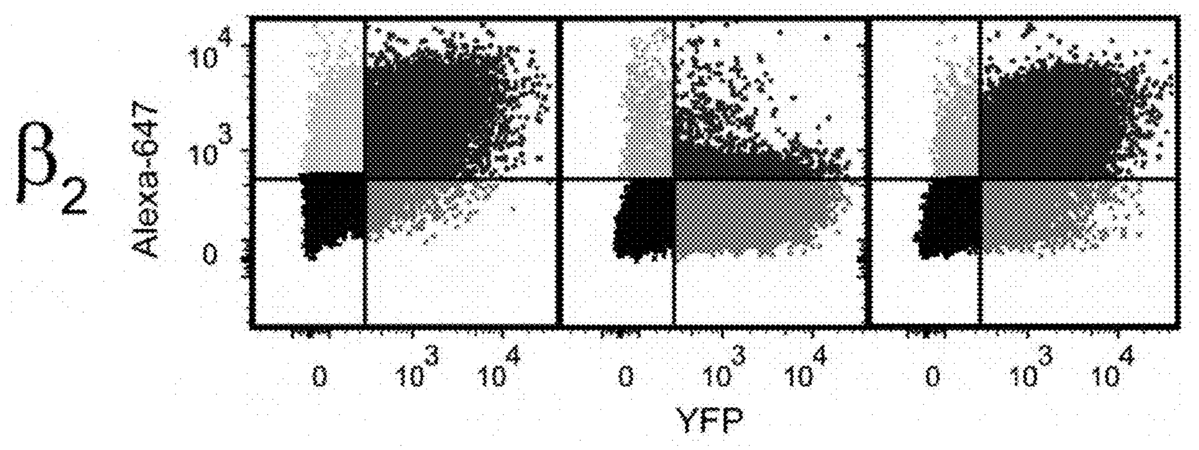
Figure 10D:
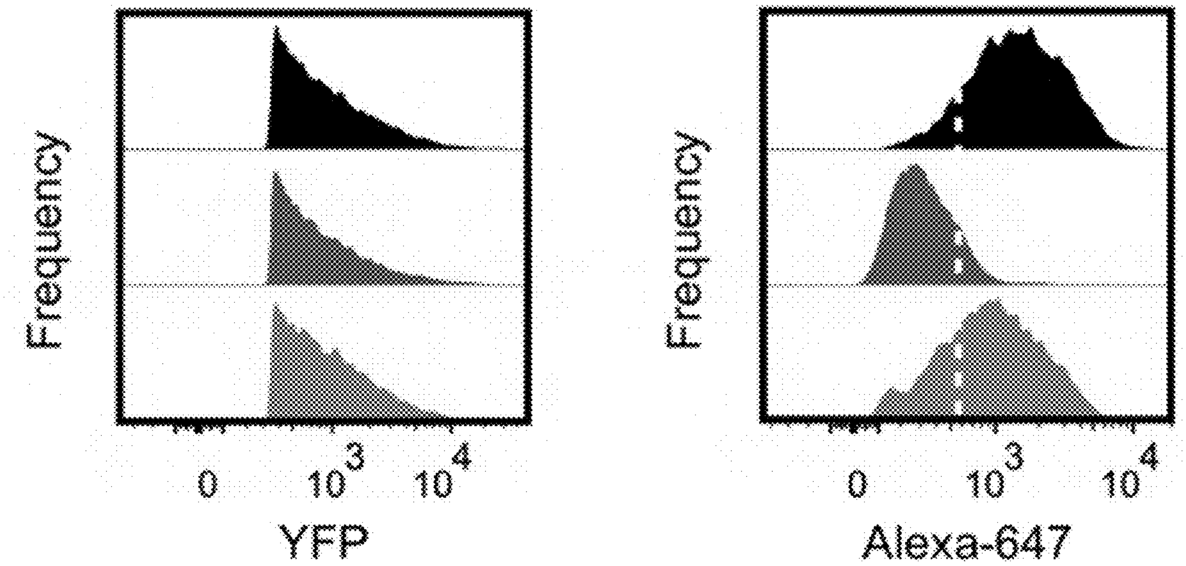
Figure 10E:
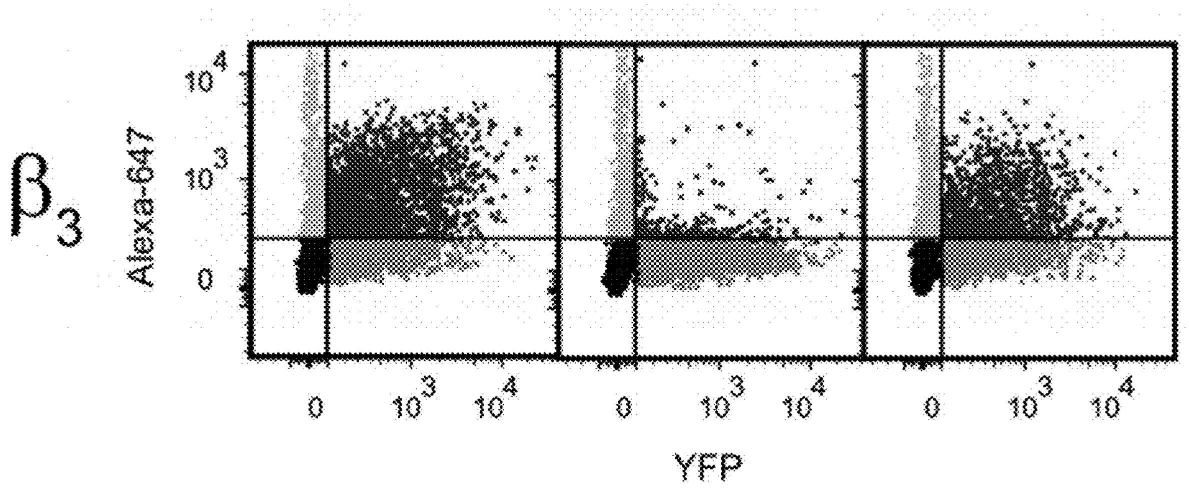
Figure 10F:
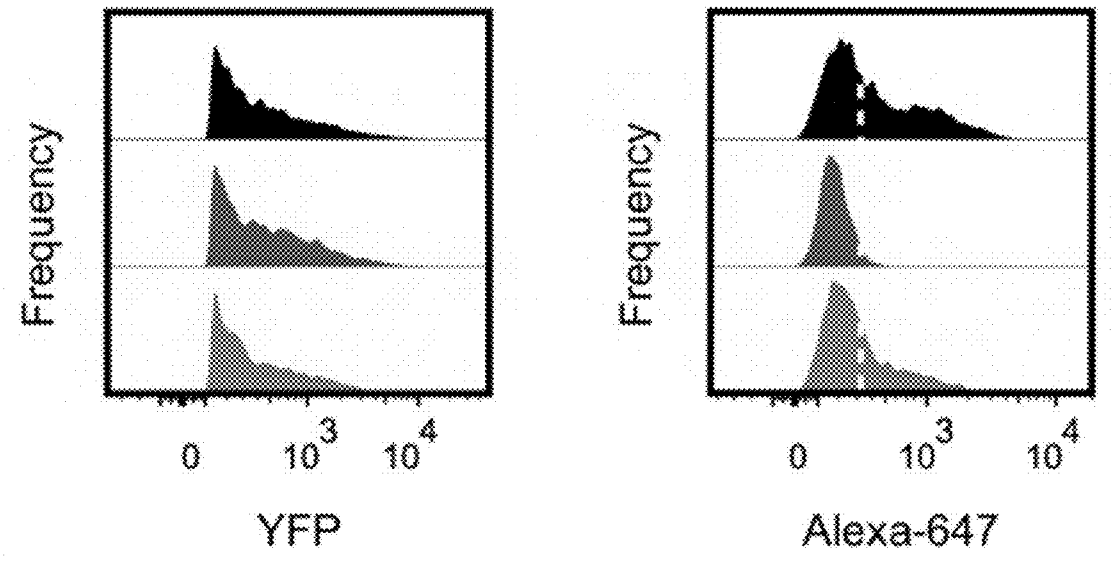
Figure 10G:
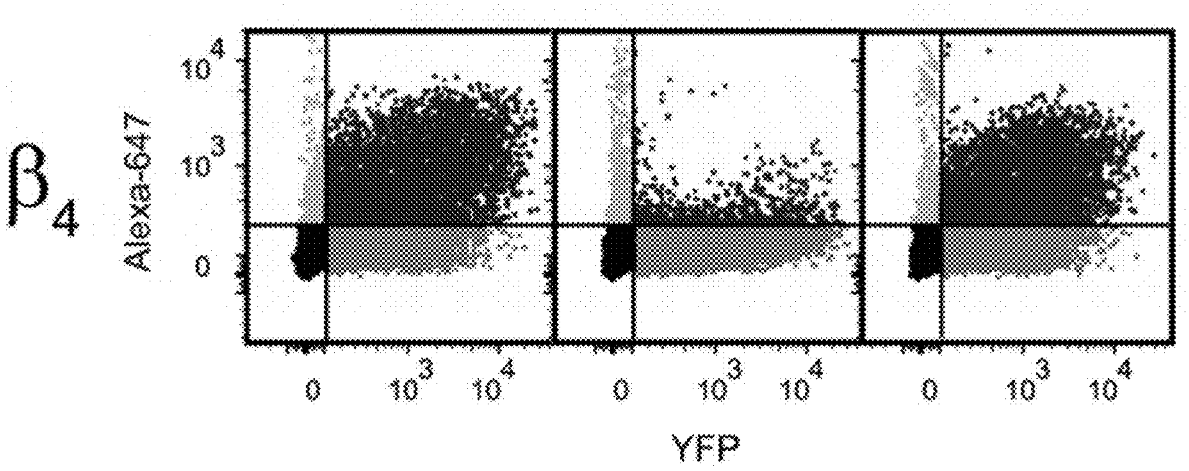
Figure 10H:
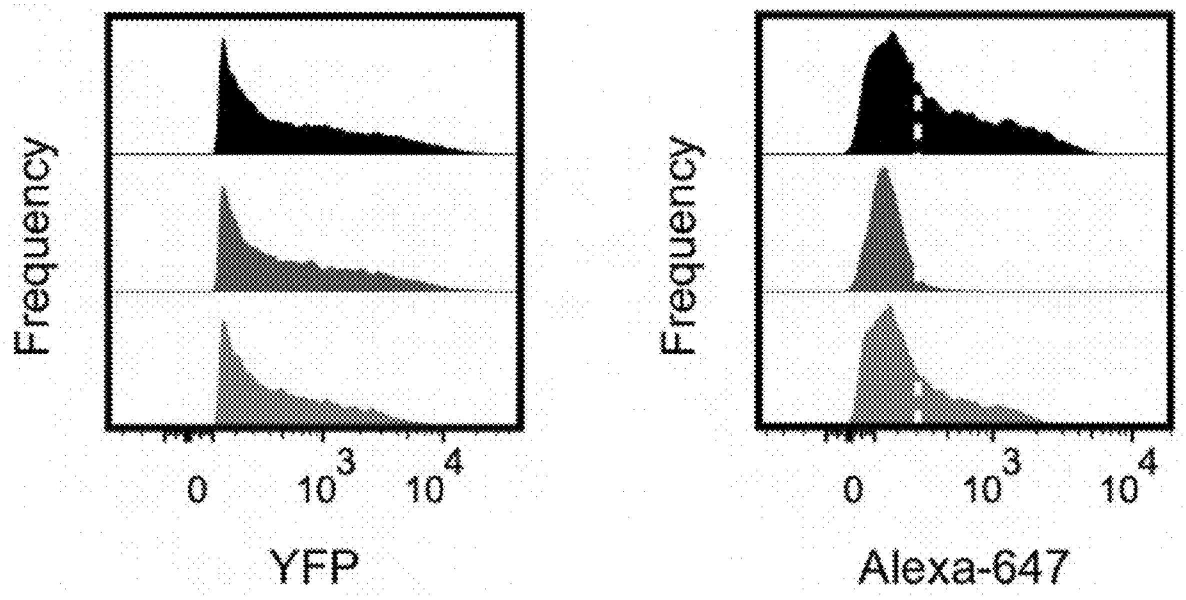
Figure 11A:
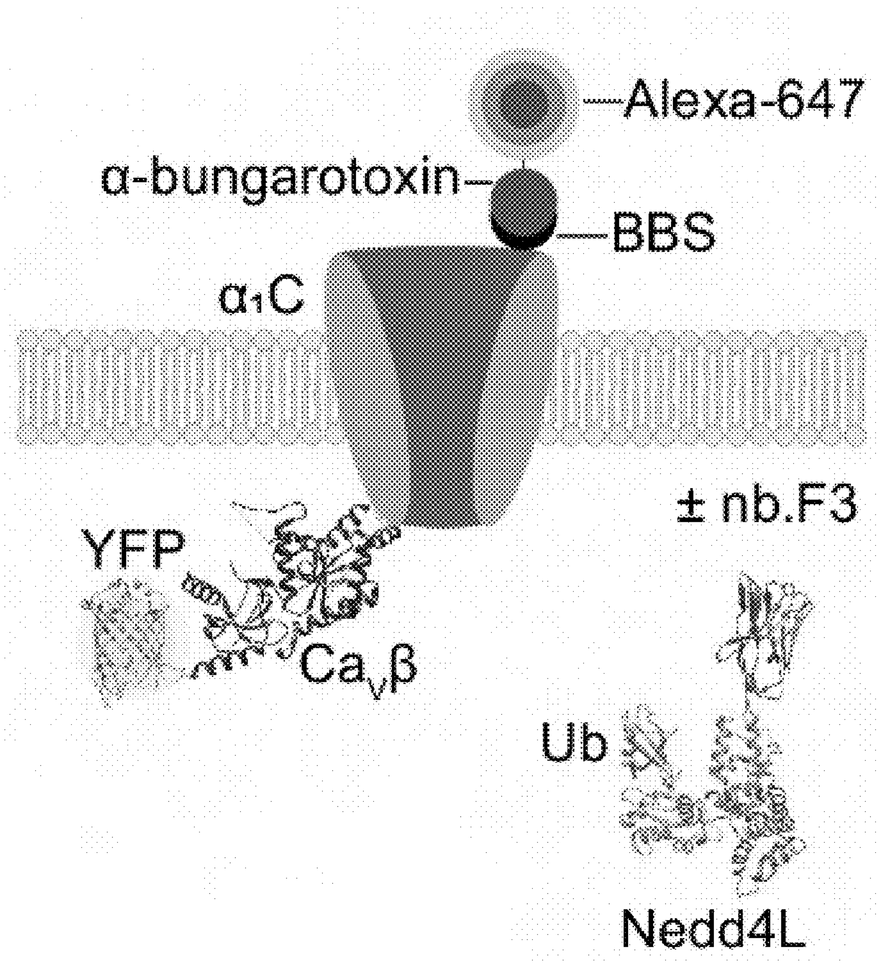
FIGS. 11A-11D show the functional impact of a chimeric nb.F3-Nedd4L protein ($Ca_V$-aβlator) on reconstituted $Ca_V1.2$ channels.
Figure 11B:
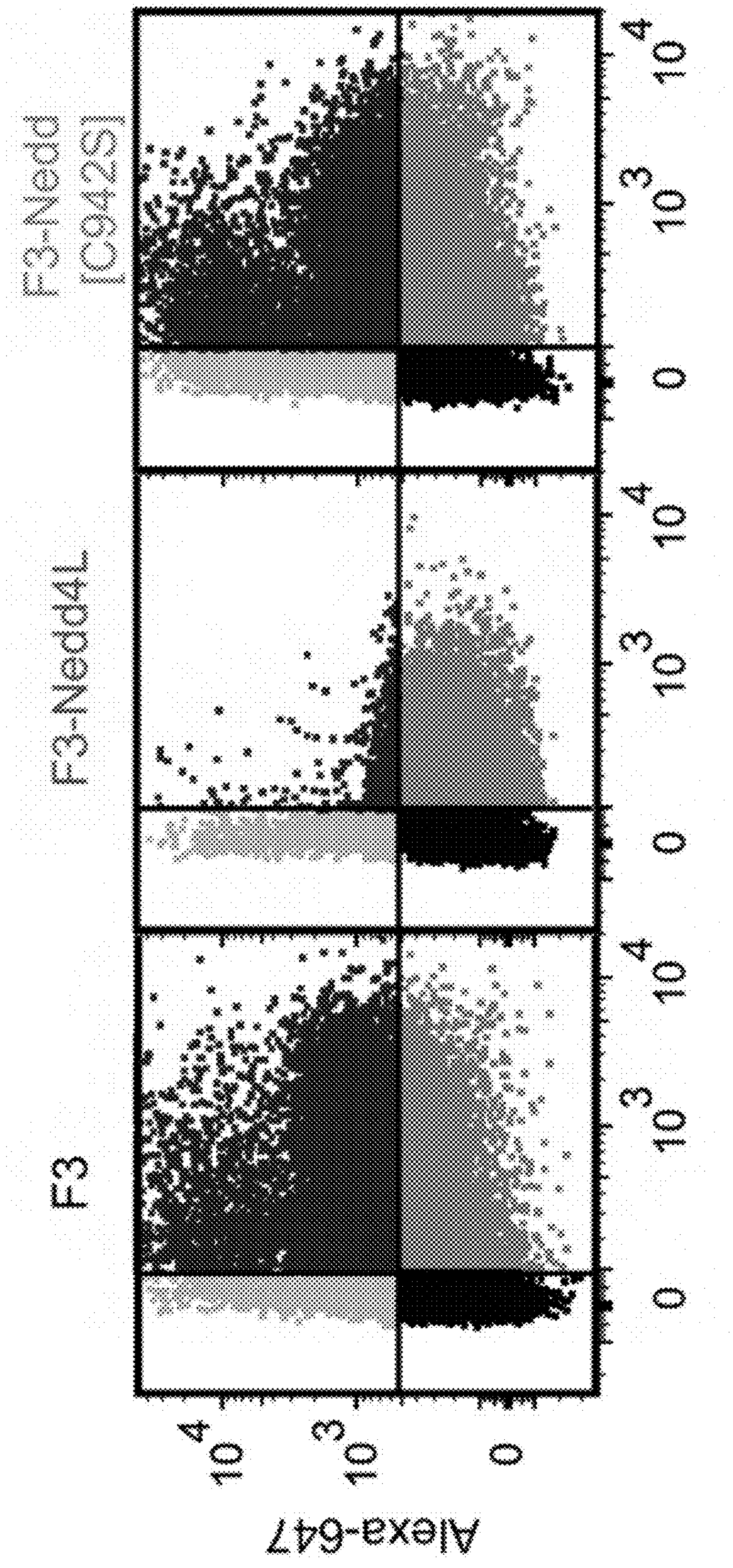
Figure 11C:
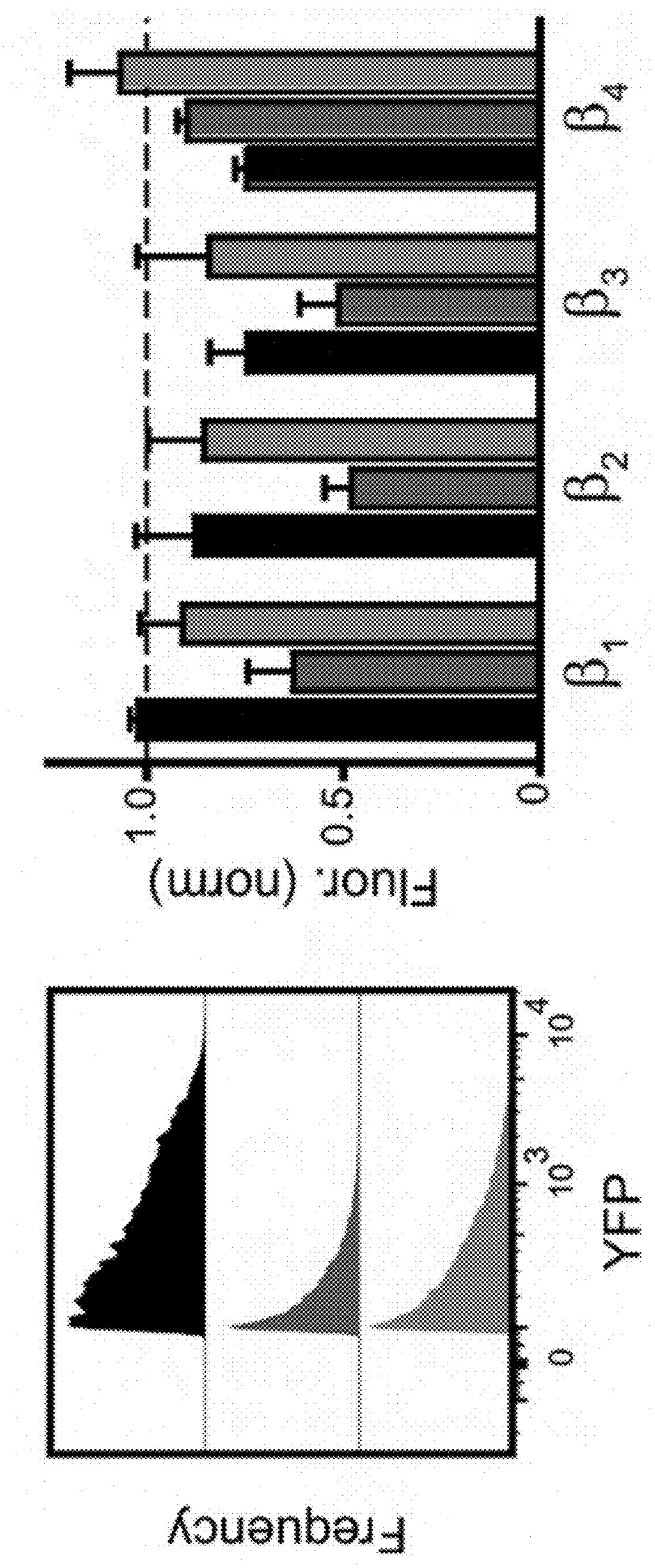
Figure 11D:
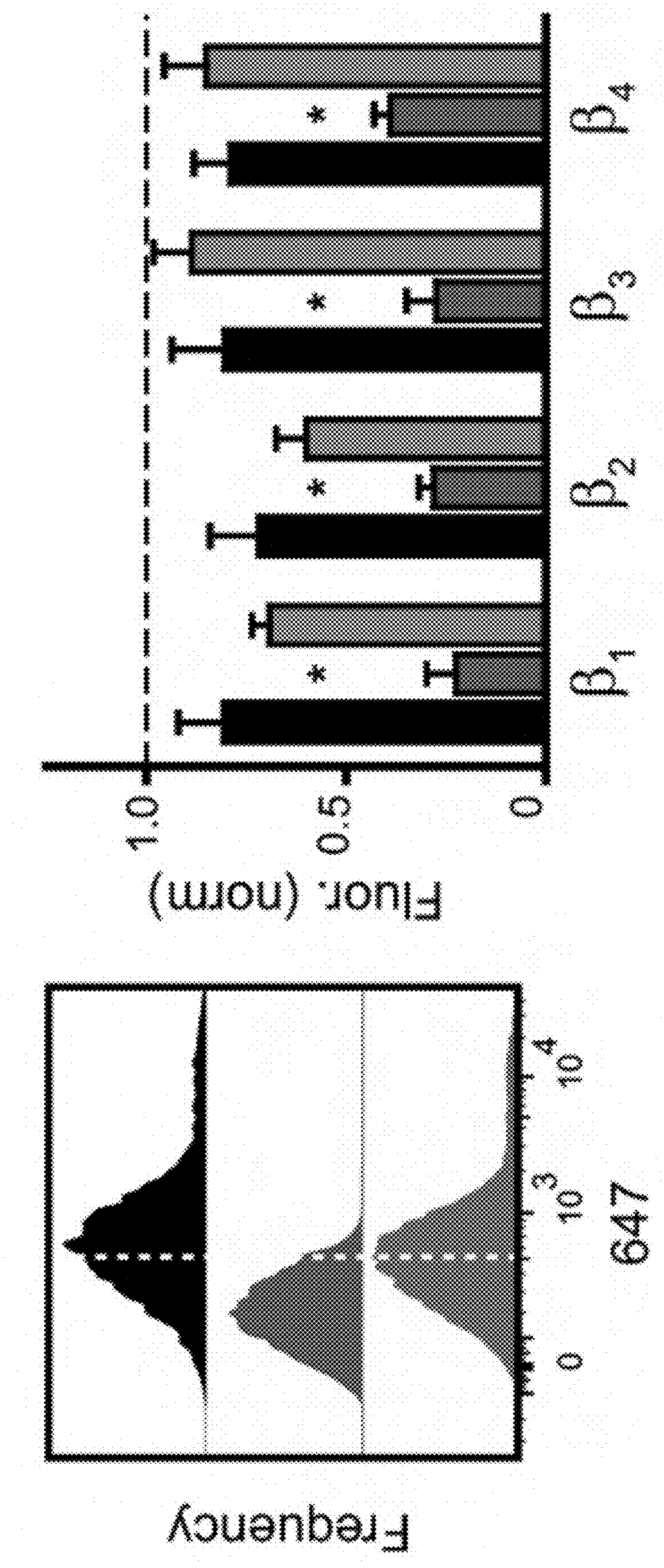
Figure 12A:
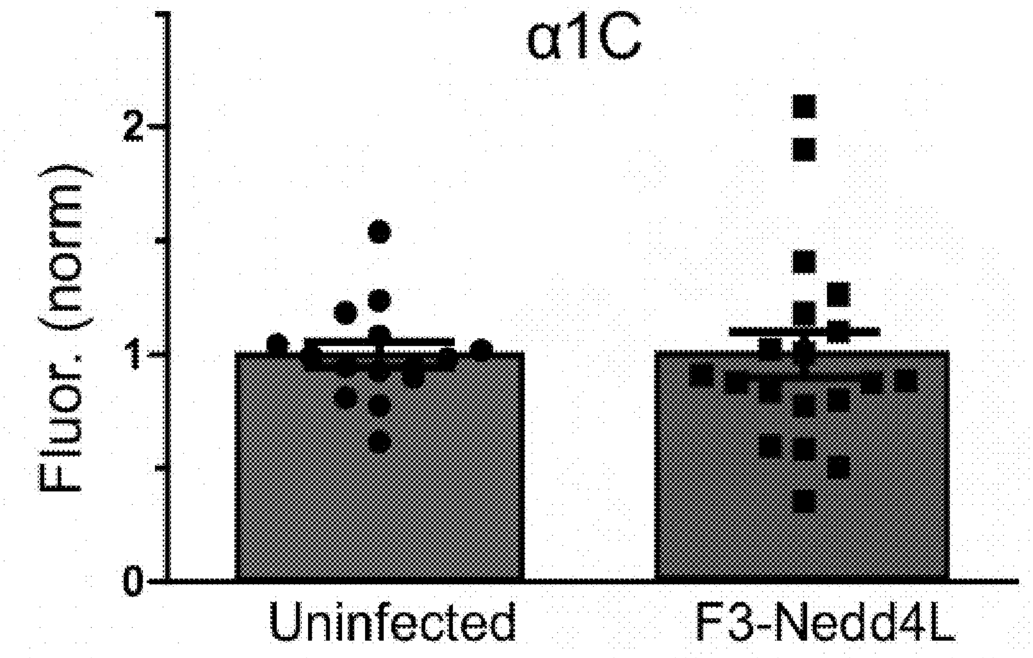
FIGS. 12A-12D show that $Ca_V$-aβlator does not redistribute $\alpha_{1C}$ to Rab5 early-endosomes or lysosomes, nor decrease total levels of $\alpha_{1C}$ or $\beta_2$.
Figure 12B:
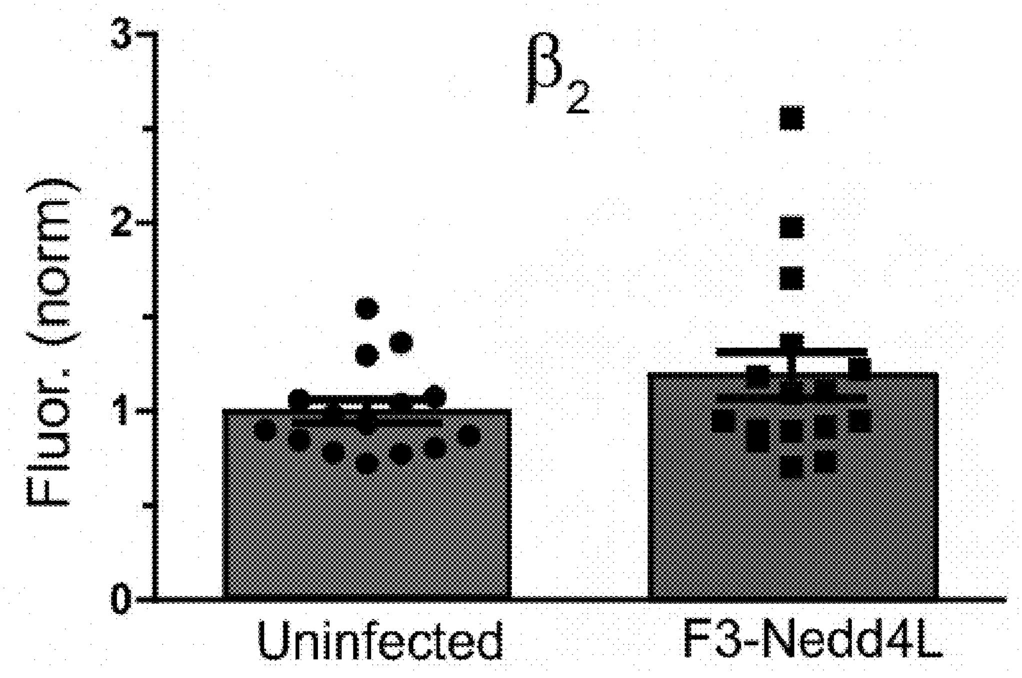
Figure 12C:
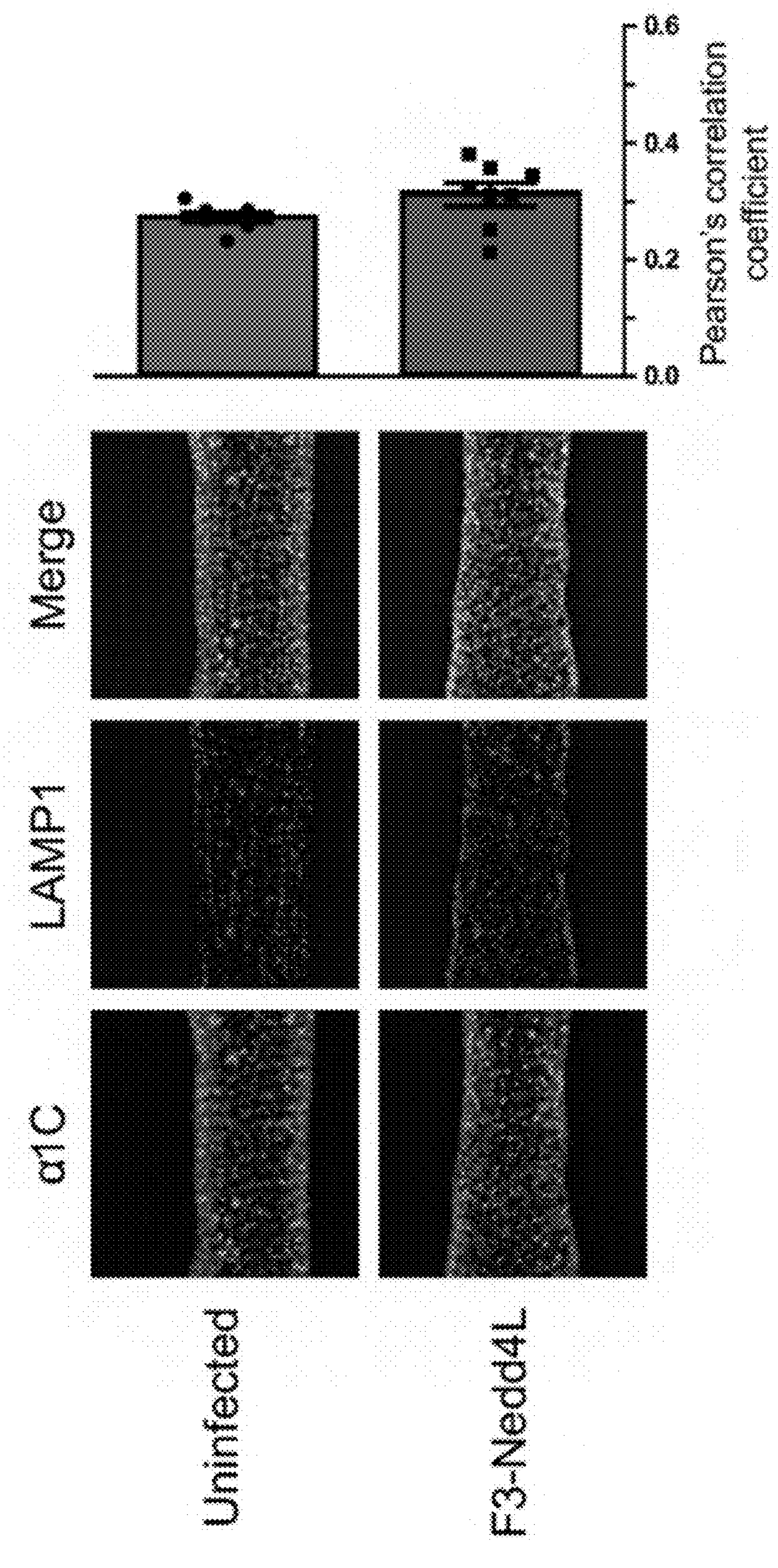
Figure 12D:
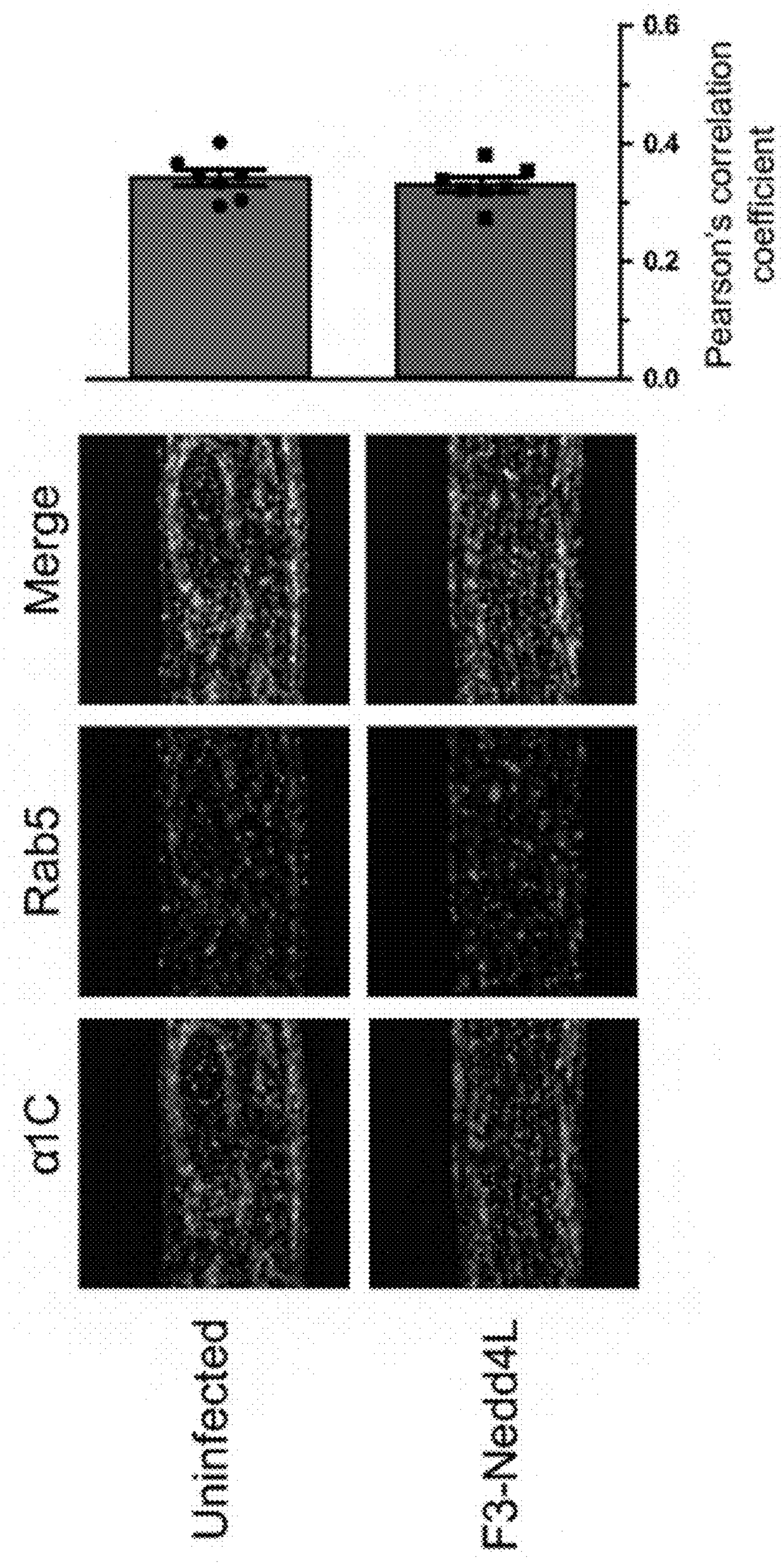

A small-molecule-induced fluorescence co-translocation assay was adopted to simultaneously determine whether: (1) individual nanobodies were well-behaved when expressed in mammalian cells (i.e. do not aggregate), and (2) bound $Ca_V\beta$s. A tripartite construct consisting of individual nanobodies fused to CFP and the 01 domain of PKCγ was cloned into a CMV expression vector and transiently co-transfected with YFP-tagged $Ca_V\beta$s into HEK293 cells. After pilot experiments, we chose one nanobody clone, nb.F3, for in-depth characterization and development. Both nb.F3-CFP-C1 and YFP-$\beta_1$ were uniformly expressed in the cytosol of transfected HEK293 cells (FIG. 1F). Application of 1 μM phorbol-12,13-dibutyrate (PdBu) led to the rapid and dramatic redistribution of nb.F3-CFP-C1 from the cytosol to the plasma and nuclear membranes (FIG. 1F). Reassuringly, YFP-$\beta_1$ concomitantly redistributed to the plasma and nuclear membranes, providing a convenient visual confirmation that it associates with nb.F3 inside cells (FIG. 1F). Similar experiments conducted with the other $Ca_V\beta$s ($\beta_2$-$\beta_4$) showed that they all bind with nb.F3-CFP-C1 in cells (FIG. 1F, FIG. 7), indicating the nanobody interacts with an epitope conserved among $Ca_V\beta$s. Isothermal titration calorimetry using purified nb.F3 and $Ca_V\beta_{2b}$ indicated a high-affinity ($K_d$=13.2±7.2 nM) interaction and a 1:1 stoichiometry (FIG. 1G).

Figure 2A:
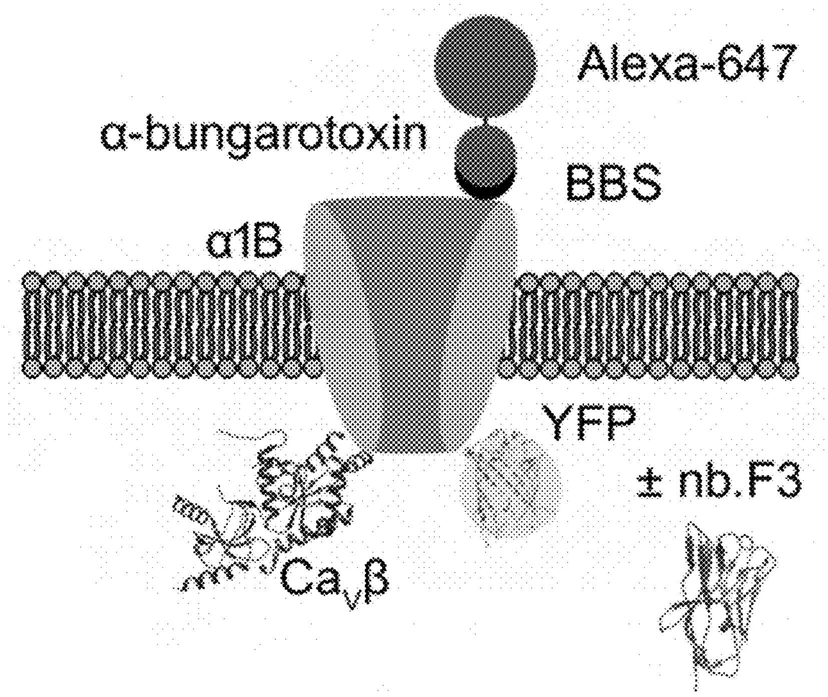
FIGS. 2A-2L show that nb.F3 is functionally silent on reconstituted $Ca_V2.2$ channels.
Figure 2B:
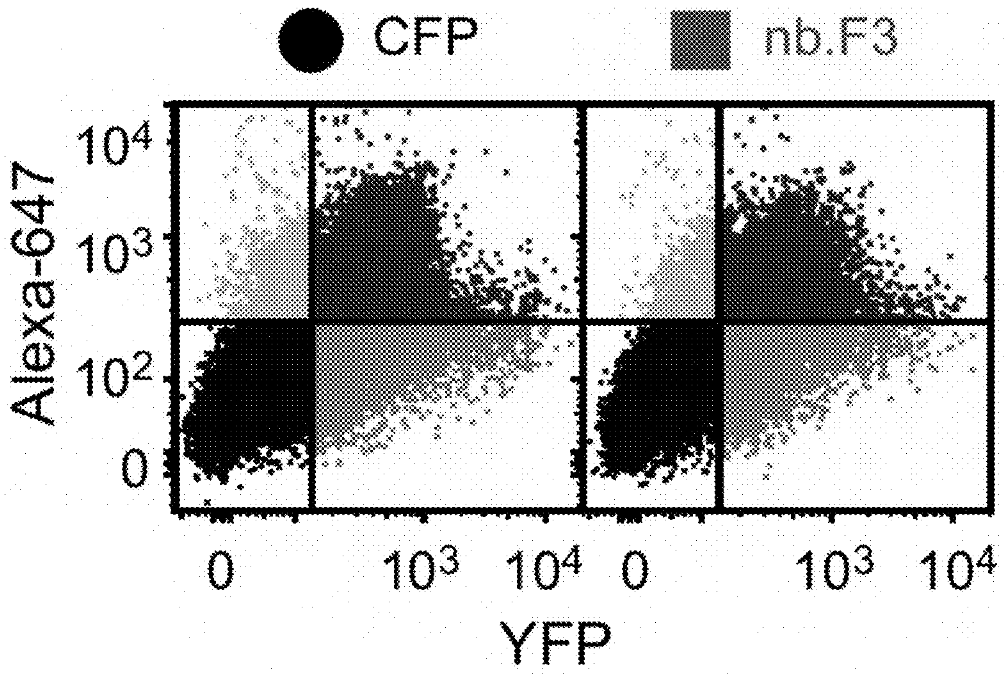
Figure 2C:
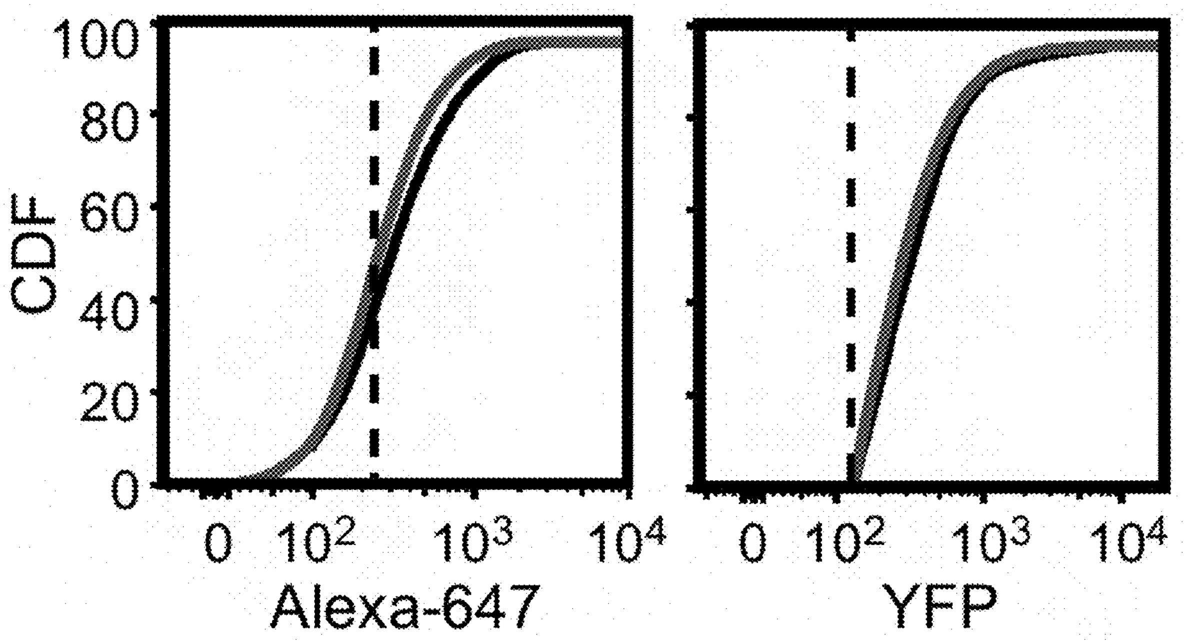
Figure 2D:
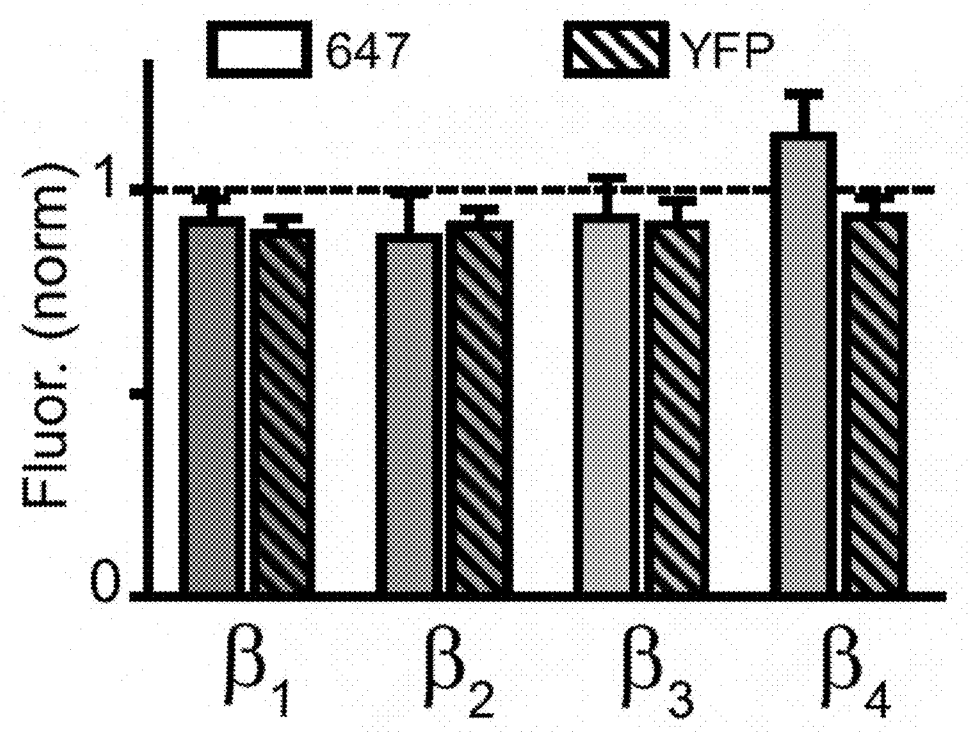

It was important to the overall strategy that nb.F3 incorporate into assembled HVACC complexes without impacting channel function or subunit stability. A flow cytometry assay was used to assess the impact of nb.F3 on recombinant $Ca_V2.2$ trafficking, subunit expression levels, and whole-cell currents, all of which are known to be regulated by $Ca_V13$ (FIGS. 2A-2L) (Waithe et al., 2011). An engineered $\alpha_{1B}$ harboring two tandem high-affinity bungarotoxin-binding sites (2XBBS) in the extracellular domain IV S5-S6 loop and a C-terminus YFP tag was used to enable simultaneous detection of surface (Alexa647-conjugated bungarotoxin) and total (YFP fluorescence) channel populations in non-permeabilized cells (FIG. 2A). BBS-$\alpha_{1B}$-YFP and $Ca_V13$ were co-expressed either with or without nb.F3-P2A-CFP and utilized flow cytometry to rapidly measure surface and total channel expression. In cells expressing BBS-$\alpha_{1B}$-YFP and $\beta_{1b}$, nb.F3 had no impact on Alexa647 or YFP fluorescence compared to control (FIGS. 2B-2D), indicating no disruption of channel trafficking or effect on $\alpha_{1B}$ expression. Similar results regarding the inertness of nb.F3 on $\alpha_{1B}$ trafficking and stability were obtained when $Ca_V2.2$ was reconstituted with the other $Ca_V13$ ($\delta_2$-$\beta_4$) subunits (FIG. 2D).

Figure 2E:
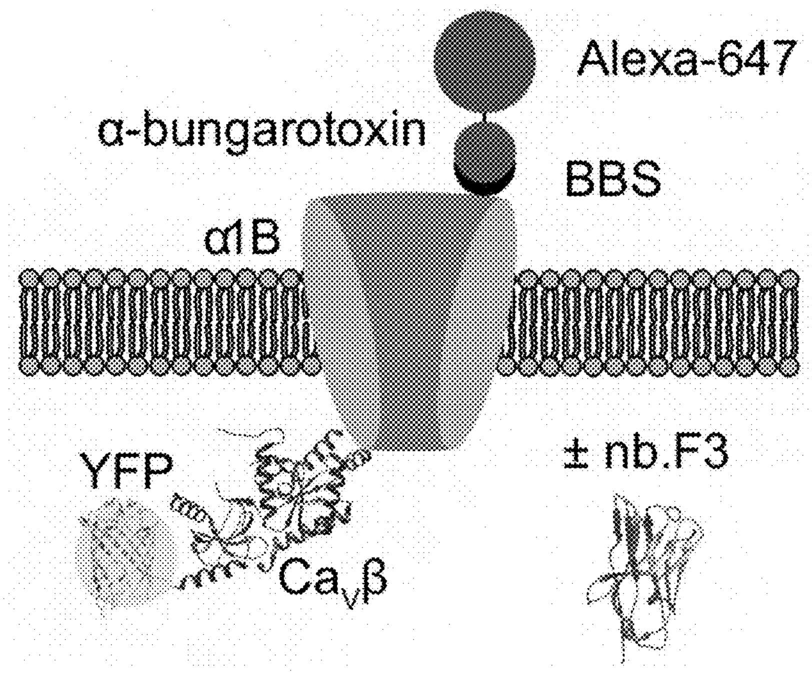
Figure 2F:
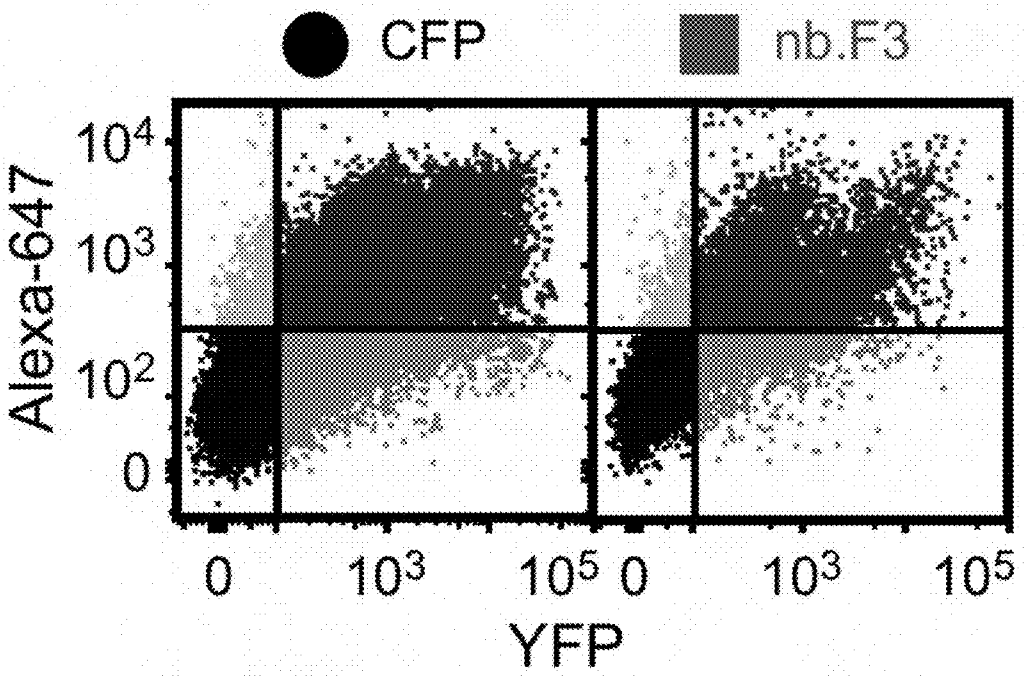
Figure 2G:
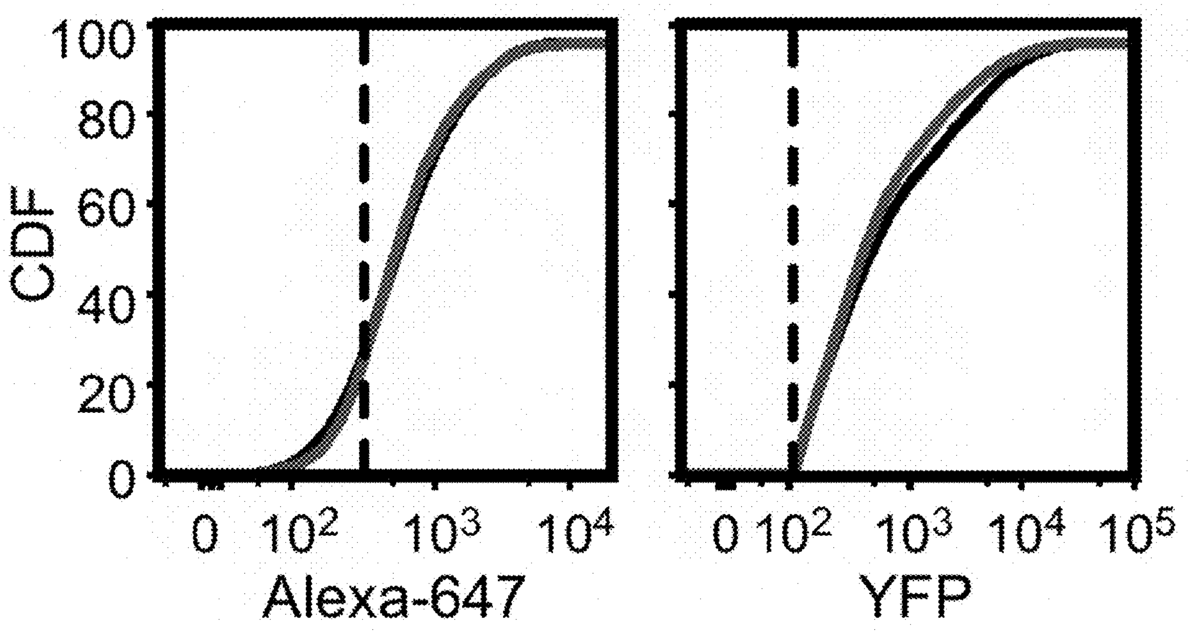
Figure 2H:
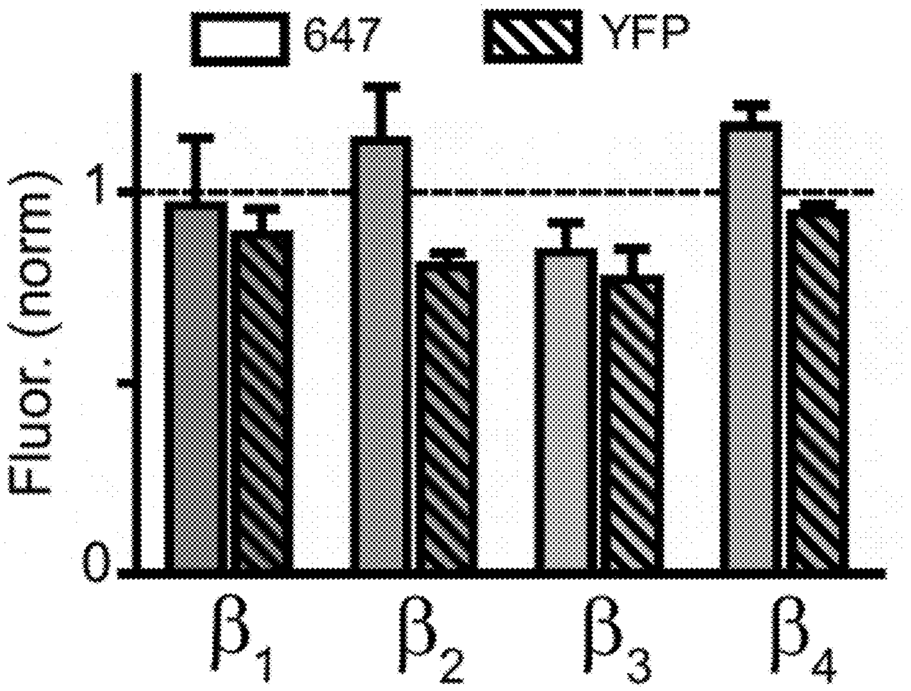
Figure 2I:
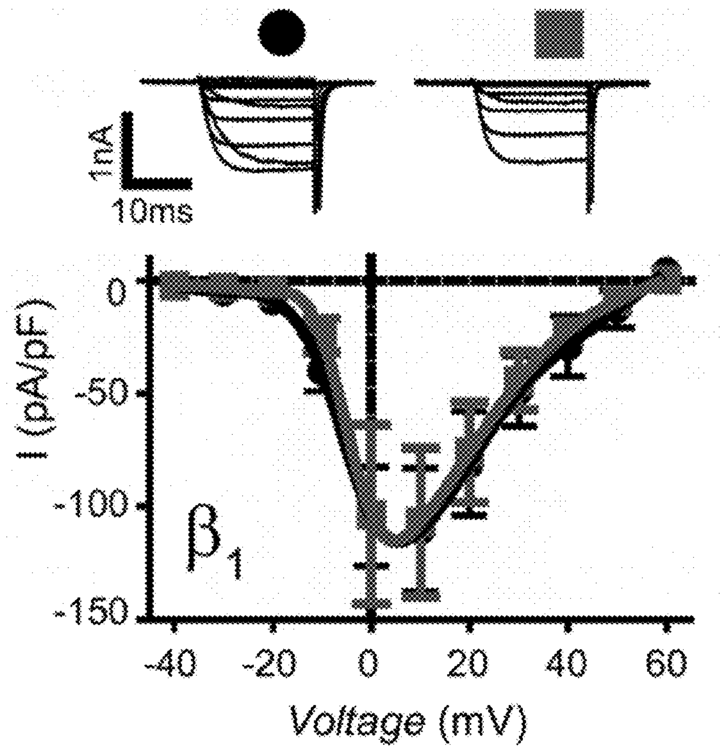
Figure 2J:
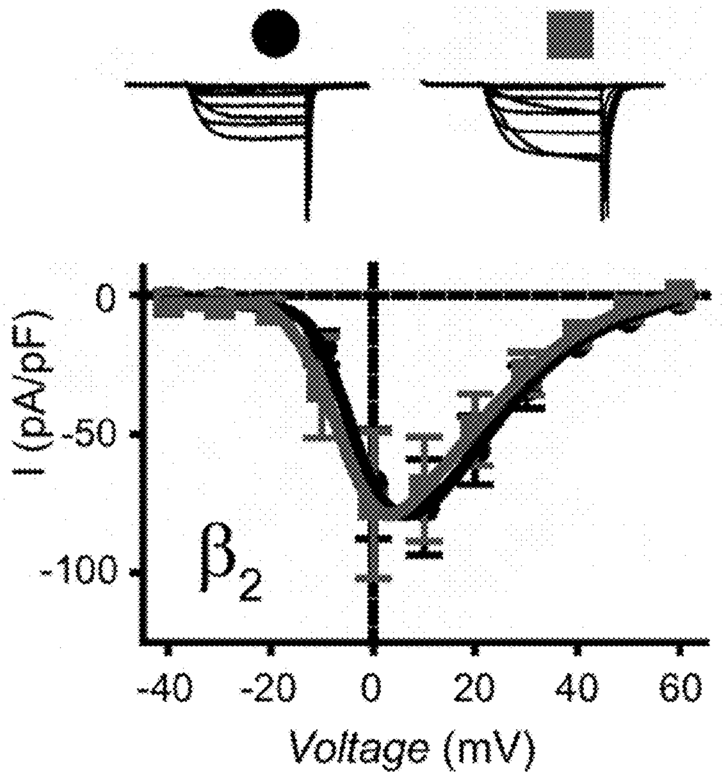
Figure 2K:
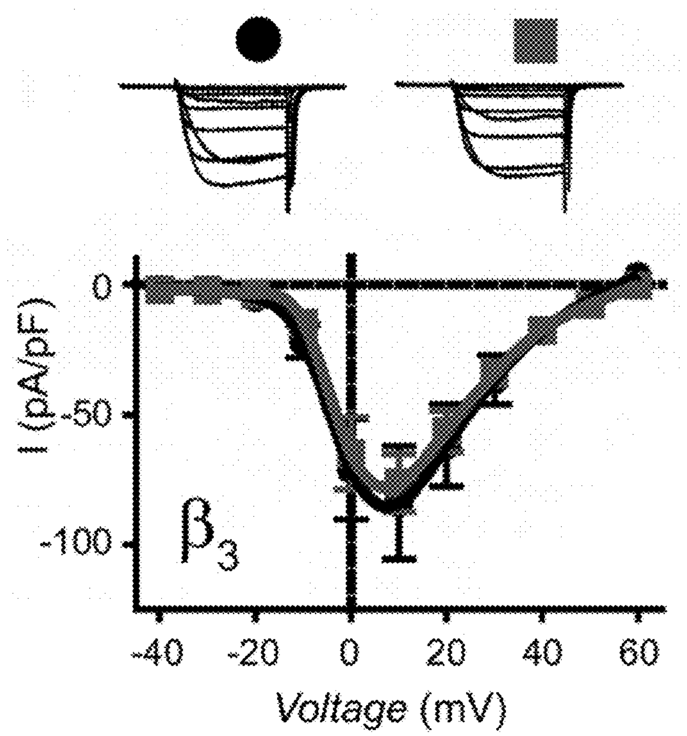
Figure 2L:
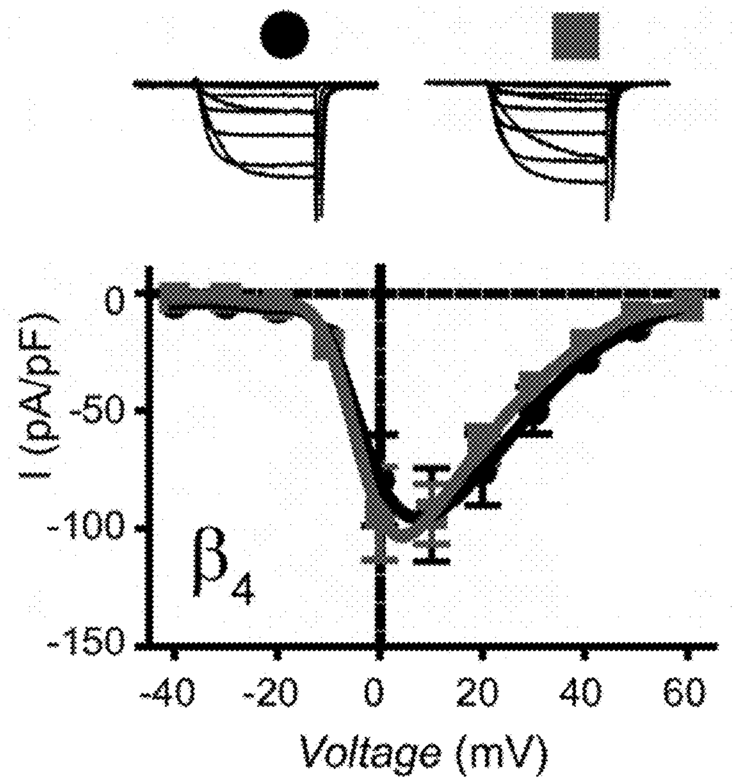

To examine a potential direct impact of nb.F3 on $Ca_V13$ itself, the flow cytometry assay was applied to cells expressing BBS-$\alpha_{1B}$+β-YFP±nb.F3-P2A-CFP (FIG. 2E). Not surprisingly, nb.F3 did not impact the surface trafficking of BBS-$\alpha_{1B}$ co-expressed with any of the four $Ca_V\beta$ isoforms (FIGS. 2F-2H and FIGS. 8A-8F). The expression levels of $\beta_1$-YFP and $\beta_4$-YFP were unaffected by nb.F3, whereas the levels of $\beta_2$ and $\beta_3$ were modestly reduced (although this effect did not reach statistical significance), suggesting a possible slightly increased vulnerability of these two isoforms to degradation when bound by the nanobody (FIG. 2H). Similar observations regarding the lack of effect of nb.F3 on channel trafficking and subunit expression levels were made in cells expressing $Ca_V1.2$ channels reconstituted from BBS-$\alpha_{1C}$+β-YFP±nb.F3-P2A-CFP (FIGS. 9A-9E).

Finally, patch-clamp electrophysiology was used to evaluate the impact of nb.F3 on whole-cell currents through recombinant $Ca_V2.2$ channels reconstituted in HEK293 cells. Cells expressing $\alpha_{1B}+\beta_{1b}+\alpha_2\delta$ displayed robust whole-cell $Ba^{2+}$ currents that were completely unaffected by nb.F3 (FIG. 2I; $I_{peak,0mV}$=−104.4±22.0 pA/pF, n=10 for CFP, and $I_{peak,0mV}$=−103.5±39.5 pA/pF, n=10 for nb.F3). A similar lack of effect of nb.F3 was observed on currents from either $Ca_V2.2$ reconstituted with the other $\beta_2$-$\beta_4$ subunits (FIGS. 2J-2L), or $Ca_V1.2$ ($\alpha_{1C}+\beta_{2a}+\alpha_2\delta$) channels (FIGS. 9A-9E).

Overall, these results indicate that nb.F3 binds $\beta_1$-$\beta_4$ subunits in cells, and is potentially assembled into $Ca_V$ channel complexes in a functionally silent manner, essentially acting as an unobtrusive passenger. However, it was also possible that the apparent functional inertness of nb.F3 on $Ca_V2.2$ and $Ca_V1.2$ channels had a more trivial explanation—that $Ca_V\beta$s assembled with pore-forming al-subunits are simply inaccessible to nb.F3. We could discriminate between these two possible scenarios by determining whether nb.F3 could be used to target bioactive molecules to regulate assembled channels, as we did next.

TABLE 1

Summary of nanobodies generated.
Bold Italics denotes nonconserved residues in Framework region

| nb | (SCAA.xxx.MG) CDR1 | (VAA.xxx.TYY) CDR2 | (CAA.xxx.YD) CDR3 | CDR3 # AA | Full sequence |
|---|---|---|---|---|---|
| b1.p1.A1 | SGFTFDDYA (SEQ ID NO: 1) | ***VSC***FSSSDGS (SEQ ID NO: 2) | IEGMRISPVVTGIPAFD***FGS*** (SEQ ID NO: 3) | 18 | QVQLQESGGGLVQPGGSLRLSCAVSGFTFDDYAIGWFRQAPGKEREAVSCFSSSDGSTYYADSVKGRFTISSDNDKNMVYLQMNSLKPEDTAVYYCAAIEGMRISPVVTGIPAFDFGSWGQGTQVTVSS (SEQ ID NO: 4) |
| b1.p1.A7 | SGRTFSSYT (SEQ ID NO: 5) | ISWSGG (SEQ ID NO: 6) | DTYYGSRMWNE (SEQ ID NO: 7) | 27 | QVQLQESGGGLVQAGGSVRLSCAASGRTFSSYTMGWFRQAPGKEREFVAAISWSGGTTYYADSVKGRFAIARDNAKNTAYLQMNSLKPEDTAVYYCAADTYYGSRMWNEYDYWGQGTQVTVSS (SEQ ID NO: 8) |
| b1.p1.D1 | SGSILTINV (SEQ ID NO: 9) | ***H***ASSGGS (SEQ ID NO: 10) | ***TL***YMRTEAQSRGTG (SEQ ID NO: 11) | 13 | QVQLQESGGGLVQPGGSLRLSCTASGSILTINVMGWYRQAPGKQRELVAHASSGGSTDYADSVKGRFTISRDNAKNTWYLQMNNLKPEDTAVYYCTLYMRTEAQSRGTGYDYWGQGTQVTVSS (SEQ ID NO: 12) |
| b1.p1.D8 | SGRTFSSYA (SEQ ID NO: 13) | IERSGG***TASH*** (SEQ ID NO: 14) | SSYWSRSVAE (SEQ ID NO: 15) | 27 | QVQLQESGGGLVQAGGSVRLSCVASGRTFSSYAMGWFRQAPGKEREFVAAIERSGGTASHADSVKGRFTISRDNAKNTVYLQMNSLKPEDTAVYSCAASSYWSRSVAEYDYWGQGTQVTVSS (SEQ ID NO: 16) |
| b1.p1.D12 | SERTFSRYA (SEQ ID NO: 17) | INWSGSS (SEQ ID NO: 18) | HYQGSYGSALA (SEQ ID NO: 19) | 28 | QVQLQESGGGLVQAGGSLRLSCAASERTFSRYAMGWFRQAPEKEREFVAAINWSGSSTYYADSVKGRFTVSRDDAKNTVYLQMNSLKPEDTAVYYCAAHYQGSYGSALAYDIWGQGTQVTVSS (SEQ ID NO: 20) |
| b1.p2.A11 | SERTFSRYA (SEQ ID NO: 21) | INWSGSS (SEQ ID NO: 22) | HYQGSYGSALA (SEQ ID NO: 23) | 28 | QVQLQESGGGLVQAGGSLRLSCAASERTFSRYAMGWFRQAPEKEREFVAAINWSGSSTYYADSVKGRFTVSRDDAKNTVYLQMNSLKPEDTAVYYCAAHYQGSYGSALAYDTWGQGTQVTVSS (SEQ ID NO: 24) |
| b1.p2.C4 | SGRTFSRNA (SEQ ID NO: 25) | ISWSGRN (SEQ ID NO: 26) | ***V***GADWRVYDESYYSTAHY***YEY*** (SEQ ID NO: 27) | 19 | QVQLQESGGGSVQAGGSLRLSCAASGRTFSRNAMGWFRQAPGKEREFVAAISWSGRNTYYADSVKGRFTISRDNAKNTLSLQMNSLKPEDSAVYICAVGADWRVYDESYYSTAHYYEYWGQGTQVTVSS (SEQ ID NO: 28) |

TABLE 1-continued

Summary of nanobodies generated.
Bold Italics denotes nonconserved residues in Framework region

| nb | (SCAA.xxx.MG) CDR1 | (VAA.xxx.TYY) CDR2 | (CAA.xxx.YD) CDR3 | CDR3 # AA | Full sequence |
|---|---|---|---|---|---|
| b1.p2.D1 | SGRTFSSYA (SEQ ID NO: 29) | IERSGG***TASH*** (SEQ ID NO: 30) | SSYWSRSVDE (SEQ ID NO: 31) | 27 | QVQLQESGGGLVQGGGSRRFSCAASGRTFSSYAMGWFRQAPGKEREFVAAIERSGGTASHADSKKGRFTISRDNTKNTVYQQMNSKKPEDTAVYYCAASSYWSRSVDEYDYWGQGTQVTVSS (SEQ ID NO: 32) |
| b1.p3.D1 | SERTFSRYA (SEQ ID NO: 33) | INWSGSS (SEQ ID NO: 34) | HYQGSYGSASA (SEQ ID NO: 35) | 28 | QVQLQESGGGLVQAGGSLRLSCAASERTFSRYAMGWFRQAPEKEREFVAAINWSGSSTYYADSVKGRFTVSRDDAKNTVNLEMNSLKPEDTAVYYCAAHYQGSYGSASAYDTWGQGTQVTVSS (SEQ ID NO: 36) |
| b1.p.D10 | SGRTFSPYA (SEQ ID NO: 37) | ITWSGGL (SEQ ID NO: 38) | ***CAL***DDDTFGVTTSTH (SEQ ID NO: 39) | 13 | QVQLQESGGGLVQAGGSLRLSCAASGRTFSPYAMGWFRQAPGKEREFVAAITWSGGLTYYADSVKGRFTISRDNSKNTVSLQMNSLKPEDTAVYYCALDDDTFGVTTSTHYDYWGQGTQVTVSS (SEQ ID NO: 40) |
| b1.p3.E8 | SGRTFSKNA (SEQ ID NO: 41) | ***VA***ISWSGRN (SEQ ID NO: 42) | ***CAV***GGDWRVYDISFYYTAHQ***YE*** (SEQ ID NO: 43) | 19 | QVQLQESGGGSVQAGGSLRLSCAASGRTFSKNAMGWFRQAPGKEREFVVAISWSGRNTYYADSVKGRFTISRDNAKNTVDLQMNSLKPEDSAVYYCAVGGDWRVYDISFYYTAHQYEYWGQGTQVTVSS (SEQ ID NO: 44) |
| b1.p3.E11 | SLGTFSRYA (SEQ ID NO: 45) | ***VSA***ISWSGGS***TLY*** (SEQ ID NO: 46) | EVFYSGSYDDTLRVQSHE (SEQ ID NO: 47) | 35 | QVQLQESGGGLVQAGGSLRLSCAASLGTFSRYAMGWFRQAPGKEREFVSAISWSGGSTLYADSVKGRFAISRDNAKNTVYLQMNSLKPEDTAVYYCAAEVFYSGSYDDTLRVQSHEYDYWGQGTQVTVSS (SEQ ID NO: 48) |
| b1.p3.F1 | SGRTFSSYT (SEQ ID NO: 49) | ISWSGGT (SEQ ID NO: 50) | DTYYGSRMWNE (SEQ ID NO: 51) | 28 | QVQLQESGGGLVQAGGSLRLSCAASGRTFSSYTMGWFRQAPGKEREFVAAISWSGGTTYYADSVKGRFAIARDNAKNTAYLQMNSLKPEDTAVYYCAADTYYGSRMWNEYDYWGQGTQVTVSS (SEQ ID NO: 52) |
| b1.neg.p1.F4 | SERTFSRYA (SEQ ID NO: 53) | INWSGSS (SEQ ID NO: 54) | ***none*** | 0 | QVQLQESGGGLVQAGGSLRLSCAASERTFSRYAMGWFRQAPEKEREFVAAINWSGSSTYYADSVKGRFTVSS (SEQ ID NO: 55) |
| b1.neg.p1.G9 | SGRTFSRNA (SEQ ID NO: 56) | INWSGSS (SEQ ID NO: 57) | ***none*** | 0 | QVQLQESGGGSVQAGGSLRLSCAASGRTFSRNAMGWFRQAPGKEREFVAAINWSGSSTYYADSVKGRFTVSS (SEQ ID NO: 58) |

TABLE 1-continued

Summary of nanobodies generated. Bold Italics denotes nonconserved residues in Framework region

| nb | (SCAA.xxx.MG) CDR1 | (VAA.xxx.TYY) CDR2 | (CAA.xxx.YD) CDR3 | CDR3 # AA | | Full sequence |
|---|---|---|---|---|---|---|
| b1.neg.p1.G8 | SERTFSRYA (SEQ ID NO: 59) | INWSGSS (SEQ ID NO: 60) | HYQGSYGSASA (SEQ ID NO: 61) | 28 | | QVQLQESGGGLVQAGGSLRLSCAASERTFSRYAMGWFRQAPEKEREFVAAINWSGSSTYYADSVKGRFTVSRDDAKNTVNLEMNSLKPEDTAVYYCAAHYQGSYGSASAYDTWGQGTQVTVSS (SEQ ID NO: 62) |
| b1.neg.p1.H11 | SGFSFDDYT***LG*** (SEQ ID NO: 63) | ***VSC***ISSSDGS (SEQ ID NO: 64) | VVGLRLPTYASNSCKIVAD***FGS*** (SEQ ID NO: 65) | 20 | | QVQLQESGGGLVQAGGSLRLSCAASGFSFDDYTLGWFRQAPGKEREGVSCISSSDGSTYYADSVKGRFTISSGNAKNTVYLQMNSLKPEDTAVYYCAAVVGLRLPTYASNSCKIVADFGSWGQGTQVTVSS (SEQ ID NO: 66) |
| b1.neg.p1.H12 | ***VA***SGRTFSSYA (SEQ ID NO: 67) | IDWSGG***TASH*** (SEQ ID NO: 68) | ***CAV***GGDWRVYDISFYYTAHQ***YE*** (SEQ ID NO: 69) | 19 | | QVQLQESGGGLVQAGGSLRLSCVASGRTFSSYAMGWFRQAPGKEREFVAAIDWSGGTASHADSVKGRFTISRDNAKNTVDLQMNSLKPEDSAVYYCAVGGDWRVYDISFYYTAHQYEYWGQGTQVTVSS (SEQ ID NO: 70) |
| b1.neg.p1.C5 | SGRTFSRNA (SEQ ID NO: 71) | ISWSGRN (SEQ ID NO: 72) | HYQGSYGSALA (SEQ ID NO: 73) | 28 | | QVQLQESGGGSVQAGGSLRLSCAASGRTFSRNAMGWFRQAPGKEREFVAAISWSGRNTYYADSVKGRFTVSRDDAKNTVYLQMNSLKPEDTAVYYCAAHYQGSYGSALAYDTWGQGTQVTVSS (SEQ ID NO: 74) |
| b1.neg.p1.G7 | SGRTFSNFA (SEQ ID NO: 75) | ITWSGS (SEQ ID NO: 76) | RGLWRYYTESYFYTEDR (SEQ ID NO: 77) | 33 | | QVQLQESGGGLVQAGGSLRLSCAASGRTFSNFAMGWFRQAPGKEREFVAAITWSRGSTYYTDSVKGRFTISRDNAKNTGYLQMNSLKPEDSAVYYCAAGLWRYYTESYFYTEDRYDYWGQGTQVTVSS (SEQ ID NO: 78) |
| b3.p3.A8 | ***AV***SGFTLDNYAIG (SEQ ID NO: 79) | ***VSC***ISSSDGS (SEQ ID NO: 80) | THEQVWKTLFSSCTVERDD (SEQ ID NO: 81) | 36 | | QVQLQESGGGLVQPGGSLRLSCAVSGFTLDNYAIGWFRQAPGKEREGVSCISSSDGSTYYADSVKGRFTISSDNDKNMVYLQMNSLKPEDTAVYYCATHEQVWKTLFSSCTVERDDYDYWGQGTQVTVSS (SEQ ID NO: 82) |
| b3.p3.F3 | ***VA***SGRTFSSYA (SEQ ID NO: 83) | IDWSGG***TASH*** (SEQ ID NO: 84) | SSYWSRSVDE (SEQ ID NO: 85) | 27 | | QVQLQESGGGLVQAGGSLRLSCVASGRTFSSYAMGWFRQAPGKEREFVAAIDWSGGTASHADSVKGRFTISRDNAKNTVYLQMNSLKPEDTAVYYCAASSYWSRSVDEYDYWGQGTQVTVSS (SEQ ID NO: 86) |
| b3.p3.B11 | SGFTLDNYA***IG*** (SEQ ID NO: 87) | ***VSC***ISSSDGS (SEQ ID NO: 88) | THEQVWKTLFSSCTVERDD (SEQ ID NO: 89) | 36 | differs from b3.p3.A8 in FW | QVQLQESGGGLVQPGGSLRLSCAASGFTLDNYAIGWFRQAPGKEREGVSCISSSDGSTYYADSVKGRFTISRDNAKNTAYLQLNSLKPEDTAVYYCATHEQVWKTLFSSCTVERDDYDYWGQGTQVTVSS (SEQ ID NO: 90) |
| b3.p3.G1 | SGFTLDNYAIG (SEQ ID NO: 91) | ***VSC***ISSSDGS (SEQ ID NO: 92) | THEQVWKTLFSSCTVERDD (SEQ ID NO: 93) | 36 | differs from b3.p3.B11 in FW1 | QVQLQESGGGLVQAGGSLRLSCAASGFTLDNYAIGWFRQAPGKEREGVSCISSSDGSTYYADSVKGRFTISRDNAKNTAYLQLNSLKPEDTAVYYCATHEQVWKTLFSSCTVERDDYDYWGQGTQVTVSS (SEQ ID NO: 94) |
| b3.p3.G4 | SGRTFSSYA (SEQ ID NO: 95) | IDWSGG***TSVH*** (SEQ ID NO: 96) | TSYWSTAEYE (SEQ ID NO: 97) | 27 | | QVQLQESGGGLVQAGGSLRLSCAASGRTFSSYAMGWFRQTPGKEREFVAAIDWSGGTSVHADSVKGRFTIARDNAKNTVYLQMSSLKPEDTATYYCAATSYWSTAEYEYDYWGQGTQVTVSS (SEQ ID NO: 98) |

Example 3

Potent Functional Effects of an F3-Nedd4L Chimeric Protein on CaV1/CaV2 Channels It was hypothesized that fusing the catalytic domain of an E3 ubiquitin ligase to nb.F3 would generate a genetically-encoded molecule that inhibits Cav1/Cav2 channels by reducing their surface density (Kanner et al., 2017). Accordingly, a chimeric construct (nb.F3-Nedd4L) was generated by fusing the catalytic HECT domain of Nedd4L to the C-terminus of nb.F3. We also generated a catalytically dead mutant of the chimeric construct (nb.F3-Nedd4L[C942S]) to distinguish between ubiquitination-dependent and independent effects. Both constructs were generated in a P2A-CFP expression vector, enabling use of CFP fluorescence to confirm protein expression.

Figure 3A:
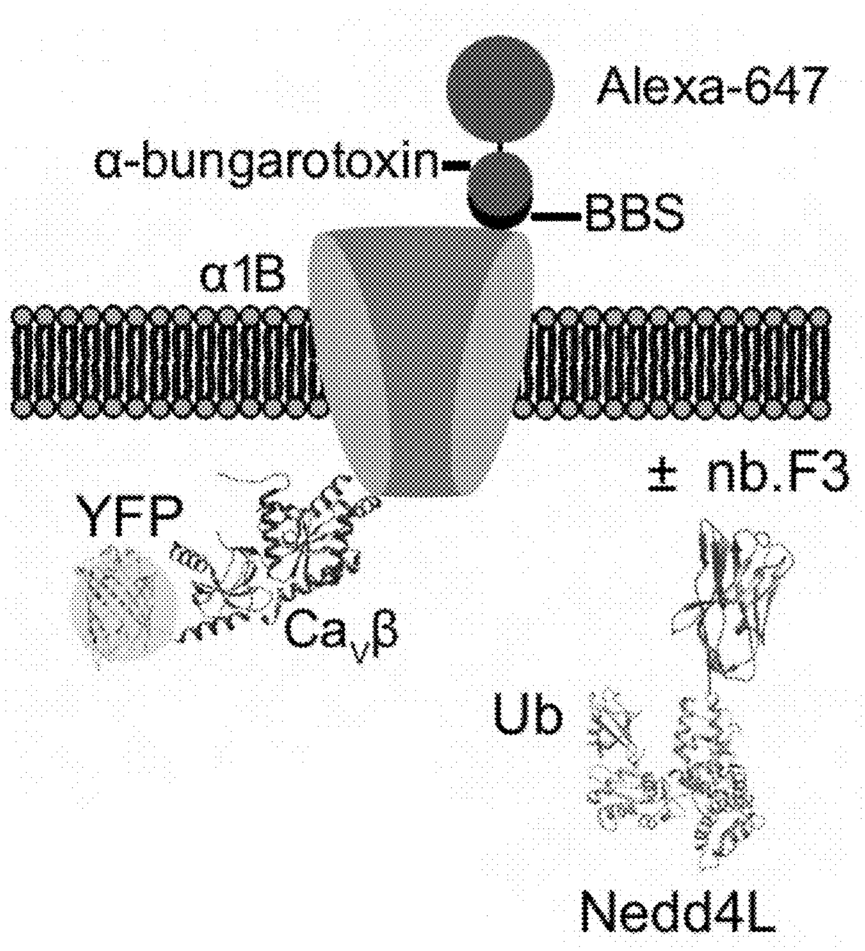
FIGS. 3A-3J show the functional impact of a chimeric nb.F3-Nedd4L protein ($Ca_V$-aβlator) on reconstituted $Ca_V2.2$ channels.
Figure 3B:
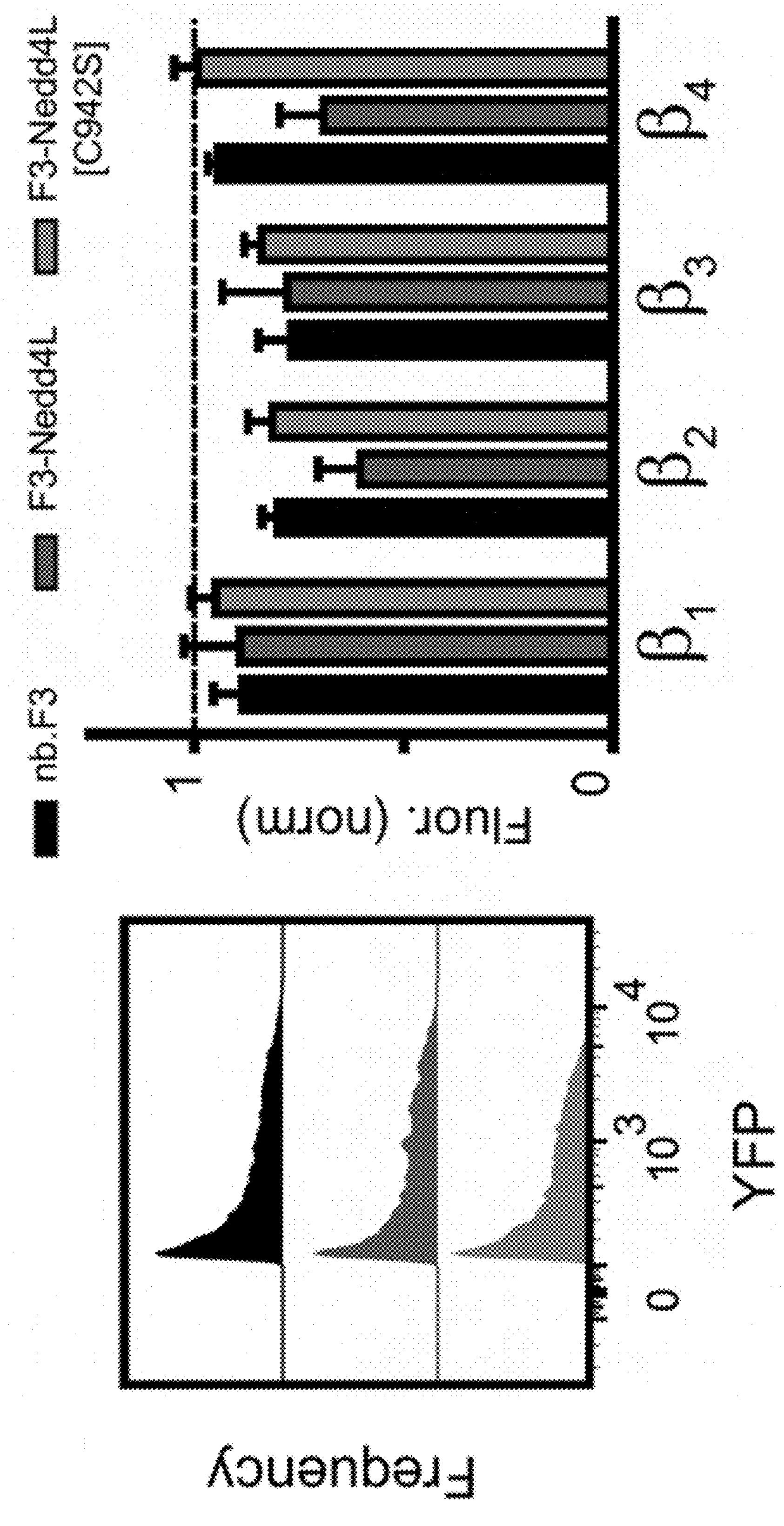
Figure 3C:
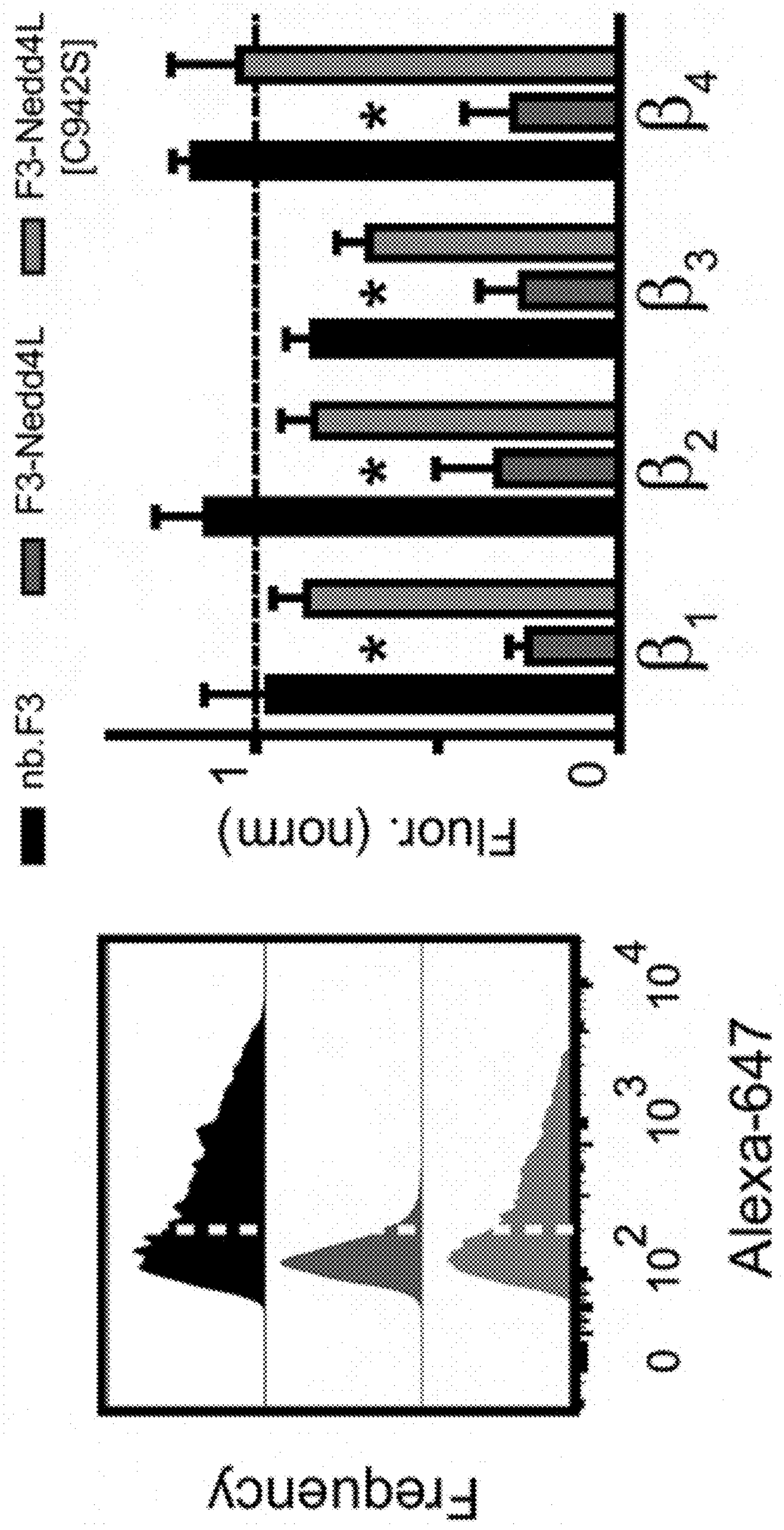
Figure 3D:
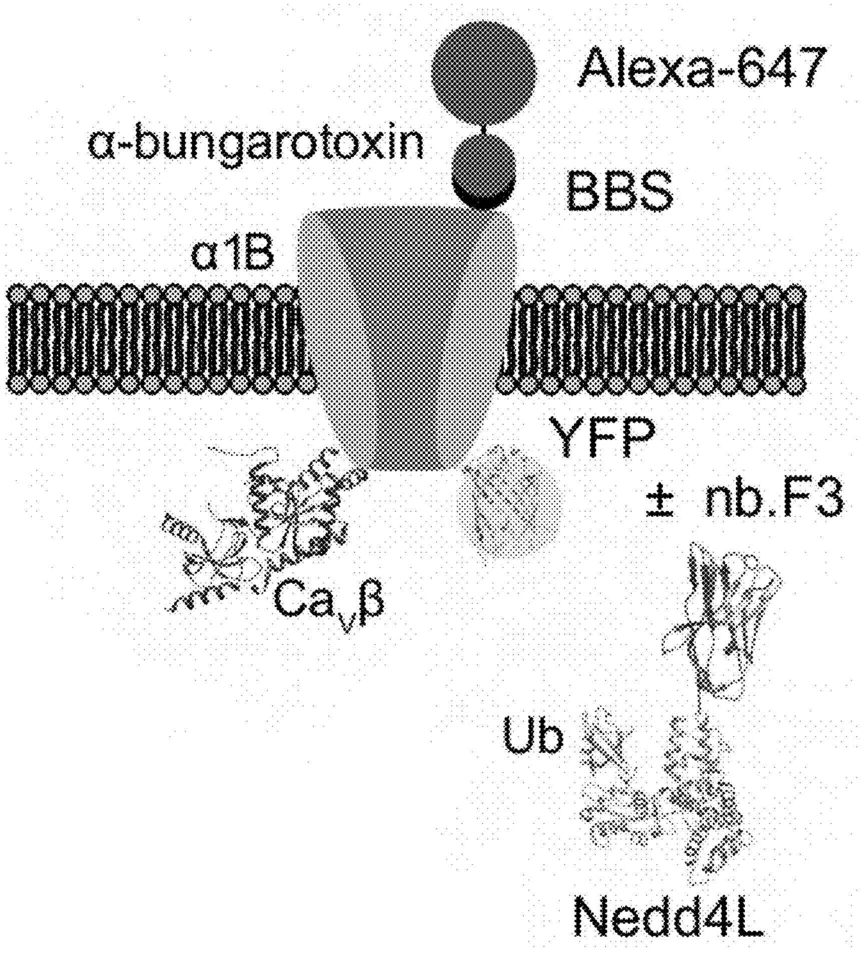
Figure 3E:
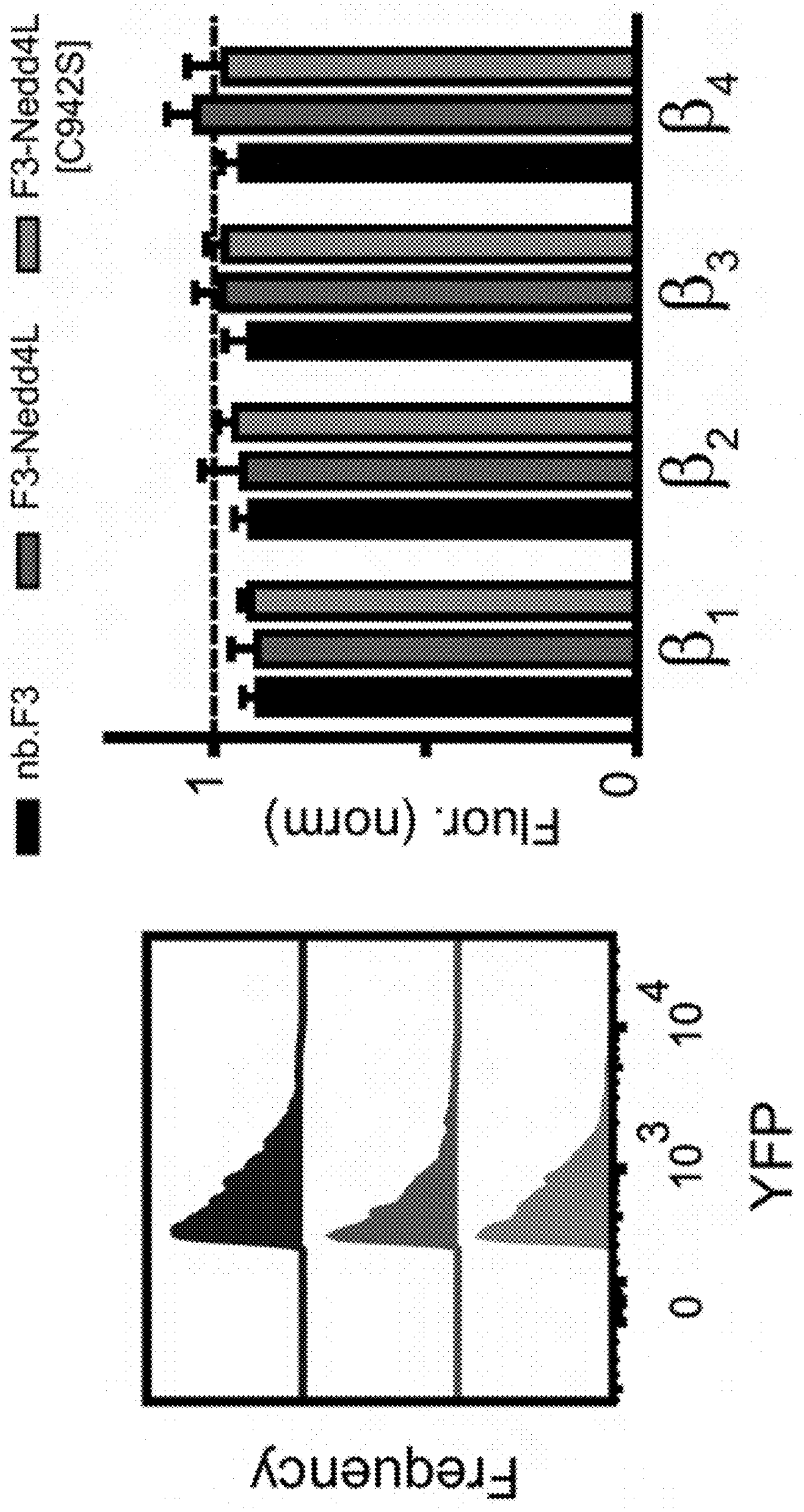

In experiments mimicking those described for nb.F3, the impact of nb.F3-Nedd4L and nb.F3-Nedd4L[C942S] on reconstituted $Ca_V2.2$ channel trafficking, subunit expression levels, and whole-cell currents (FIGS. 3A-3J) was examined. Given the classical role of E3 ubiquitin ligases in mediating degradation of target proteins, it was first assessed if nb.F3-Nedd4L affected total $Ca_V\beta$ expression (FIGS. 3A and 3B). In cells expressing BBS-$\alpha_{1B}$+$\beta_{1b}$-YFP+$\alpha_2\delta$, neither F3-Nedd4L nor F3-Nedd4L[C942S] had any significant impact on $\beta_{1b}$ total expression as reported by the unchanged YFP fluorescence compared to negative control cells (FIGS. 3A and 3B). Similar results were obtained when BBS-$\alpha_{1B}$ was reconstituted with YFP-tagged $\beta_2$, $\beta_3$, or $\beta_4$ subunits, though there was a trend towards lower fluorescence with $\beta_{2a}$ and $\beta_4$ (FIG. 3B). By contrast, nb.F3-Nedd4L significantly suppressed surface density of BBS-$\alpha_{1B}$ irrespective of the identity of the co-expressed YFP-tagged $Ca_V\beta$ (FIG. 3C, red bars; FIGS. 10A-10H). The decreased BBS-$\alpha_{1B}$ surface density was not observed with nb.F3-Nedd4L [C942S] (FIG. 3C, green bars), indicating it requires the catalytic activity of the attached Nedd4L HECT domain.

Similarly, in cells expressing BBS-$\alpha_{1C}$+$\beta_X$-YFP, nb.F3-Nedd4L strongly reduced $Ca_V$1.2 surface density in a ubiquitin-dependent manner (FIGS. 11A-11D).

Figure 3F:
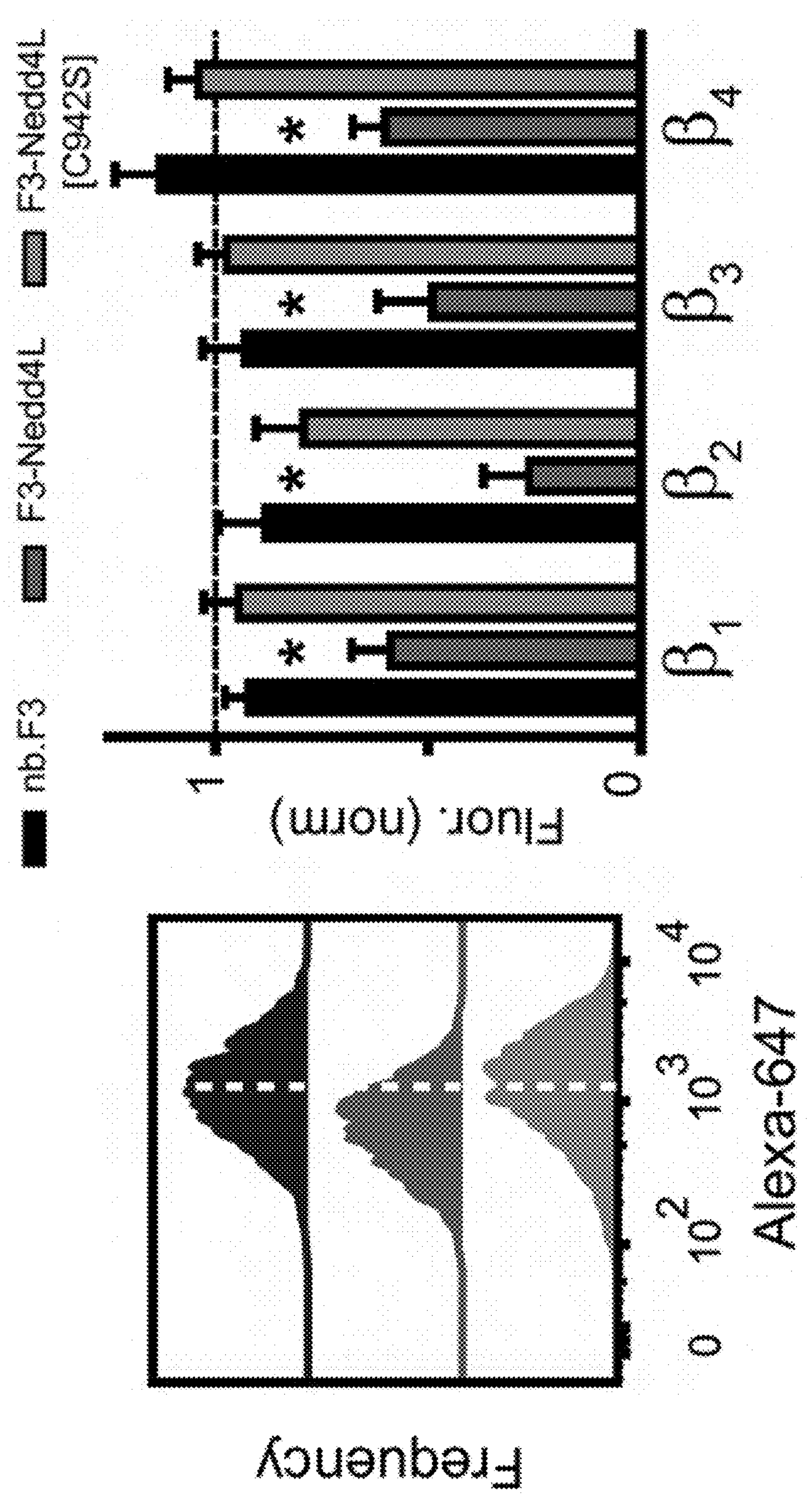
Figure 3G:
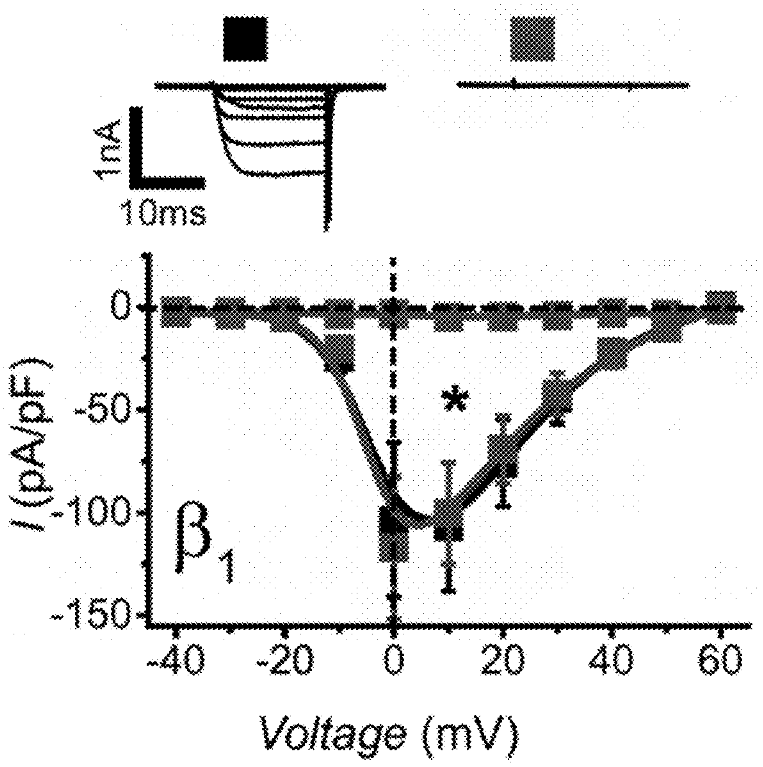
Figure 3H:
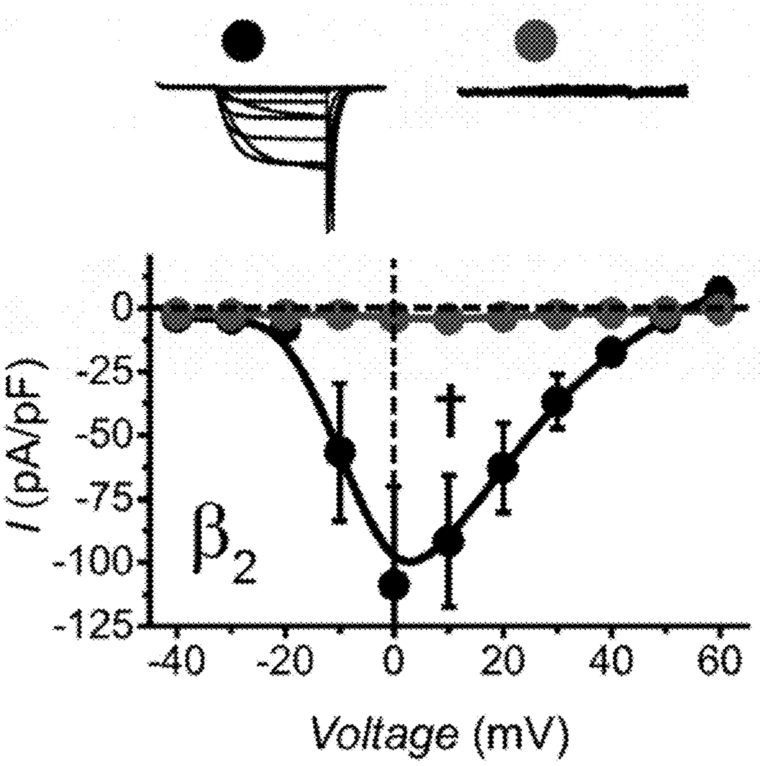
Figure 3I:
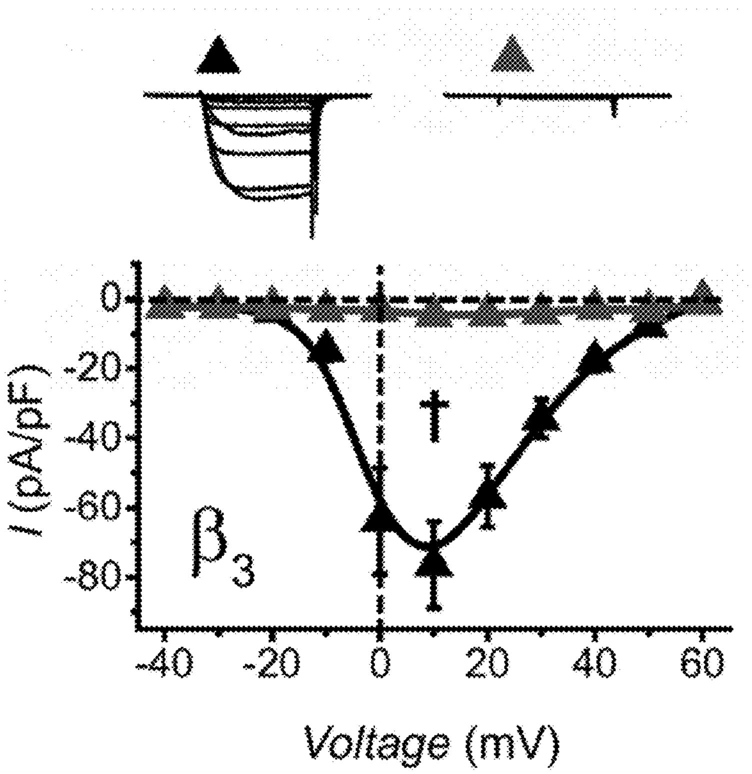
Figure 3J:
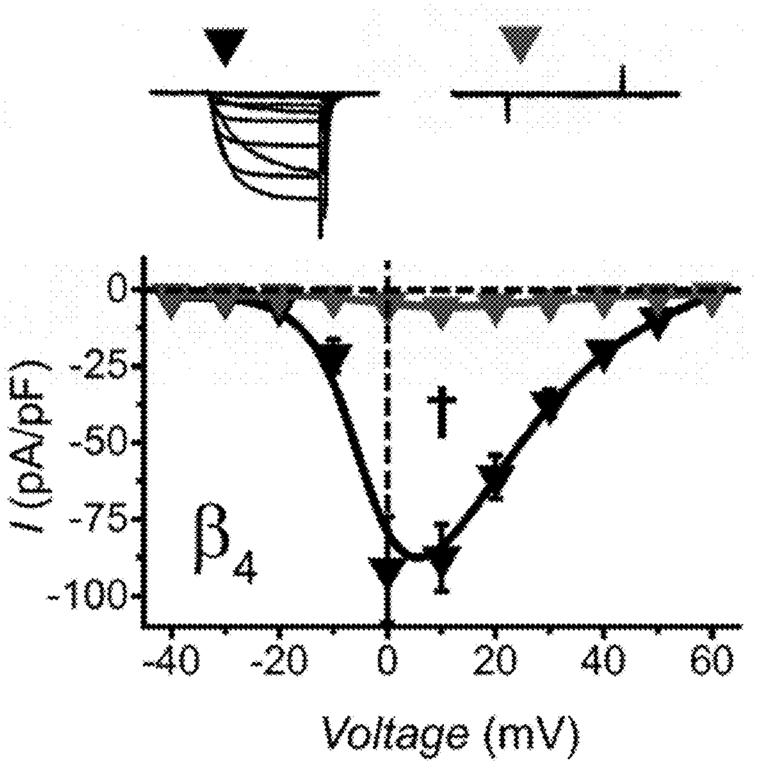
Figure 4A:
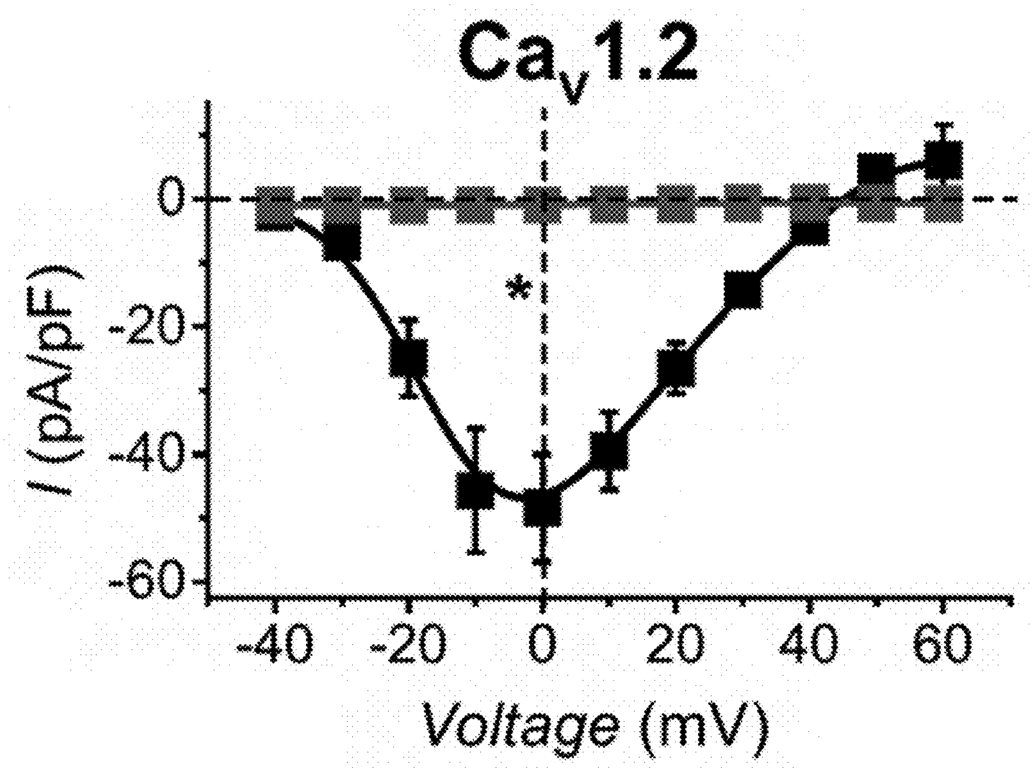
FIGS. 4A-4D show that $Ca_V$-aβlator inhibits distinct reconstituted HVACCs.
Figure 4B:
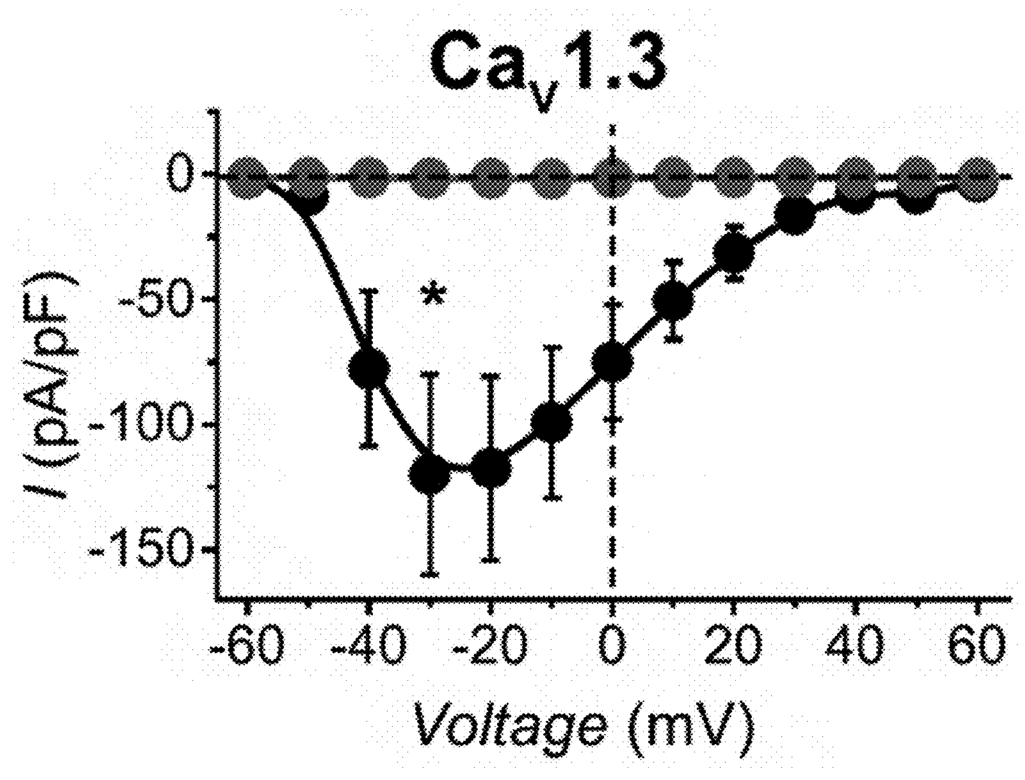
Figure 4C:
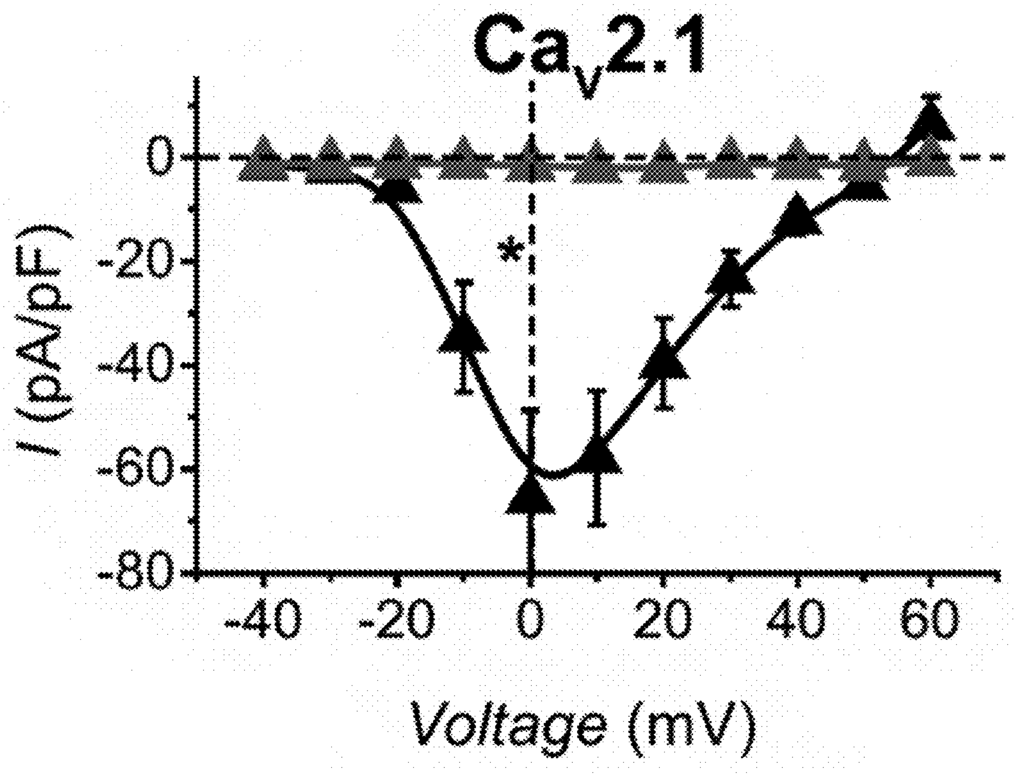
Figure 4D:
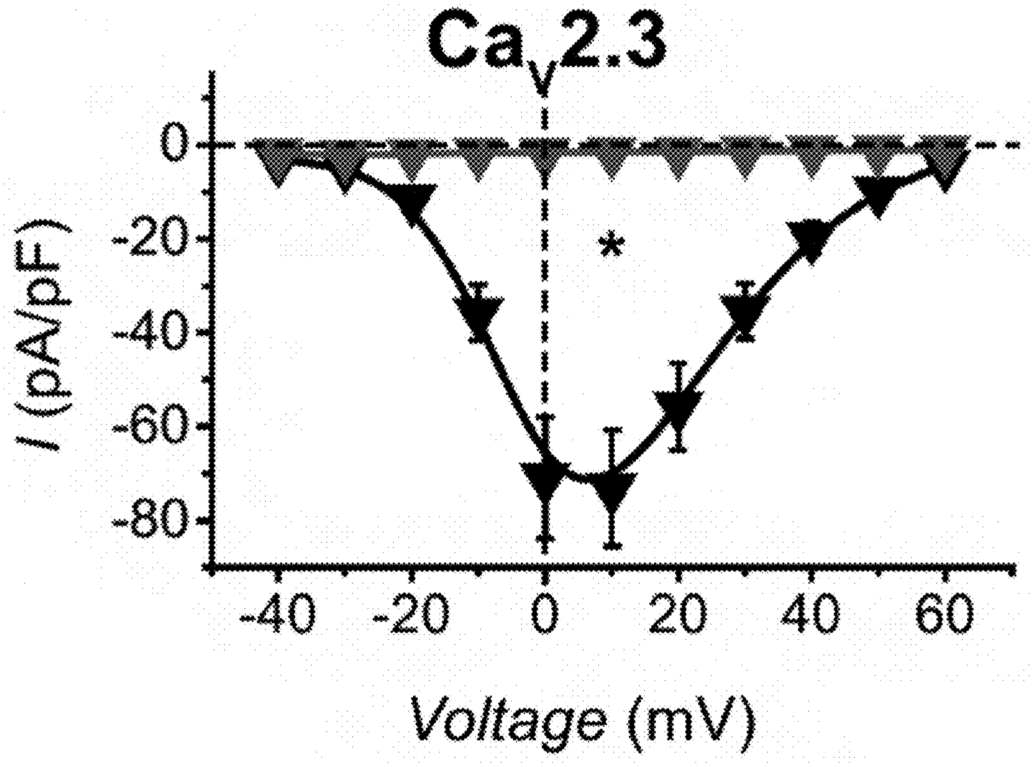

Given the striking effect of nb.F3-Nedd4L on surface population of channels without affecting total levels $Ca_V\beta$, it was next assessed whether there was any impact of nb.F3-Nedd4L on total $\alpha_{1B}$ subunit expression. Similar to our observations for $Ca_V\beta$, nb.F3-NeddL had no significant impact on the expression of BBS-$\alpha_{1B}$-YFP (FIG. 3E, red bars) relative to either negative controls (black bars) or cells expressing nb.F3-Nedd4L[C942S] (green bars). Not surprisingly, nb.F3-Nedd4L markedly impaired surface trafficking of BBS-$\alpha_{1B}$-YFP co-expressed with any $Ca_V\beta$ (FIG. 3F).

Finally, the functional impact of nb.F3-Nedd4L on reconstituted $Ca_V$2.2 whole-cell currents was examined. Remarkably, nb.F3-Nedd4L essentially eliminated $Ca_V$2.2 currents reconstituted from $\alpha_{1B}$+$\alpha_2\delta$ co-expressed with any of the four $Ca_V\beta$s (FIGS. 3G-3J). Further, nb.F3-Nedd4L was equally effective in ablating whole-cell currents in reconstituted $Ca_V$1.2, $Ca_V$1.3, $Ca_V$2.1, and $Ca_V$2.3 channels (FIGS. 4A-4D).

Given its exceptional efficacy in ablating whole-cell HVACC currents via a functionalized $Ca_V\beta$-targeted nanobody, we named nb.F3-Nedd4L as $Ca_V$-aβlator, and describe the process of HVACC current elimination by this molecule as $Ca_V$-aβlation.

Example 4

CaV-aβlation of Endogenous CaV1.2 Channels in Cardiomyocytes

Figure 5A:
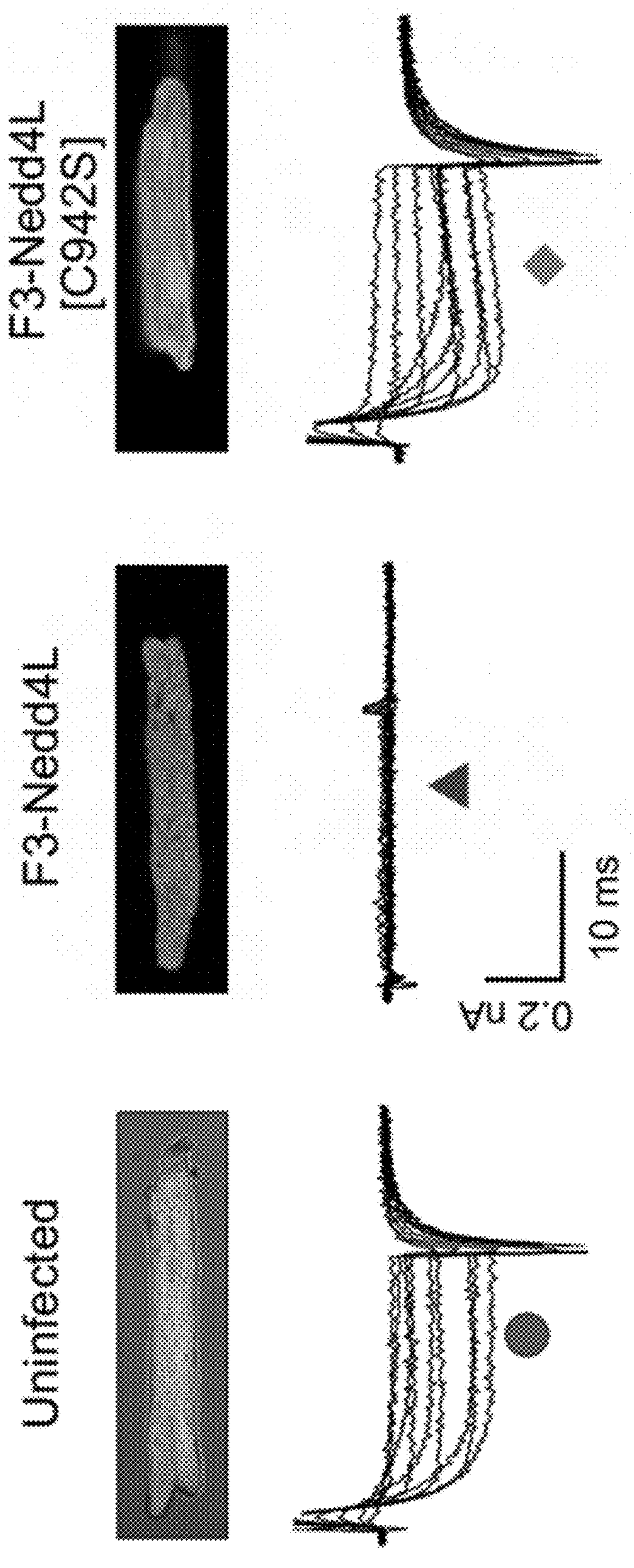
FIGS. 5A-5H show the $Ca_V$-aβlation of endogenous $Ca_V1.2$ in cardiomyocytes.
Figure 5B:
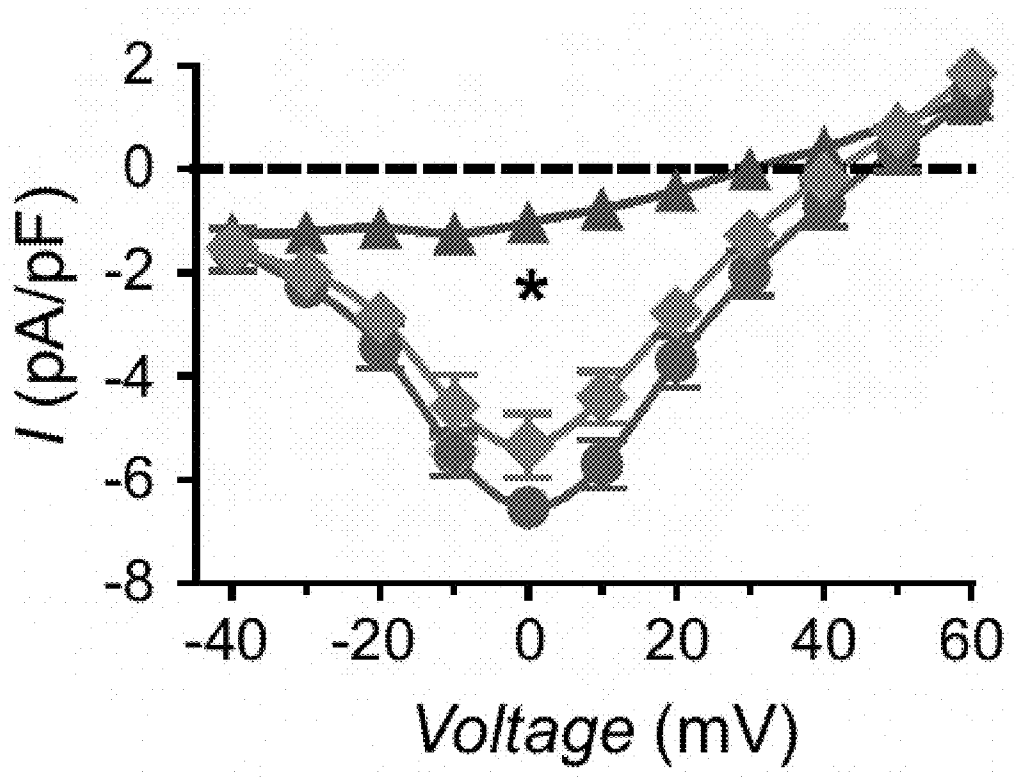

It was next determined whether $Ca_V$-aβlator could effectively inhibit HVACC currents in native cells where the nano-environment around $Ca_V$1/$Ca_V$2 channels is typically more complex than in heterologous cells. Cultured adult guinea pig ventricular cardiomyocytes (CAGPVCs) provided an initial exceptional challenge because they have an intricate cyto-architecture and express $Ca_V$1.2 channels that are predominantly targeted to specialized dyadic junctions. Moreover, as it has now been shown that in adult cardiomyocytes binding of $\alpha_{1C}$ to $Ca_V\beta$ is not obligatory for substantive $Ca_V$1.2 channel trafficking to the surface sarcolemma (Yang et al., 2019; Meissner et al., 2011), the fraction of $Ca_V\beta$-bound $Ca_V$1.2 channels contributing to the whole-cell L-type current ($I_{Ca,L}$) in ventricular myocytes is ambiguous. Adenovirus was used to express $Ca_V$-aβlator or nb.F3-Nedd4L[C942S] in CAGPVCs which retain the rod-shaped phenotype and overall cyto-architecture of freshly isolated heart cells (FIG. 5A). Control (non-infected) cardiomyocytes expressed $I_{Ca,L}$ that peaked at a 0 mV test pulse (FIGS. 5A and 5B; $I_{peak,0mV}$=−6.5±0.2 pA/pF, n=8). By contrast, in contemporaneous experiments, cardiomyocytes expressing $Ca_V$-aβlator via adenovirus-mediated infection displayed virtually no $Ca_V$1.2 currents, demonstrating an exceptional $Ca_V$-aβlation efficiency in this system (FIGS. 5A and 5B; $I_{peak,0mV}$=−1.0±0.3 pA/pF, n=9). Cardiomyocytes expressing nb.F3-Nedd4L[C942S] displayed $I_{Ca,L}$ similar to control ($I_{peak,0mV}$=−5.1±0.6 pA/pF, n=10), indicating that ubiquitination is necessary for $Ca_V$-aβlation in this system.

Figure 5C:
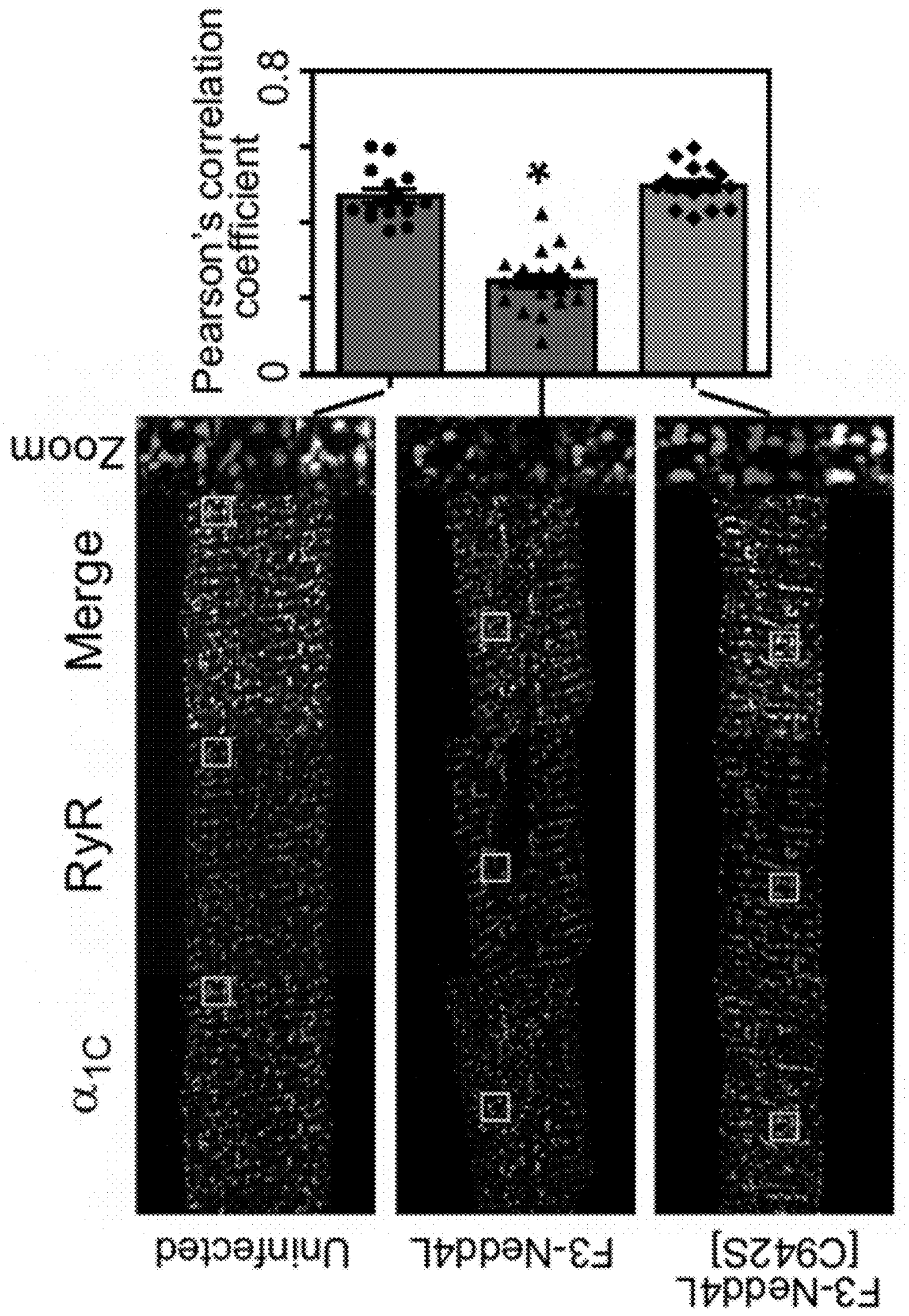
Figure 5D:
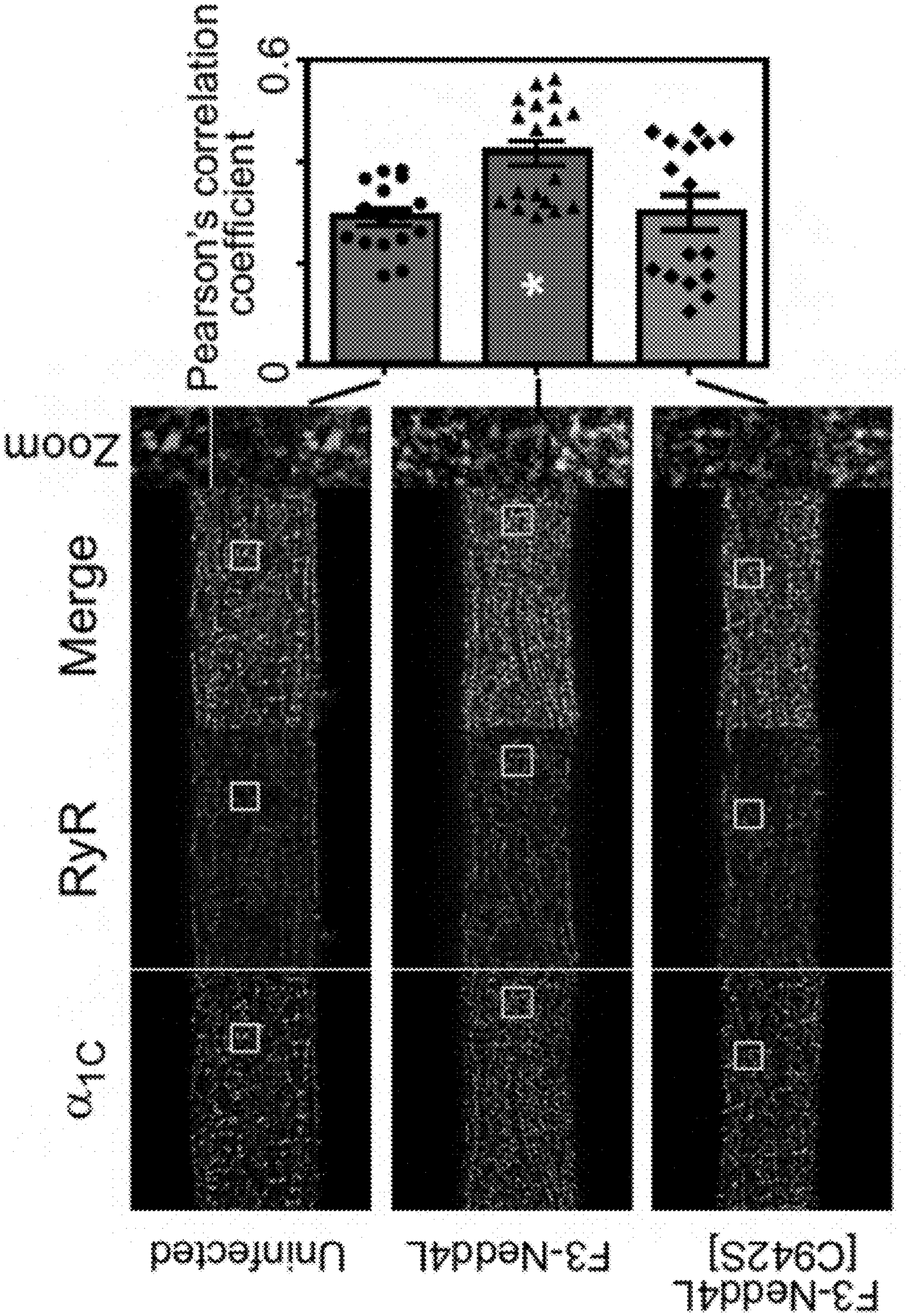

What is the mechanism of $Ca_V$-aβlation in cardiomyocytes? Immunofluorescence was used to probe how $Ca_V$-aβlator affected expression levels and sub-cellular localization of $Ca_V$1.2 $\alpha_{1C}$ and $\beta_2$ subunits, respectively, in cardiomyocytes. $Ca_V\alpha_{1C}$ in uninfected cardiomyocytes presented with a characteristic striated punctate distribution pattern that co-localized with that of ryanodine (RyR2) receptors (FIG. 5C), reflecting their well-known predominant localization at dyadic junctions (Scriven et al., 2000; Bers, 2002). A similar distribution pattern for $\alpha_{1C}$ was observed in cardiomyocytes expressing nb.F3-Nedd4L [C942S], consistent with the lack of effect of this protein on $I_{Ca,L}$. In cardiomyocytes expressing $Ca_V$-aβlator, the signal intensity for punctate $\alpha_{1C}$ staining was unchanged from control cells (FIGS. 12A-12D), suggesting no impact of the presumed increase in ubiquitination on the stability of the protein. However, there was a redistribution of $\alpha_{1C}$ from dyadic junctions, as reported by a dramatic loss of co-localization between $\alpha_{1C}$ and RyR2 (FIG. 5C). Rather, the punctate $\alpha_{1C}$ signals in $Ca_V$-aβlator-expressing cardiomyocytes coincided with Rab7, but not Rab5 or LAMP1, immunofluorescence signals (FIG. 5D; FIGS. 12A-12D). Thus, the mechanism of $Ca_V$-aβlator inhibition of $I_{Ca,L}$ is redistribution of $\alpha_{1C}$ from dyadic junctions to intracellular compartments, specifically Rab7-positive late endosomes (FIG. 5H) (Rink et al., 2005).

Figure 5E:
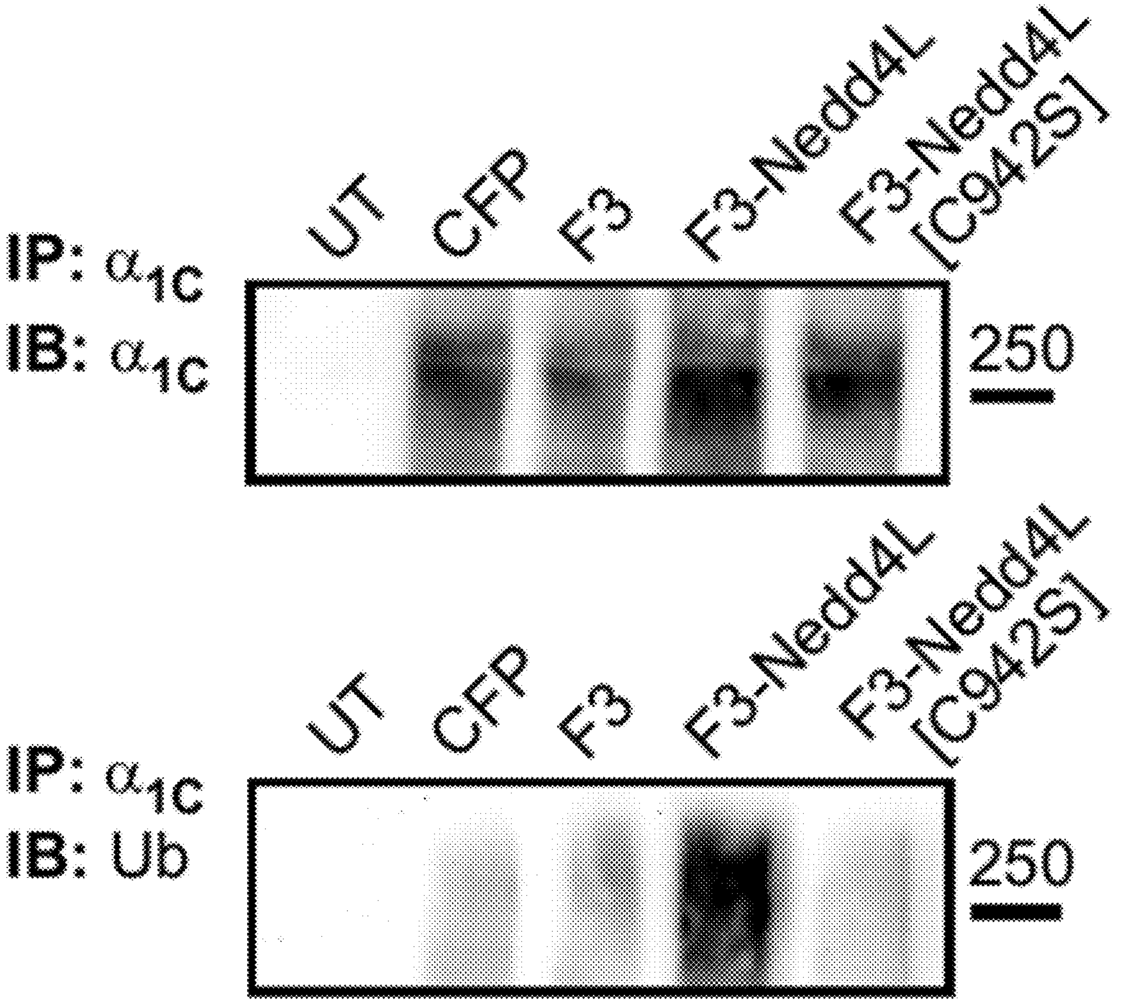
Figure 5F:
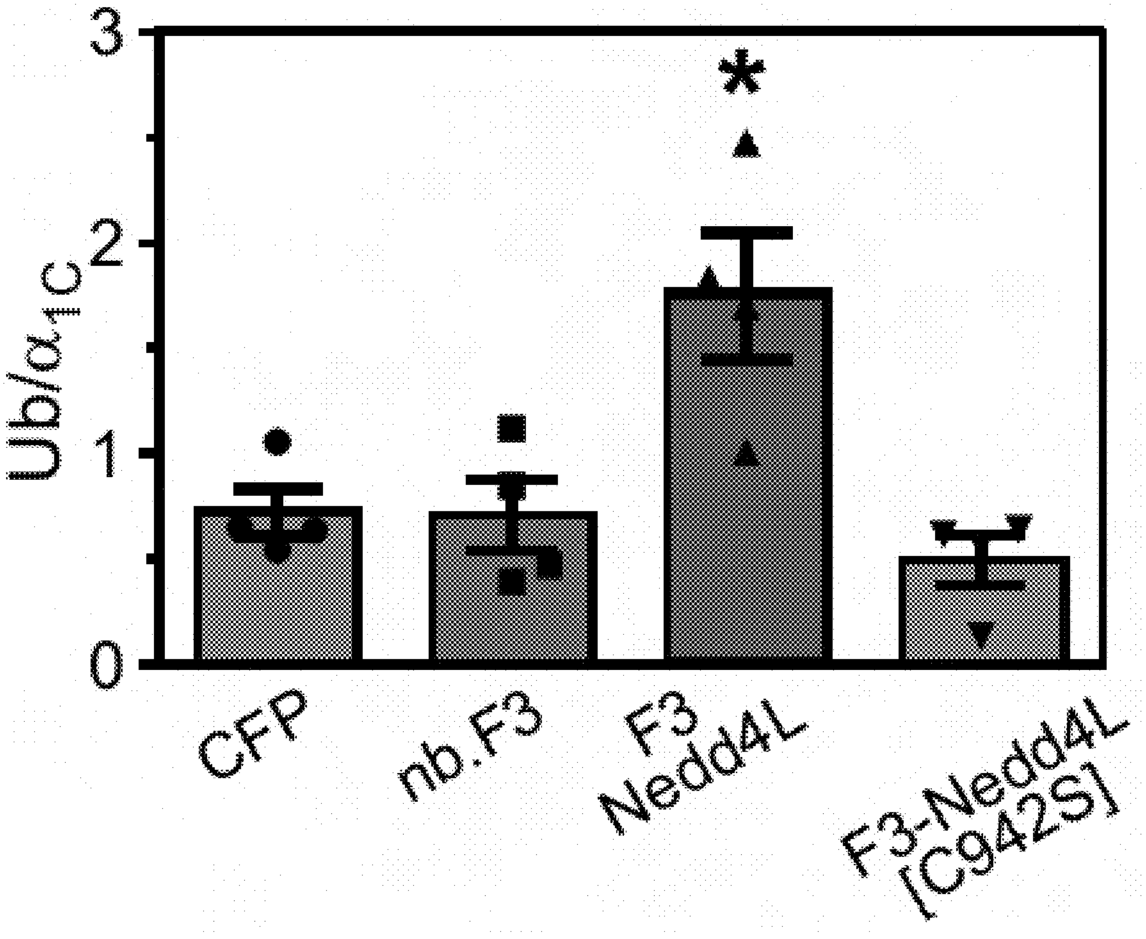
Figure 5G:
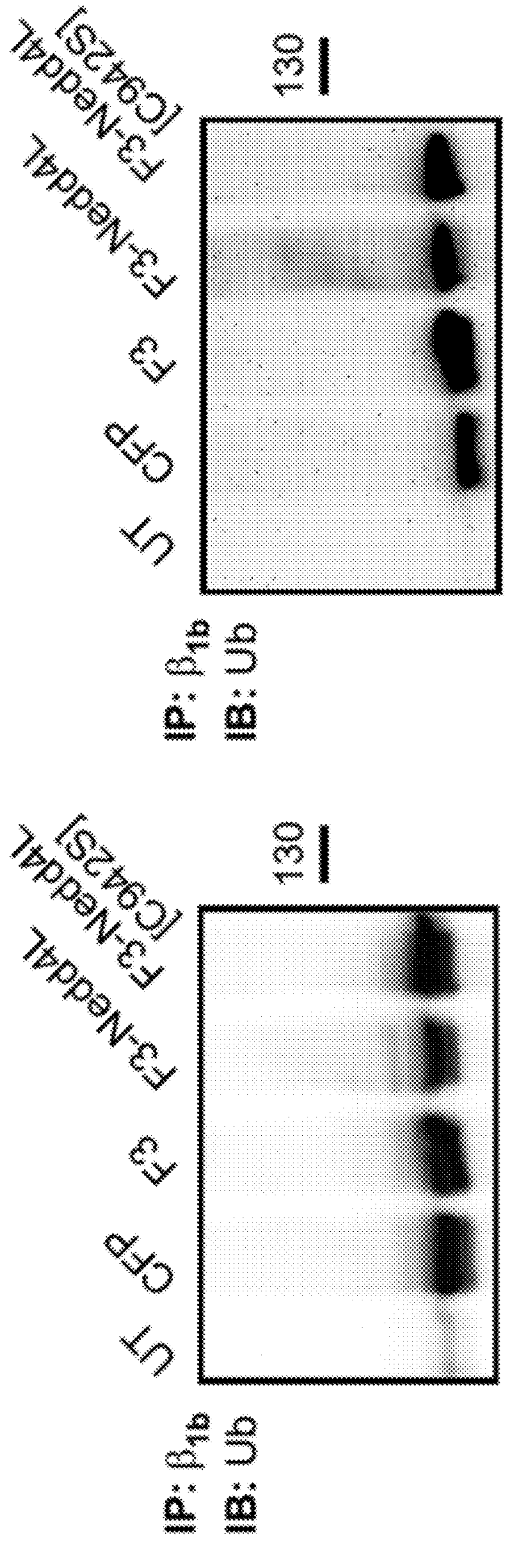
Figure 5H:
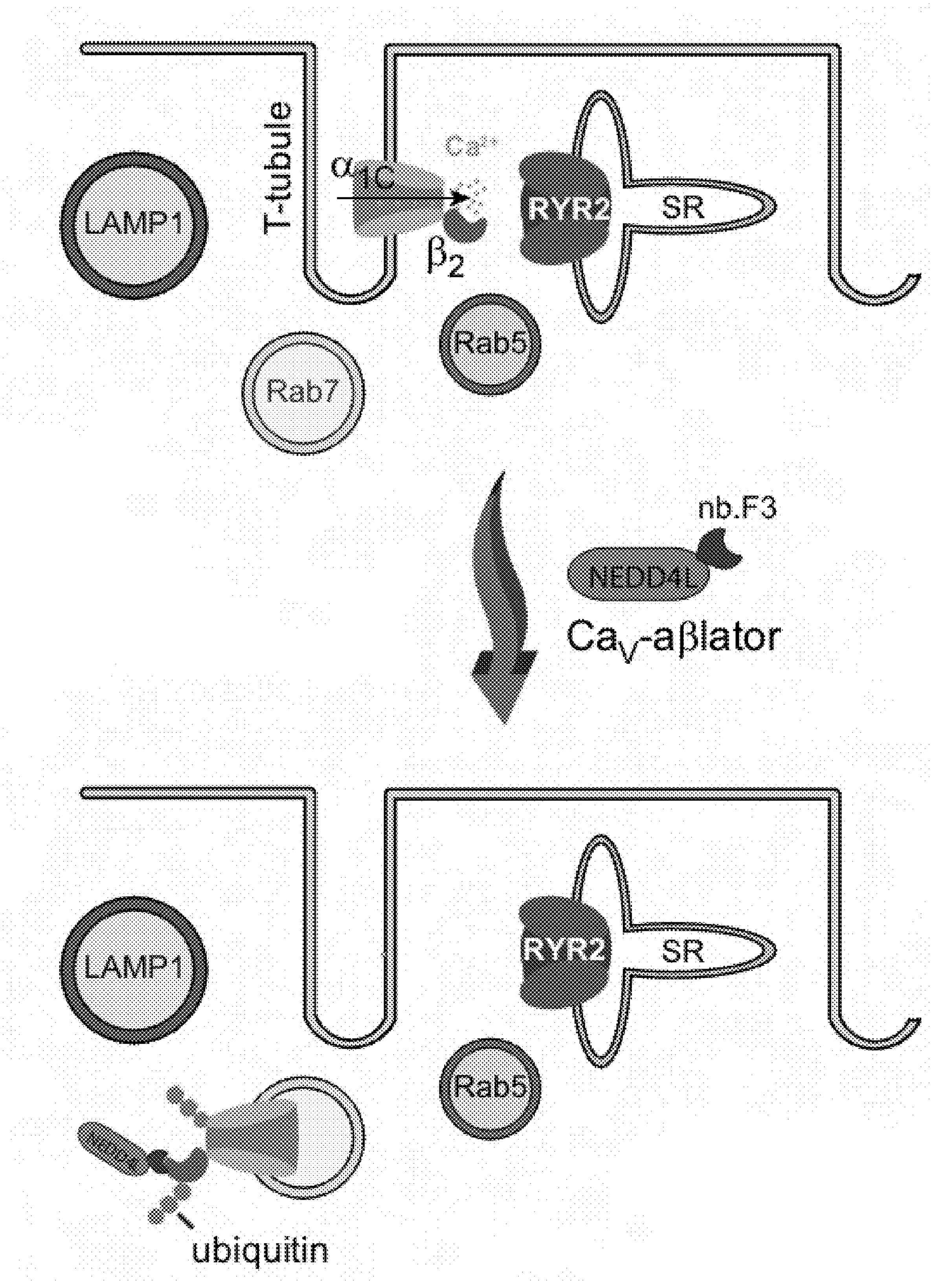

Cardiomyocytes expressing $Ca_V$-aβlator also showed no difference in total $Ca_V\beta_2$ levels as compared to either uninfected or nb.F3-Nedd4L[C942S]-expressing cells (FIGS. 12A-12D). Hence, $Ca_V$-aβlator-mediated redistribution of $Ca_V$1.2 in cardiomyocytes cannot be explained as simply due to an absence of $Ca_V\beta$. An intriguing possibility was that though $Ca_V$-aβlator is specifically targeted to $Ca_V\beta$ in channel complexes, it is also able to directly catalyze ubiquitination of $\alpha_1$ subunits within the macro-molecular complex. Indeed, in pulldown experiments of recombinant $Ca_V$1.2 channels, $Ca_V$-aβlator substantially increased ubiquitination of both $\alpha_{1C}$ (FIGS. 5E and 5F) and $Ca_V\beta_{1b}$ subunits (FIG. 5G). Nevertheless, the overall levels of $\alpha_{1C}$ expression was unchanged with $Ca_V$-aβlator despite the increased ubiquitination (FIG. 5E). Taken together, our results suggest that direct ubiquitination of $\alpha_{1C}$ by $Ca_V$-aβlator may underlie the redistribution of $Ca_V$1.2 channels from dyads to Rab7-positive late endosomes (FIG. 5H).

Example 5

CaV-aβlation in Dorsal Root Ganglion (DRG) Neurons and Pancreatic β Cells

Figure 6A:
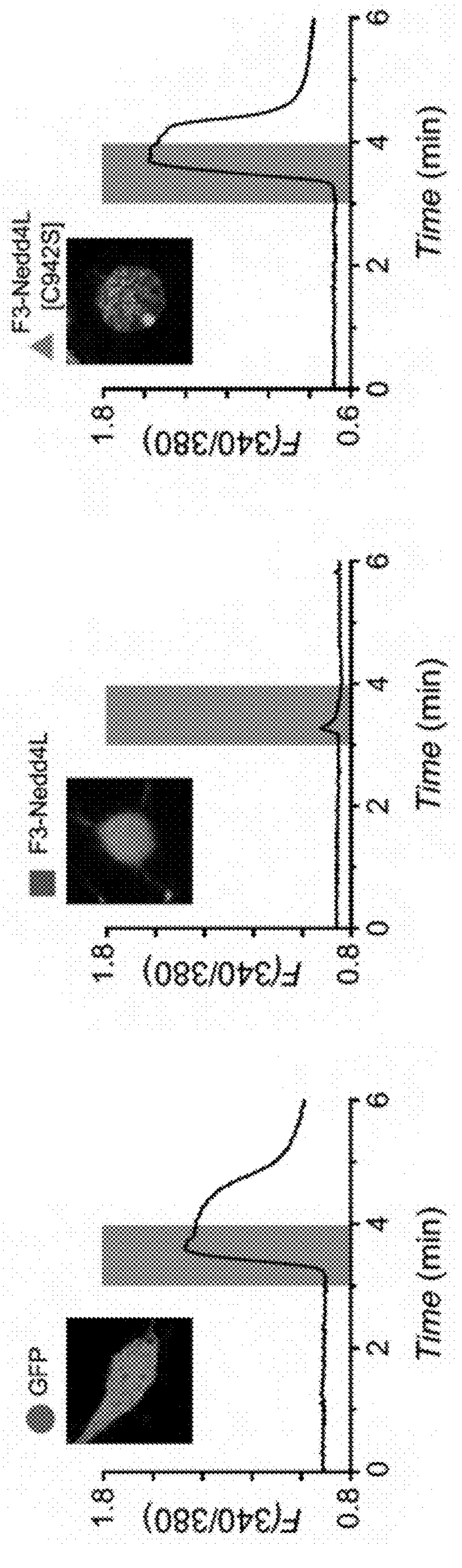
FIGS. 6A-6G show the $Ca_V$-aβlation of HVACCs in DRG neurons and pancreatic β-cells.
Figure 6B:
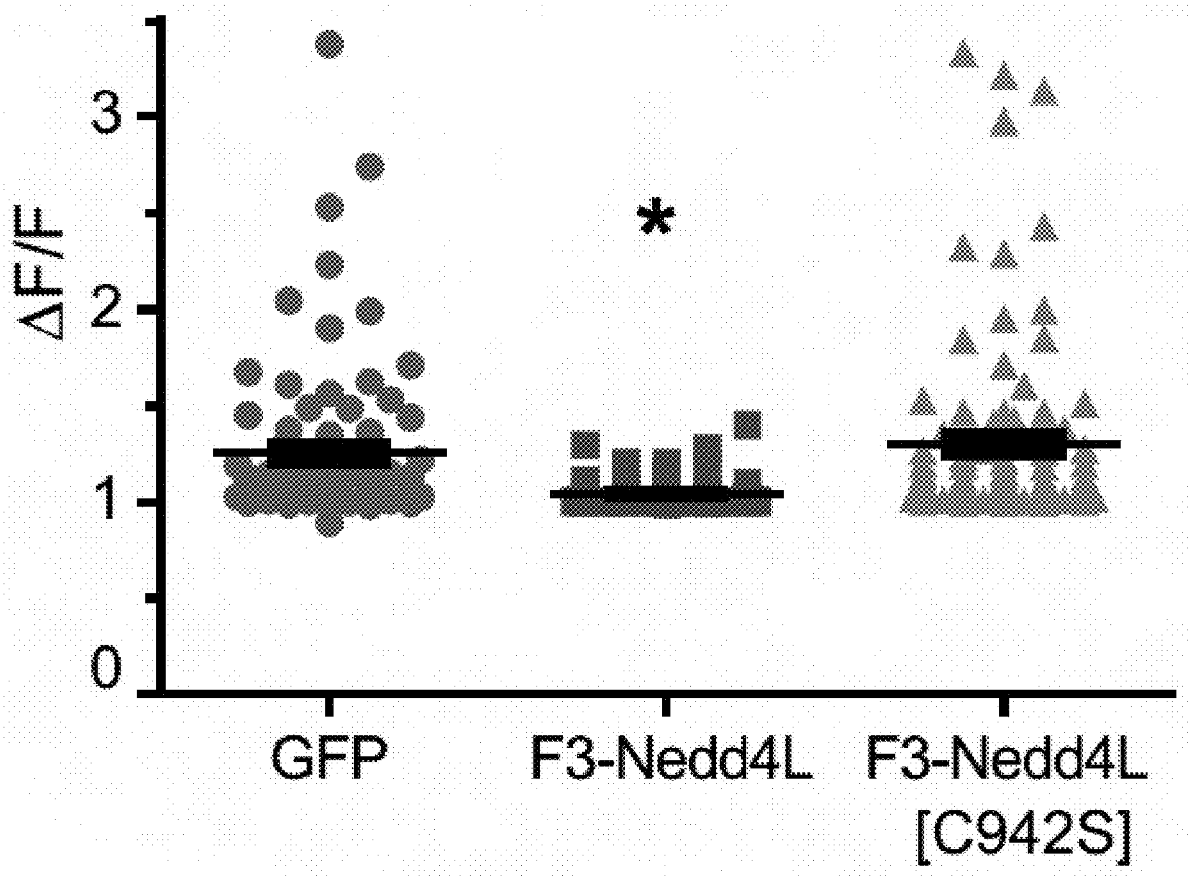

It was next tested the efficacy of $Ca_V$-aβlator to suppress HVACCs in murine dorsal root ganglion (DRG) neurons which were of interest because they express multiple $Ca_V$1/$Ca_V$2 channel types (Murali et al., 2015; McCallum et al., 2011), and also play a key role in the processing of noxious signals including pain and itch (Han et al., 2013; Kim et al., 2016). Cultured DRG neurons were infected with adenovirus expressing either GFP, $Ca_V$-aβlator, or nb.F3-Nedd4L [C942S]. Given their heterogeneous nature, fura-2 was first used to measure calcium influx into a population of DRG neurons in response to depolarization with 40 mM KCl (FIGS. 6A and 6B). Recordings were done in the presence of 5 μM mibefradil to block low-voltage-activated T-type calcium channels which are also prevalent in these cells (Puckerin et al., 2018; Jagodic et al., 2008). In neurons expressing GFP or nb.F3-Nedd4L[C942S], a substantial fraction of cells displayed large increases in fura-2-reported $Ca^{2+}$ transients in response to 40 mM KCl, indicating the opening of $Ca_V$1/$Ca_V$2 channels (FIGS. 6A and 6B). By contrast, depolarization-induced $Ca^{2+}$ influx was virtually eliminated in neurons expressing $Ca_V$-aβlator, demonstrating highly efficient $Ca_V$-ablation in this system (FIGS. 6A and 6B).

Figure 6C:
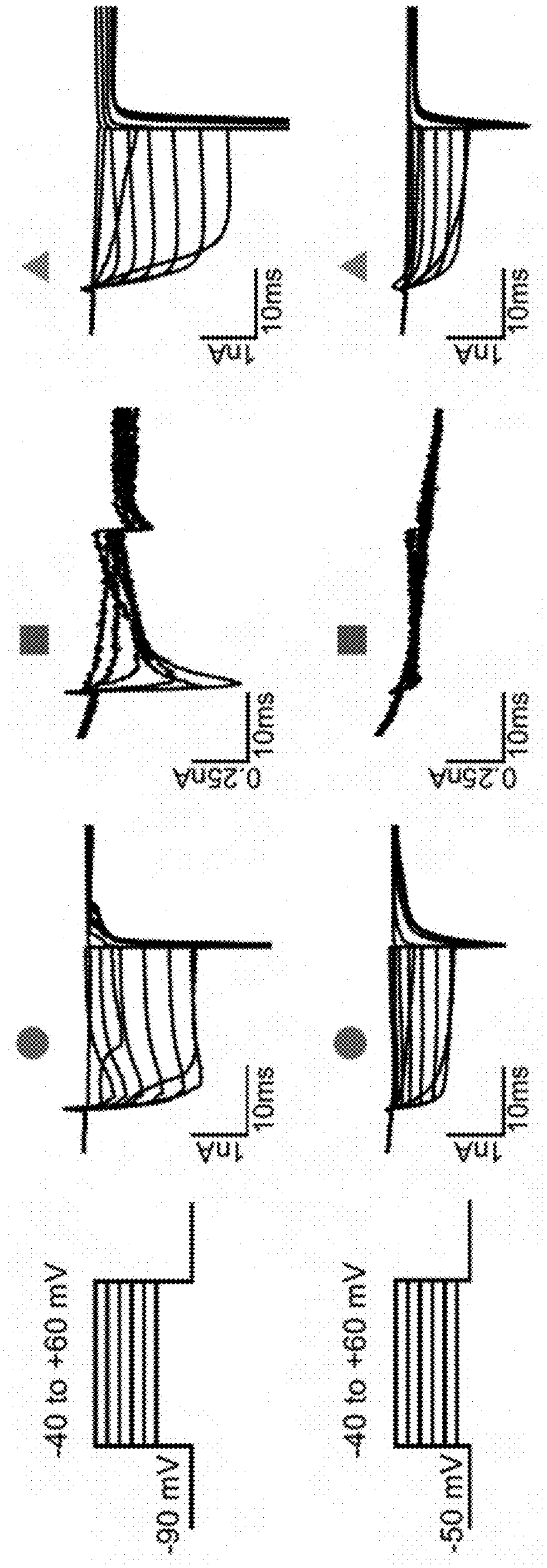
Figure 6D:
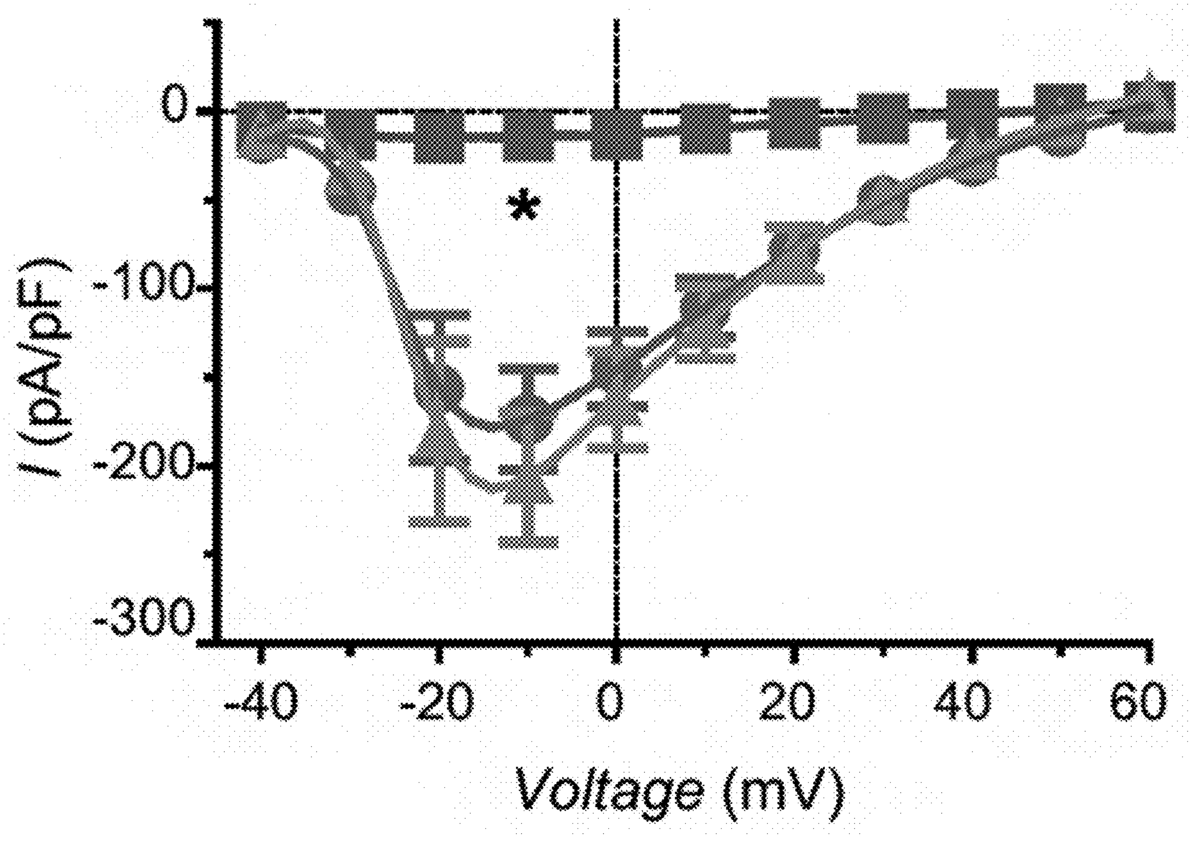

Whole-cell patch clamp was used to further characterize the impact of $Ca_V$-aβlator on calcium currents in DRG neurons. It was of particular interest to determine relative effects of $Ca_V$-aβlator on HVACCs and LVA T-type channels that are present in a subset of DRG neurons. We recorded families of whole-cell currents evoked by test pulses (from −40 mV to +60 mV in 10 mV increments) from a holding potential of either −90 mV or −50 mV to inactivate any T-type channel present (FIG. 6C). Cells expressing GFP (control) or F3-Nedd4L[C942S] displayed large $I_{Ba}$ irrespective of the holding potential (FIGS. 6C and 6D; $I_{peak,-10mV}$=−173.9±28.2 pA/pF, n=6 for GFP, $I_{peak,-10mv}$=−206.7±36.4 pA/pF, n=5 for F3-Nedd4L [C942S]), though those recorded with a −50 mV holding potential had a lower amplitude reflecting inactivation of T-type channels and also a fraction of HVACCs. Cells expressing $Ca_V$-aβlator displayed essentially no HVACC currents (FIGS. 6C and 6D; $I_{peak,-10mV}$=−14.3±6.2 pA/pF), most evident as an absence of $I_{Ba}$ recorded from a −50 mV holding potential (FIG. 6C, middle). Moreover, in these cells, when currents were recorded from a −90 mV holding potential, they displayed fast inactivation kinetics characteristic of T-type channels (FIG. 6C). Overall, these results indicate $Ca_V$-ablator selectively eliminates HVACCs in DRG neurons without impacting LVA T-type channels.

Figure 6E:
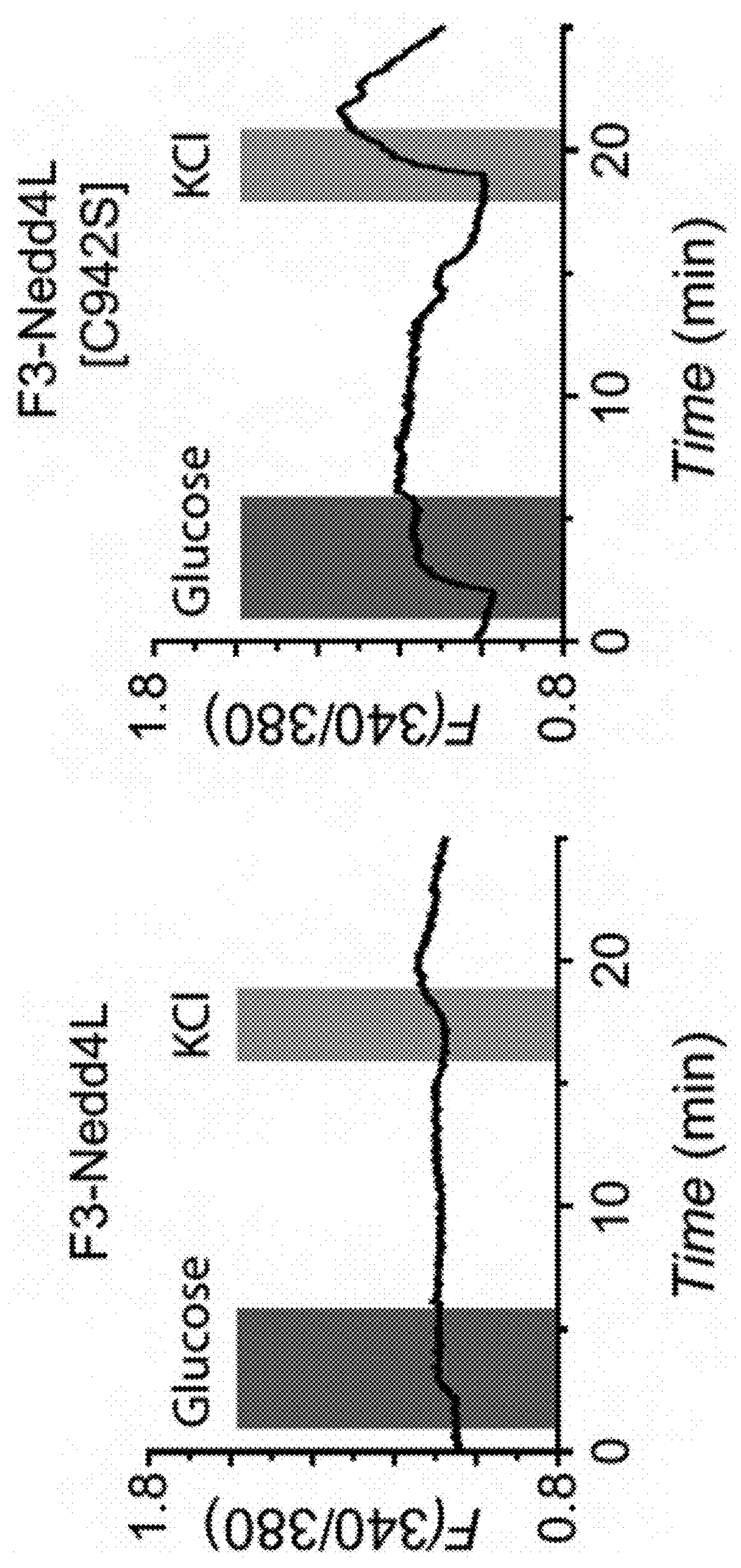
Figure 6F:
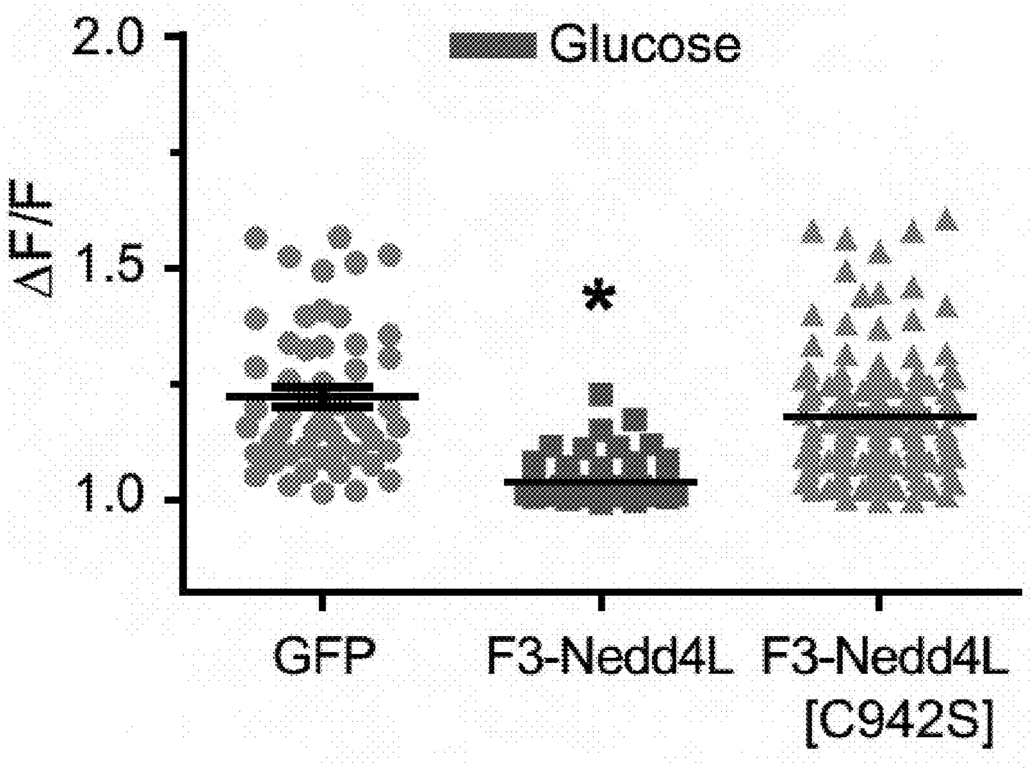
Figure 6G:
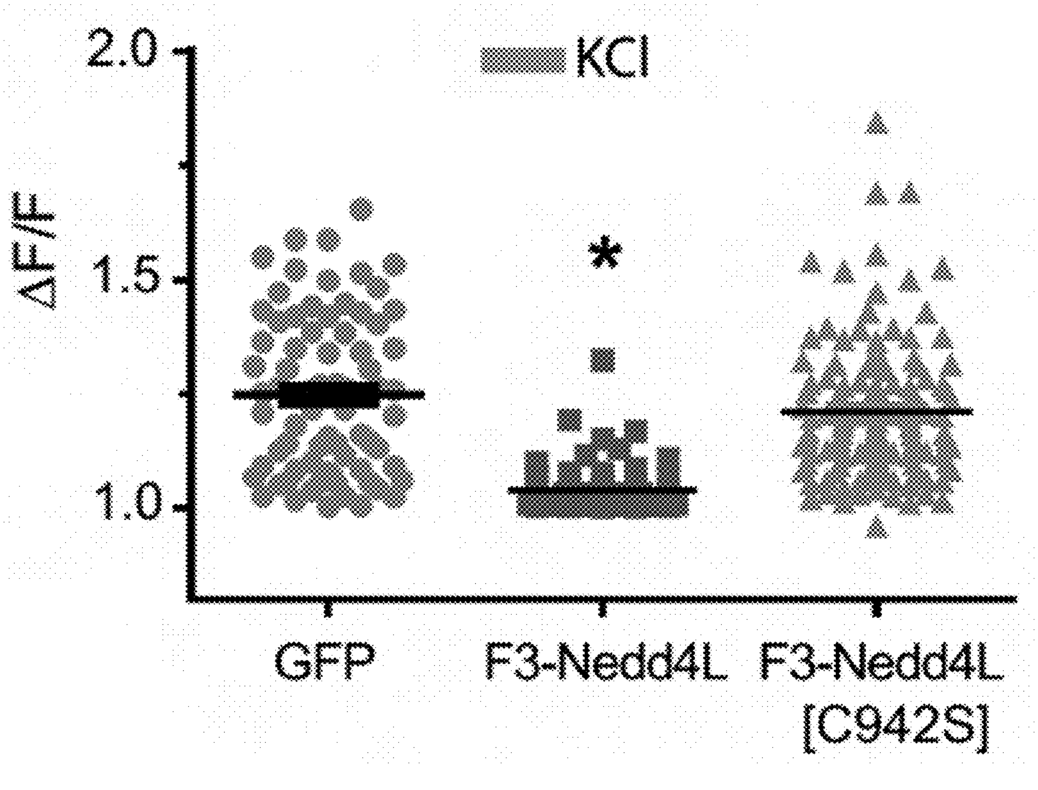

Finally, it was tested whether $Ca_V$-ablator is also effective in murine pancreatic δ-cells, which have multiple $Ca_V$ channel types ($Ca_V$1.2, $Ca_V$1.3, and $Ca_V$2.1) involved in insulin release (Yang and Berggren, 2006). Adenovirus was used to infect digested islets isolated from transgenic mice expressing tdTomato in pancreatic β-cells. Control cells expressing GFP or nb.F3-Nedd4L[C942S] displayed robust glucose- or KCl-evoked fura-2-reported $Ca^{2+}$ transients that were essentially abolished in cells expressing $Ca_V$-aβlator (FIGS. 6E-6G). Altogether, these results reveal the exceptional activity of $Ca_V$-aβlator as a genetically-encoded HVACC inhibitor that is effective across diverse cellular contexts.

Example 6

Discussion

The present disclosure introduces $Ca_V$-aβlator as a novel genetically-encoded molecule that potently inhibits HVACCs by targeting auxiliary $Ca_V\beta$ subunits. $Ca_V$-aβlator combines the exquisite specificity of a $Ca_V\beta$-targeted nanobody and the powerfully consequential catalytic activity of an E3 ubiquitin ligase. Four distinct aspects of the present disclosure were discussed, based on viewing $Ca_V$-aβlator from different perspectives; 1) as a unique tool to selectively erase HVACCs in cells, 2) as a method to probe mechanisms of HVACC regulation and trafficking, 3) as a potential therapeutic, and 4) as a prototype engineered protein that enables probing new dimensions of macro-molecular membrane protein signaling.

$Ca^{2+}$ is a universal second messenger critical to the biology of virtually all cells. In excitable cells, both LVACCs and HVACCs transduce electrical signals encoded in action potentials into changes in intracellular $Ca^{2+}$ that then drive many biological responses. In cells expressing both classes of channels, the physiological effects mediated specifically through LVACCs versus HVACCs in vivo can be difficult to decipher. $Ca_V$-aβlator now presents as a tool that can be deployed in target cells to virtually erase all HVACCs while leaving LVACC actions intact. The closest existing proteins that can similarly eliminate HVACCs are RGK GTPases which are capable of potently inhibiting $Ca_V$1/$Ca_V$2 channels when over-expressed in target cells (Murata et al., 2004; Chen et al., 2005; Xu et al., 2010; Puckerin et al., 2018; Bannister et al., 2008). However, a distinct disadvantage of RGKs is their propensity for off-target effects due to their known interactions with, and regulation of, cytoskeletal proteins and other signaling molecules including 14-3-3, calmodulin, and CaM kinase II (Yang and Colecraft, 2013; Correll et al., 2008; Royer et al., 2018; Béguin et al., 2005). Over the last two decades, several groups have sought to disrupt the $\alpha_1$-$Ca_V\beta$ interaction with either small molecules or by over-expressing the AID peptide as a $Ca_V\beta$ sponge (Findeisen et al., 2017; Chen, 2018; Khanna et al., 2019; Yang et al., 2019). While this approach has shown some efficacy in certain instances, the potency of HVACC inhibition falls well short of that achieved here with $Ca_V$-aβlator. Indeed, over-expressing the AID peptide in adult cardiac myocytes is not effective in inhibiting $Ca_V$1.2 channels (Yang et al., 2019), because in this context $\alpha_{1C}$ binding to $Ca_V\beta$ is not absolutely required for channel trafficking to the surface (Yang et al., 2019; Meissner et al., 2011). Nevertheless, the ability of $Ca_V$-aβlator to essentially eradicate $I_{Ca,L}$ in adult cardiomyocytes indicates that under normal physiological conditions essentially all $\alpha_{1C}$ subunits are associated with a $Ca_V\beta$ in ventricular heart cells.

$Ca_V$1/$Ca_V$2 channels and other surface membrane proteins spend a significant portion of their life cycles in intracellular compartments reflecting their biogenesis, recycling, and ultimate destruction. The signals regulating HVACC degradation and trafficking among compartments are arcane and poorly understood, but likely prominently involve post-translational modifications of channel subunits. Here, we show that targeted ubiquitination of $\alpha_{1C}/\beta_2$ complexes in cardiomyocytes with $Ca_V$-aβlator specifically arrests $Ca_V$1.2 channels in Rab7-positive late endosomes. $Ca_V$-aβlator possesses the catalytic HECT domain of Nedd4L which is known to principally catalyze the addition of K63-linkage polyubiquitin chains to target proteins (Kim and Huibregtse, 2009; Scheffner and Kumar, 2014). Thus, our results suggest that K63-ubiquitin chains on $\alpha_{1C}/\beta_2$ subunits may be a key signal directing $Ca_V$1.2 channels to late endosomes. We further found that targeted ubiquitination of HVACC $\alpha_1$ subunits with $Ca_V$-aβlator did not lead to their enhanced degradation either in heterologous cells or cardiomyocytes. By contrast, using a GFP nanobody to target the Nedd4L HECT domain to YFP-tagged KCNQ1, a known substrate of endogenous Nedd4L, resulted in reduced expression of this $K^+$ channel pore-forming $\alpha_1$ subunit (Kanner et al., 2017). Hence, the impact of Nedd4L HECT domain on the stability of membrane proteins is likely substrate-dependent. We speculate that arming nb.F3 with the catalytic domains of other types of E3 ligases that catalyze formation of different polyubiquitin chains will elucidate the precise signals dictating $Ca_V$1/$Ca_V$2 channel degradation and trafficking among distinct compartments. Beyond ubiquitination, the approach could also be potentially used to elucidate functional consequences and mechanisms of other post-translational modifications such as phosphorylation/dephosphorylation on $Ca_V$1/$Ca_V$2 channels, as well as to localize sensors that report on signals within HVACC nano-domains in live cells.

Blocking the activity of specific HVACCs with small molecules is a prevailing or potential therapy for many cardiovascular and neurological diseases including; pain, hypertension, cardiac arrhythmias, epilepsy, and Parkinson's disease (Zamponi, 2016). A limitation of small molecule or toxin blockers for HVACCs is the propensity for off-target effects due to their inevitable widespread distribution when administered to a patient. In some circumstances such off-target effects may limit the therapeutic window sufficiently to adversely affect treatment efficacy. Genetically-encoded HVACC inhibitors have great potential to be useful therapeutics with the advantage that their expression can be restricted to target tissues/cell types, or even to spatially discrete channels within single cells (Murata et al., 2004; Makarewich et al., 2012). Given its potency in silencing HVACC activity, $Ca_V$-aβlator could be a lead molecule for future development into a gene therapy for particular applications where a genetically-encoded HVACC inhibitor is warranted. For this purpose, it may be desirable to generate $Ca_V$-aβlator versions whose time course and extent of action could be tuned by either a small molecule or light. Indeed, this is a focus of ongoing work.

Finally, an exciting prospect is the potential of $Ca_V$-aβlator as a prototype that can be further developed to engineer proteins that regulate $Ca_V1/Ca_V2$ channel complexes with new dimensions of specificity. For example, a prevailing idea is that $Ca_V1/Ca_V2$ channels of a particular type (e.g. $Ca_V1.2$ channels in cardiomyocytes) may yet form discrete signaling units with different functional outputs in single cells based on their incorporation into divergent macro-molecular complexes (Shaw and Colecraft, 2013). There are tantalizing hints that different $Ca_V\beta$ isoforms could be a node of signal diversification by promoting formation of molecularly distinct HVACC macro-molecular complexes (McEnery et al., 1998; Brice and Dolphin, 1999; Campiglio and Flucher, 2015). Hence, the ability to inhibit specific $Ca_V$ channel macro-molecular complexes based on the identity of the constituent $Ca_V\beta$ is biologically important, yet not rigorously addressable with conventional knockout/knockdown approaches. However, this capability may be readily achieved with $Ca_V$-aβlators directed towards particular $Ca_V\beta$ isoforms. A challenge to realize this possibility is the development of $Ca_V\beta$ isoform-specific nanobodies which should be feasible given that there is sequence divergence among $Ca_V\beta$s outside the conserved src homology 3 (SH3) and guanylate kinase (GK) domains (Buraei and Yang, 2010). In a broader context, the phenomenon of ion channel pore-forming $\alpha_1$ subunits assembled with diverse auxiliary subunits in individual cells is common throughout biology (O'Malley and Isom, 2015; Copits and Swanson, 2012; Trimmer, 2015). Hence, $Ca_V$-aβlator-inspired molecules and approaches might be expected to elucidate functional dimensions of ion channel macro-molecular complex signaling that, to date, have remained refractory to analyses.

DOCUMENTS CITED

1. Albuquerque C, Joseph D J, Choudhury P, MacDermott AB. Dissection, plating, and maintenance of dorsal root ganglion neurons for monoculture and for coculture with dorsal horn neurons. Cold Spring Harbor Protocols. 2009: prot5275.
2. Andris-Widhopf J, Rader C, Steinberger P, Fuller R, Barbas C F. Methods for the generation of chicken monoclonal antibody fragments by phage display. Journal of Immunological Methods. 2000; 242:159-181. doi: 10.1016/S0022-1759(00)00221-0.
3. Aromolaran A S, Subramanyam P, Chang D D, Kobertz W R, Colecraft H M. LQT1 mutations in KCNQ1 C-terminus assembly domain suppress IKs using different mechanisms. Cardiovascular Research. 2014; 104:501-511. doi: 10.1093/cvr/cvu231.
4. Bannister R A, Colecraft H M, Beam K G. Rem inhibits skeletal muscle EC coupling by reducing the number of functional L-type Ca2+ channels. Biophysical Journal. 2008; 94:2631-2638. doi: 10.1529/biophysj.107.116467.
5. Béguin P, Nagashima K, Gonoi T, Shibasaki T, Takahashi K, Kashima Y, Ozaki N, Geering K, Iwanaga T, Seino S. Regulation of Ca2+ channel expression at the cell surface by the small G-protein kir/Gem. Nature. 2001; 411:701-706. doi: 10.1038/35079621.
6. Béguin P, Mahalakshmi R N, Nagashima K, Cher D H, Takahashi A, Yamada Y, Seino Y, Hunziker W. 14-3-3 and calmodulin control subcellular distribution of kir/Gem and its regulation of cell shape and calcium channel activity. Journal of Cell Science. 2005; 118:1923-1934. doi: 10.1242/jcs.02321.
7. Bers D M. Cardiac excitation-contraction coupling. Nature. 2002; 415:198-205. doi: 10.1038/415198a.
8. Brice N L, Dolphin A C. Differential plasma membrane targeting of voltage-dependent calcium channel subunits expressed in a polarized epithelial cell line. The Journal of Physiology. 1999; 515:685-694. doi: 10.1111/j.1469-7793.1999.685ab.x.
9. Buraei Z, Yang J. The β subunit of voltage-gated Ca2+ channels. Physiological Reviews. 2010; 90:1461-1506. doi: 10.1152/physrev.00057.2009.
10. Campiglio M, Flucher B E. The role of auxiliary subunits for the functional diversity of voltage-gated calcium channels. Journal of Cellular Physiology. 2015; 230:2019-2031. doi: 10.1002/jcp.24998.
11. Chen Y-hang, Li M-hui, Zhang Y, He L-ling, Yamada Y, Fitzmaurice A, Shen Y, Zhang H, Tong L, Yang J. Structural basis of the al-6 subunit interaction of voltage-gated Ca2+ channels. Nature. 2004; 429:675-680. doi: 10.1038/nature02641.
12. Chen H, Puhl H L, Niu S L, Mitchell D C, Ikeda S R. Expression of Rem2, an RGK family small GTPase, reduces N-type calcium current without affecting channel surface density. Journal of Neuroscience. 2005; 25:9762-9772. doi: 10.1523/JNEUROSCI.3111-05.2005.
13. Chen X. Small-molecule CaValpha1CaVbeta antagonist suppresses neuronal voltage-gated calcium-channel trafficking. PNAS. 2018; 115:E10566-E10575. doi: 10.1073/pnas.1813157115.
14. Chien A J, Carr K M, Shirokov R E, Rios E, Hosey M M. Identification of palmitoylation sites within the L-type calcium channel beta2a subunit and effects on channel function. Journal of Biological Chemistry. 1996; 271: 26465-26468. doi: 10.1074/jbc.271.43.26465.
15. Colecraft H M, Alseikhan B, Takahashi S X, Chaudhuri D, Mittman S, Yegnasubramanian V, Alvania R S, Johns D C, Marbán E, Yue D T. Novel functional properties of ca(2+) channel beta subunits revealed by their expression in adult rat heart cells. The Journal of Physiology. 2002; 541:435-452. doi: 10.1113/jphysiol.2002.018515.
16. Copits B A, Swanson G T. Dancing partners at the synapse: auxiliary subunits that shape kainate receptor function. Nature Reviews Neuroscience. 2012; 13:675-686. doi: 10.1038/nrn3335.
17. Correll R N, Pang C, Niedowicz D M, Finlin B S, Andres D A. The RGK family of GTP-binding proteins: regulators of voltage-dependent calcium channels and cytoskeleton remodeling. Cellular Signalling. 2008; 20:292-300. doi: 10.1016/j.cellsig.2007.10.028.

18. Dolphin A C. Calcium channel auxiliary α2δ and β subunits: trafficking and one step beyond. Nature Reviews Neuroscience. 2012; 13:542-555. doi: 10.1038/nrn3311.
19. Findeisen F, Campiglio M, Jo H, Abderemane-Ali F, Rumpf C H, Pope L, Rossen N D, Flucher B E, DeGrado W F, Minor D L. Stapled Voltage-Gated calcium channel ($Ca_V$) α-Interaction Domain (AID) Peptides Act As Selective Protein-Protein Interaction Inhibitors of $Ca_V$ Function. ACS Chemical Neuroscience. 2017; 8:1313-1326. doi: 10.1021/acschemneuro.6b00454.
20. Finlin B S, Crump S M, Satin J, Andres D A. Regulation of voltage-gated calcium channel activity by the rem and rad GTPases. PNAS. 2003; 100:14469-14474. doi: 10.1073/pnas.2437756100.
21. Gao S, Alarcon C, Sapkota G, Rahman S, Chen P Y, Goerner N, Macias M J, Erdjument-Bromage H, Tempst P, Massague J. Ubiquitin ligase Nedd4L targets activated Smad2/3 to limit TGF-beta signaling. Molecular Cell. 2009; 36:457-468. doi: 10.1016/j.molcel.2009.09.043.
22. Gee N S, Brown J P, Dissanayake V U, Offord J, Thurlow R, Woodruff G N. The novel anticonvulsant drug, gabapentin (Neurontin), binds to the alpha2delta subunit of a calcium channel. Journal of Biological Chemistry. 1996; 271:5768-5776. doi: 10.1074/jbc.271.10.5768.
23. Gibson D G, Young L, Chuang R Y, Venter J C, Hutchison C A, Smith H O. Enzymatic assembly of DNA molecules up to several hundred kilobases. Nature Methods. 2009; 6:343-345. doi: 10.1038/nmeth.1318.
24. Goehring A, Lee C H, Wang K H, Michel J C, Claxton D P, Baconguis I, Althoff T, Fischer S, Garcia K C, Gouaux E. Screening and large-scale expression of membrane proteins in mammalian cells for structural studies. Nature Protocols. 2014; 9:2574-2585. doi: 10.1038/nprot.2014.173.
25. Han L, Ma C, Liu Q, Weng H J, Cui Y, Tang Z, Kim Y, Nie H, Qu L, Patel K N, Li Z, McNeil B, He S, Guan Y, Xiao B, Lamotte R H, Dong X. A subpopulation of nociceptors specifically linked to itch. Nature Neuroscience. 2013; 16:174-182. doi: 10.1038/nn.3289.
26. Jagodic M M, Pathirathna S, Joksovic P M, Lee W, Nelson M T, Naik A K, Su P, Jevtovic-Todorovic V, Todorovic S M. Upregulation of the T-type calcium current in small rat sensory neurons after chronic constrictive injury of the sciatic nerve. Journal of Neurophysiology. 2008; 99:3151-3156. doi: 10.1152/jn.01031.2007.
27. Kanner S A, Morgenstern T, Colecraft H M. Sculpting ion channel functional expression with engineered ubiquitin ligases. eLife. 2017; 6:e29744. doi: 10.7554/eLife.29744.
28. Khanna R, Yu J, Yang X, Moutal A, Chefdeville A, Gokhale V, Shuja Z, Chew L A, Bellampalli S S, Luo S, Francois-Moutal L, Serafini M J, Ha T, Perez-Miller S, Park K D, Patwardhan A M, Streicher J M, Colecraft H M, Khanna M. Targeting the CaVα-CaVβ interaction yields an antagonist of the N-type CaV2.2 channel with broad antinociceptive efficacy. Pain. 2019; 160:1644-1661. doi: 10.1097/j.pain.0000000000001524.
29. Kim Y S, Anderson M, Park K, Zheng Q, Agarwal A, Gong C, Saijilafu, Young L, He S, LaVinka P C, Zhou F, Bergles D, Hanani M, Guan Y, Spray D C, Dong X. Coupled activation of primary sensory neurons contributes to chronic pain. Neuron. 2016; 91:1085-1096. doi: 10.1016/j.neuron.2016.07.044.
30. Kim H C, Huibregtse J M. Polyubiquitination by HECT E3s and the determinants of chain type specificity. Molecular and Cellular Biology. 2009; 29:3307-3318. doi: 10.1128/MCB.00240-09.
31. Makarewich C A, Correll R N, Gao H, Zhang H, Yang B, Berretta R M, Rizzo V, Molkentin J D, Houser S R. A caveolae-targeted L-type $Ca^{2+}$ channel antagonist inhibits hypertrophic signaling without reducing cardiac contractility. Circulation Research. 2012; 110:669-674. doi: 10.1161/CIRCRESAHA.111.264028.
32. McCallum J B, Wu H E, Tang Q, Kwok W M, Hogan Q H. Subtype-specific reduction of voltage-gated calcium current in medium-sized dorsal root ganglion neurons after painful peripheral nerve injury. Neuroscience. 2011; 179:244-255. doi: 10.1016/j.neuroscience.2011.01.049.
33. McEnery M W, Copeland T D, Vance C L. Altered expression and assembly of N-type calcium channel alpha1B and beta subunits in epileptic lethargic (lh/lh) mouse. The Journal of Biological Chemistry. 1998; 273: 21435-21438. doi: 10.1074/jbc.273.34.21435.
34. McMahon C, Baier A S, Pascolutti R, Wegrecki M, Zheng S, Ong J X, Erlandson S C, Hilger D, Rasmussen S G F, Ring A M, Manglik A, Kruse A C. Yeast surface display platform for rapid discovery of conformationally selective nanobodies. Nature Structural & Molecular Biology. 2018; 25:289-296. doi: 10.1038/s41594-018-0028-6.
35. Meissner M, Weissgerber P, Londoño J E, Prenen J, Link S, Ruppenthal S, Molkentin J D, Lipp P, Nilius B, Freichel M, Flockerzi V. Moderate calcium channel dysfunction in adult mice with inducible cardiomyocyte-specific excision of the cacnb2 gene. Journal of Biological Chemistry. 2011; 286:15875-15882. doi: 10.1074/jbc. M111.227819.
36. Murali S S, Napier I A, Mohammadi S A, Alewood P F, Lewis R J, Christie M J. High-voltage-activated calcium current subtypes in mouse DRG neurons adapt in a subpopulation-specific manner after nerve injury. Journal of Neurophysiology. 2015; 113:1511-1519. doi: 10.1152/jn.00608.2014.
37. Murata M, Cingolani E, McDonald A D, Donahue J K, Marbán E. Creation of a genetic calcium channel blocker by targeted gem gene transfer in the heart. Circulation Research. 2004; 95:398-405. doi: 10.1161/01.RES.0000138449.85324.c5.
38. O'Malley H A, Isom L L. Sodium channel β subunits: emerging targets in channelopathies. Annual Review of Physiology. 2015; 77:481-504. doi: 10.1146/annurev-physiol-021014-071846.
39. Opatowsky Y, Chomsky-Hecht O, Kang M G, Campbell K P, Hirsch J A. The voltage-dependent calcium channel beta subunit contains two stable interacting domains. Journal of Biological Chemistry. 2003; 278:52323-52332. doi: 10.1074/jbc. M303564200.
40. Pardon E, Laeremans T, Triest S, Rasmussen S G, Wohlkönig A, Ruf A, Muyldermans S, Hol W G, Kobilka B K, Steyaert J. A general protocol for the generation of nanobodies for structural biology. Nature Protocols. 2014; 9:674-693. doi: 10.1038/nprot.2014.039.
41. Pragnell M, De Waard M, Mori Y, Tanabe T, Snutch T P, Campbell K P. Calcium channel beta-subunit binds to a conserved motif in the 1-11 cytoplasmic Linker of the alpha 1-subunit. Nature. 1994; 368:67-70. doi: 10.1038/368067a0.
42. Puckerin A A, Chang D D, Shuja Z, Choudhury P, Scholz J, Colecraft H M. Engineering selectivity into RGK GTPase inhibition of voltage-dependent calcium channels. PNAS. 2018; 115:12051-12056. doi: 10.1073/pnas.1811024115.

43. Rink J, Ghigo E, Kalaidzidis Y, Zerial M. Rab conversion as a mechanism of progression from early to late endosomes. Cell. 2005; 122:735-749. doi: 10.1016/j.cell.2005.06.043.
44. Royer L, Herzog J J, Kenny K, Tzvetkova B, Cochrane J C, Marr M T, Paradis S. The Ras-like GTPase Rem2 is a potent inhibitor of calcium/calmodulin-dependent kinase II activity. Journal of Biological Chemistry. 2018; 293:14798-14811. doi: 10.1074/jbc.RA118.003560.
45. Scheffner M, Kumar S. Mammalian HECT ubiquitin-protein ligases: biological and pathophysiological aspects. Biochimica Et Biophysica Acta (BBA)—Molecular Cell Research. 2014; 1843:61-74. doi: 10.1016/j.bbamcr.2013.03.024.
46. Scriven D R, Dan P, Moore E D. Distribution of proteins implicated in excitation-contraction coupling in rat ventricular myocytes. Biophysical Journal. 2000; 79:2682-2691. doi: 10.1016/S0006-3495(00)76506-4.
47. Shaw R M, Colecraft H M. L-type calcium channel targeting and local signalling in cardiac myocytes. Cardiovascular Research. 2013; 98:177-186. doi: 10.1093/cvr/cvt021.
48. Stull N D, Breite A, McCarthy R, Tersey S A, Mirmira R G. Mouse islet of Langerhans isolation using a combination of purified collagenase and neutral protease. Journal of Visualized Experiments. 2012; 4137:e4137. doi: 10.3791/4137.
49. Subramanyam P. Manipulating L-type calcium channels in cardiomyocytes using split-intein protein transsplicing. PNAS. 2013; 110:15461-15466.
50. Trimmer J S. Subcellular localization of K+ channels in mammalian brain neurons: remarkable precision in the midst of extraordinary complexity. Neuron. 2015; 85:238-256. doi: 10.1016/j.neuron.2014.12.042.
51. Van Petegem F, Clark K A, Chatelain F C, Minor D L. Structure of a complex between a voltage-gated calcium channel beta-subunit and an alpha-subunit domain. Nature. 2004; 429:671-675. doi: 10.1038/nature02588.
52. Waithe D, Ferron L, Page K M, Chaggar K, Dolphin A C. Beta-subunits promote the expression of ca(V)2.2 channels by reducing their proteasomal degradation. The Journal of Biological Chemistry. 2011; 286:9598-9611. doi: 10.1074/jbc.M110.195909.
53. Ward Y, Spinelli B, Quon M J, Chen H, Ikeda S R, Kelly K. Phosphorylation of critical serine residues in gem separates cytoskeletal reorganization from down-regulation of calcium channel activity. Molecular and Cellular Biology. 2004; 24:651-661. doi: 10.1128/MCB.24.2.651-661.2004.
54. Xu X, Marx S O, Colecraft H M. Molecular mechanisms, and selective pharmacological rescue, of Rem-inhibited CaV1.2 channels in heart. Circulation Research. 2010; 107:620-630. doi: 10.1161/CIRCRESAHA.110.224717.
55. Yang T, Xu X, Kernan T, Wu V, Colecraft H M. Rem, a member of the RGK GTPases, inhibits recombinant CaV1.2 channels using multiple mechanisms that require distinct conformations of the GTPase. The Journal of Physiology. 2010; 588:1665-1681. doi: 10.1113/jphysiol.2010.187203.
56. Yang T, He L L, Chen M, Fang K, Colecraft H M. Bio-inspired voltage-dependent calcium channel blockers. Nature Communications. 2013; 4:2540. doi: 10.1038/ncomms3540.
57. Yang L, Katchman A, Kushner J, Kushnir A, Zakharov S I, Chen B X, Shuja Z, Subramanyam P, Liu G, Papa A, Roybal D, Pitt G S, Colecraft H M, Marx S O. Cardiac CaV1.2 channels require β subunits for β-adrenergic-mediated modulation but not trafficking. Journal of Clinical Investigation. 2019; 129:647-658. doi: 10.1172/JC1123878.
58. Yang S N, Berggren P O. The role of voltage-gated calcium channels in pancreatic beta-cell physiology and pathophysiology. Endocrine Reviews. 2006; 27:621-676. doi: 10.1210/er.2005-0888.
59. Yang T, Colecraft H M. Regulation of voltage-dependent calcium channels by RGK proteins. Biochimica Et Biophysica Acta (BBA)—Biomembranes. 2013; 1828:1644-1654. doi: 10.1016/j.bbamem.2012.10.005.
60. Young K, Lin S, Sun L, Lee E, Modi M, Hellings S, Husbands M, Ozenberger B, Franco R. Identification of a calcium channel modulator using a high throughput yeast two-hybrid screen. Nature Biotechnology. 1998; 16:946-950. doi: 10.1038/n bt1098-946.
61. Zamponi G W, Striessnig J, Koschak A, Dolphin A C. The physiology, pathology, and pharmacology of Voltage-Gated calcium channels and their future therapeutic potential. Pharmacological Reviews. 2015; 67:821-870. doi: 10.1124/pr.114.009654.
62. Zamponi G W. Targeting voltage-gated calcium channels in neurological and psychiatric diseases. Nature Reviews Drug Discovery. 2016; 15:19-34. doi: 10.1038/nrd.2015.5.

All documents cited in this application are hereby incorporated by reference as if recited in full herein.

Although illustrative embodiments of the present disclosure have been described herein, it should be understood that the disclosure is not limited to those described, and that various other changes or modifications may be made by one skilled in the art without departing from the scope or spirit of the disclosure.

---

What is claimed is:

1. A composition comprising a nucleic acid molecule encoding a polypeptide comprising (i) an E3 ubiquitin ligase operably connected to (ii) a nanobody capable of binding to a Cavβ auxiliary subunit, wherein the amino acid sequence of the encoded nanobody comprises three complementarity determining regions (CDRs): CDR1, CDR2, and CDR3, and wherein the amino acid sequence of CDR1 comprises the amino acid sequence of SEQ ID NO: 83, the amino acid sequence of CDR2 comprises the amino acid sequence SEQ ID NO: 84, and the amino acid sequence of CDR3 comprises the amino acid sequence of SEQ ID NO: 85.

2. The composition of claim 1, wherein the encoded nanobody is capable of binding any one or more of $Cav\beta_1$ auxiliary subunit, $Cav\beta_2$ auxiliary subunit, $Cav\beta_3$ auxiliary subunit, or $Cav\beta_4$ auxiliary subunit.

3. The composition of claim 1, wherein the encoded nanobody is capable of binding $Cav\beta_1$ auxiliary subunit, $Cav\beta_2$ auxiliary subunit, $Cav\beta_3$ auxiliary subunit, and $Cav\beta_4$ auxiliary subunit.

4. The composition of claim 3, wherein the amino acid sequence of the encoded nanobody comprises the amino acid sequence of SEQ ID NO: 86.

5. The composition of claim 3, wherein the encoded E3 ubiquitin ligase is Nedd4-2.

6. The composition of claim 1, wherein the amino acid sequence of the encoded nanobody comprises the amino acid sequence of SEQ ID NO: 86.

7. The composition of claim 1, wherein the encoded E3 ubiquitin ligase is Nedd4-2.

8. The composition of claim 1, wherein (i) is operably connected to (ii) through a linker.

9. The composition of claim 1, wherein the nucleic acid molecule is carried on a vector.

10. The composition of claim 9, wherein the vector is a viral vector.

11. The composition of claim 10, wherein the viral vector is an adenoviral vector.

12. The composition of claim 10, wherein the viral vector is adenoassociated viral vector.

13. The composition of claim 9, wherein the vector comprises a tissue specific promoter.

14. The composition of claim 13, wherein the tissue specific promoter is a B29 promoter, CD14 promoter, CD43 promoter, CD45 promoter, CD68 promoter, desmin promoter, elastase-1 promoter, endoglin promoter, fibronectin promoter, flt-1 promoter, GFAP promoter, GP IIb promoter, ICAM-2 promoter, mouse INF-b promoter, Mb promoter, Npshl promoter, OG-2 promoter, SP-B promoter, SYN-1 promoter, WASP promoter, and composite promoters such as SV40/bAlb promoter, SV40/hAlb promoter, SV40/CD43 promoter, SV40/CD45 promoter, or NSE/RU5' promoter.

* * * * *